(12) United States Patent
Zhu et al.

(10) Patent No.: US 8,058,435 B2
(45) Date of Patent: Nov. 15, 2011

(54) INTERMEDIATE AND PROCESS OF PREPARATION OF ECTEINASCIDIN SUCH AS ECTEINASCIDINES-583,597 USING SUCH INTERMEDIATE

(75) Inventors: Jieping Zhu, Gif S/Yvette (FR); Michèle Bois-Choussy, Fontenay Aux Roses (FR); Jinchun Chen, Bures sur Yvette (FR); Xiaochuan Chen, Bures sur Yvettes (FR)

(73) Assignee: Centre National de la Recherche Scientifique (CNRS) (FR)

( * ) Notice: Subject to any disclaimer, the term of this patent is extended or adjusted under 35 U.S.C. 154(b) by 128 days.

(21) Appl. No.: 12/083,740

(22) PCT Filed: Oct. 20, 2006

(86) PCT No.: PCT/EP2006/067611
§ 371 (c)(1),
(2), (4) Date: Apr. 17, 2008

(87) PCT Pub. No.: WO2007/045686
PCT Pub. Date: Apr. 26, 2007

(65) Prior Publication Data
US 2009/0171080 A1 Jul. 2, 2009

Related U.S. Application Data

(60) Provisional application No. 60/728,295, filed on Oct. 20, 2005.

(30) Foreign Application Priority Data

Oct. 20, 2005 (EP) ..................... 05292203

(51) Int. Cl.
*C07D 241/36* (2006.01)
(52) U.S. Cl. ...................................... 544/342
(58) Field of Classification Search .............. 544/342
See application file for complete search history.

(56) References Cited

FOREIGN PATENT DOCUMENTS
EP 1471068 10/2004

OTHER PUBLICATIONS

Wright, A. E. et al. J Org. Chem. 1990, 55; 4508-4512.
Rinehart, K. L. et al. J. Org. Chem. 1990, 55; 4512-4515.
Rinehart, K. L. et al. J Org. Chem. 1991, 56; 1676.
Sakai, R. et al. Proc. Nat. Acad Sci. USA. 1992, 89; 11456-11460.
Sakai, R. et al. J. Am. Chem. Soc. 1996, 118; 9017-9023.
Suwanborirux, K. et al. J. Nat Prod. 2002, 65; 935-937.
Rinehart, K. L. Med. Research. Reviews. 2000, 1-27.
Pommier, Y. et al. Biochemistry 1996, 35; 13303-13309.
Moore, B. M. et al. Am. Chem. Soc. 1998, 120; 2490-2491.
Zewail-Foote, M. et al. J Am. Chem. Soc. 2001, 123; 6485-6495.
Moore, B. M. et al. J Am. Chem. Soc. 1997, 119; 5475-5476.
Zewail-Foote, et al. J Med Chem. 1999, 42; 2493-2497.
Garcia-Nieto, R. et al. J. Med. Chem. 2000, 43; 4367-4369.
Garcia-Nieto, R. et al. J. Am. Chem. Soc. 2000, 122; 7172-71 82.
Seaman, F. C. et al. J. Am. Chem. Soc. 1998, 120; 13028-13041.
Takebayashi, Y. et al. Nature Med. 2001, 7; 961-966.
Zewail-Foote, M. et al. Chem. Biol. 2001,8; 1033-1049.
Jin, S. et al. Proc. Nat. Acad. Sci, U.S.A. 2000, 97; 6775-6779.
Minuzzo, M. et al. Proc. Nat. Acad Sci. USA. 2000, 97; 6780-6784.
Arai, T. et al. J. AntBiot. 1977, 30; 1015-1018.
Arai, T. et al. The Alkaloids Brossi, A. Ed.; Academic Press: New York, 1983, V 21, pp. 55 100.
Itoh, J. et al. Antibiot. 1982, 35; 642-644.
He, H. et al. Tetrahedron Lett. 2000, 41; 2067-2071.
Scott, J. D. et al. Chem. Rev. 2002, 102; 1669-1730.
E.J. Corey et al.J Am. Chem. Soc. 1996, 118; 9202-9203.
Martinez et al, Org Lett 2000,2; 993-996.
Endo et al, T. Synlett 1999, 1103-1105.

(Continued)

*Primary Examiner* — James O Wilson
*Assistant Examiner* — Douglas M Willis
(74) *Attorney, Agent, or Firm* — Lerner, David, Littenberg, Krumholz & Mentlik, LLP

(57) ABSTRACT

The present invention concerns an intermediate of the following formula (I) in which $R_1$ and $R_2$ represent independently of each other a $C_1$-$C_{12}$ alkyl group, a ($C_1$-$C_{12}$ alkoxy)carbonyl group, optionally substituted by one, two or three halogen atom, a ($C_2$-$C_{12}$ alkenyloxy)carbonyl group, an acyl group, a aryl($C_1$-$C_{12}$)alkyl group, an arylalkoxy carbonyl group, a ($C_1$-$C_{12}$ alkyl)sulfonyl group or an arylsulfonyl group, $R_3$ represents a O-protecting group, $R_4$ and $R_5$ represent independently of each other a hydrogen atom or a O-protecting group, $R_6$ represent a O-protecting group and $R_7$ represent a $C_1$-$C_{12}$ alkyl group or —$OR_6$ and —$OR_7$ form together a group —$OCH_2O$—. The present invention concerns also a process of preparation of the intermediate and its use for the preparation of Ecteinascidin 743 and Ecteinascidin-770.

(I)

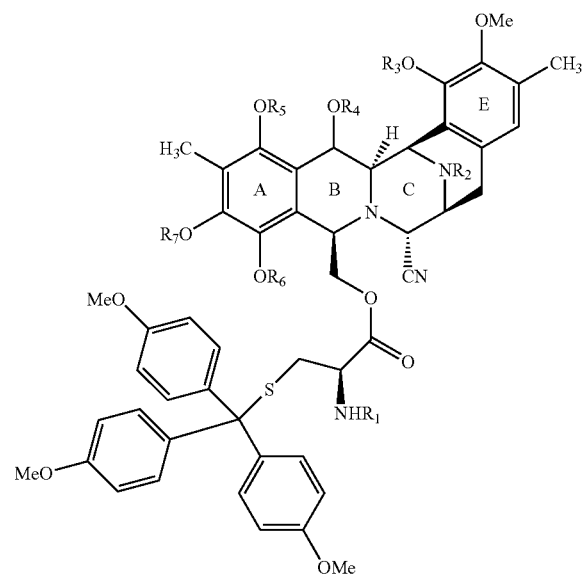

7 Claims, No Drawings

OTHER PUBLICATIONS

Cuevas Carmen et al, Org. Lett. 2000, 2; 2545-2548.
Menchaca et al, J Org. Chem. 2003, 68; 8859-8866.
Kubo et al, J Chem. Soc. Perkin Trans 1 1997, 53-69.
Saito et al, Heterocycles 1999, 51; n°1, 9-12.
Kubo et al, A.Chem. Pharm. Bull. 2000, 48; 1549-1557.
Zhou et al, Tetrahedron Lett. 2000, 41; 2039-2042.
Zhou et al Tetrahedron Lett. 2000, 41; 2043-2046.
Zhou et at Org Lett 2002, 4; 43-46.
Danishefsky et al Chem. Int Ed. 2006, 45; 1754-1759.
Williams et al, Tetrahedron Lett. 2001, 42; 543-546.
Wei Jin et al, Tetrahedron Lett. 2003, 44; 4635-4639.
Wei Jin et al, Org. Lett 2003, 5; 2095-2098.
Magnus et al Org Len, 2003, 5; 2181-2184.
Tang et al, Tetrahedron Lett. 2003, 44; 7091-7094.
Corey and Schreiber, Proc. Nat. Acad. Sci U.S.A. 1996, 96; 3496-3501.
De Paolis, M. et al, Chem. Soc. Chem. Commun. 2003, 2896-2897.
De Paolis, M. et al. Synlett 2004, N°4; 729-731.
Chen, X. et al. J Org Chem. 2005, 70;, 4397-4408.
Bobbit, J. M. et al. J Org. Chem. 1965, 30; 2247-2250.
Miyaura et al, Chem. Rev. 1995, 95; 2457-2483.
Neuville, L. et al. J Org. Chem. 1999, 64; 7638-7642.
F. Guibé, Tetrahedron 1998, 54; 2967-3042.
Cox, E. D. et al. Chem. Rev. 1995 ,95; 1797-1842.
Kubo et al, J Chem. Soc. Perkin Trans 1 1997, 53-69.
Wei Jin et al, Org. Lett 2003, 5; 2095-2098.
Corey et al, J Am. Chem. Soc. 1997, 119;12414-12415.
Trost, B. M. et al. J Org Chem. 1994, 59; 4202-4205.
Helmchen, G et al. Tetrahedron Lett. 1972, 3873-3878 (only in German).
Garner et al, J Org Chem. 1987, 52;2361-2364.
Garner et al, J Org. Chem. 1988, 53; 2979-2984.
Garner et al, J Org. Chem. 1988, 53; 4395-4398.
Van DeWater, R. W Tetrahedron 2002, 58; 5367-5405.
Petasis, N. A. Multicomponent Reactions with Organoboron Compounds in Multicomponent Reactions; Zhu, J. ci al., Eds.; Wiley-VCH, Weinheim, 2005, 199-223.
Endo Atsuchi et al: "Total synthesis of cctcinascidin 743", Journal of the American Chemical society, 2002 124(23); 6552-6554.
Chen et al: "Total Synthesis of ecteinascidin 743", Journal of the American Chemical society, Jan. 2006, 128(I): 87-89.

INTERMEDIATE AND PROCESS OF PREPARATION OF ECTEINASCIDIN SUCH AS ECTEINASCIDINES-583,597 USING SUCH INTERMEDIATE

BACKGROUND OF THE INVENTION

The ecteinascidins, a family of tetrahydroisoquinoline alkaloids isolated from the Caribbean tunicate *Ecteinascidia turbinate*, (Wright, A. E. et al. *J. Org. Chem.* 1990, 55, 4508-4512; Rinehart, K. L. et al. *J. Org. Chem.* 1990, 55, 4512-4515; Rinehart, K. L. et al. *J. Org. Chem.* 1991, 56, 1676; Sakai, R. et al. *Proc. Nat. Acad. Sci. U.S.A.* 1992, 89, 11456-11460; Sakai, R. et al. *J. Am. Chem. Soc.* 1996, 118, 9017-9023; Suwanborirux, K. et al. *J Nat. Prod.* 2002, 65, 935-937) possess potent cytotoxic activity against a variety of tumor cell lines in vitro and against several rodent tumors and human tumor xenografts in vivo (Rinehart, K. L. *Med. Drug. Rev.* 2000, 1-27). One of its members, ecteinascidin 743 (Et 743, 1a, below) is currently in phase II/III clinical trials in Europe and the United States for ovarian, endometrium, breast cancer and several types of sarcoma. It showed particularly high activity in cases of advanced sarcoma that had relapsed or were resistant to conventional therapy. Et 743 (commercial name: Yondelis®) has been granted Orphan Drug Designation by the US Food and Drug Administration (FDA, 2005) and European Commission (2003) for the treatment of ovarian cancer. The antiproliferative activity of Et 743 is greater than that of taxol, camptothecin, adriamycin, mitomycin C, cisplatin, bleomycin and etoposide by 1-3 orders of magnitude. Et 743 binds to the minor groove of the DNA by way of three hydrogen bond contacts between the A- and E-ring of Et 743 and the three base pairs recognition sequence, the most critical being the interaction of the E-subunit with the base located 3' to the modification site. In addition, through intramolecular acid-catalyzed dehydration of the carbinolamine moiety, Et 743 forms a covalent bond with the exocyclic 2-amino group of guanine (Pommier, Y. et al. *Biochemistry* 1996, 35, 13303-13309; Moore, B. M. et al. *Am. Chem. Soc.* 1998, 120, 2490-2491). It was demonstrated that the formation of Et 743/DNA complex is reversible under non-denaturing conditions and that Et 743 can migrate from the non-favored bonding sequence (e.g., 5'-AGT) to the favored DNA target site (e.g., 5'-AGC), leading to the observed site-specificity (Zewail-Foote, M. et al. *J. Am. Chem. Soc.* 2001, 123, 6485-6495). In the Et 743/DNA adduct, the double helix bends toward the major groove and the third domain (ring F-G) of Et 743 positions itself outside the complex, making it available to interact with proteins and at the same time disrupting DNA-protein binding (Moore, B. M. et al. *J. Am. Chem. Soc.* 1997, 119, 5475-5476; Zewail-Foote, et al. *J. Med. Chem.* 1999, 42, 2493-2497; Garcia-Nieto, R. et al. *J. Med. Chem.* 2000, 43, 4367-4369; Garcia-Nieto, R. et al. *J. Am. Chem. Soc.* 2000, 122, 7172-7182; Seaman, F. C. et al. *J. Am. Chem. Soc.* 1998, 120, 13028-13041 Takebyashi, Y. et al. *Nature Med.* 2001, 7, 961-966; Zewail-Foote, M. et al. *Chem. Biol.* 2001, 8, 1033-1049). Although the F-G subunit has little contact with the minor groove of DNA, its presence is of utmost importance for the antitumor activity of Et 743. Indeed, it has been shown that modifying the F-G subunit changes the drug's ability to inhibit cell division. For example, Et 736 (1c) with a tetrahydro-β-carboline residue instead of a tetrahydroisoquinoline at the F-G part has different bioactivity profile relative to Et 743. It is only slightly active vs M5076 ovarian sarcoma and an MX-1 human mammary carcinoma xenograft, but shows a higher level of activity in vivo in mice against P388 leukemia (Sakai, R. et al. *Proc. Nat. Acad. Sci. U.S.A.* 1992, 89, 11456-11460; Jin, S. et al. *Proc. Nat. Acad. Sci. U.S.A.* 2000, 97, 6775-6779; Minuzzo, M. et al. *Proc. Nat. Acad. Sci. U.S.A.* 2000, 97, 6780-6784). The Et 637 (1e) and Et 594 (1f), lacking the F-G subunit, are generally 10-50 times less active than Et 743 against MEL 28 and CV-A cell lines (Sakai, R. et al. *J. Am. Chem. Soc.* 1996, 118, 9017-9023).

Structurally, Et 743 is constituted of three tetrahydroisoquinoline systems interconnected via two bridged ring systems. Specifically, ring A-B and ring D-E are fused together producing an additional 6-membered ring (ring C) and a labile carbinolamine functional group that serves to alkylate the DNA. In addition, ring A-B is linked to the third tetrahydroisoquinoline (F-G) by a 10-membered lactone having a 1,4-bridged benzylic sulfide linkage. Overall seven stereocenters and eight rings are found in Et-743. Et 743 is structurally related to the saframycin class of antibiotics (Arai, T. et al. *J. Antibiot.* 1977, 30, 1015-1018; Arai, T. et al. *The Alkaloids* Brossi, A. Ed.; Academic Press: New York, 1983, V 21, pp 55-100), the noticeable difference being the higher oxidation state of C-4 carbon in Et 743 than in saframycin (2, 3). The same difference can be recognized in two other structurally related natural products, naphthyridinomycin (4) (Itoh, J. et al. *Antibiot.* 1982, 35, 642-644) and lemonomycin (5, Structures of ecteinascidin 743 and related natural products, provided below.) (He, H. et al. *Tetrahedron Lett.* 2000, 41, 2067-2071).

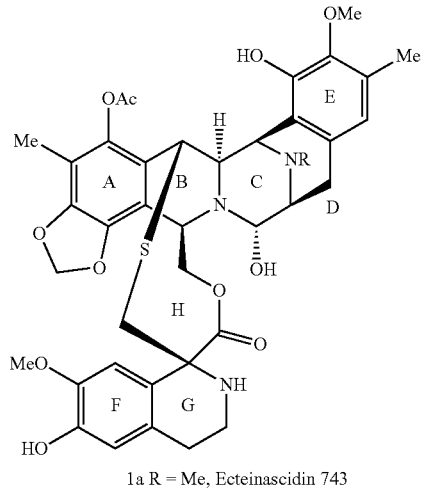

1a R = Me, Ecteinascidin 743
1b R = H, Ecteinascidin 729

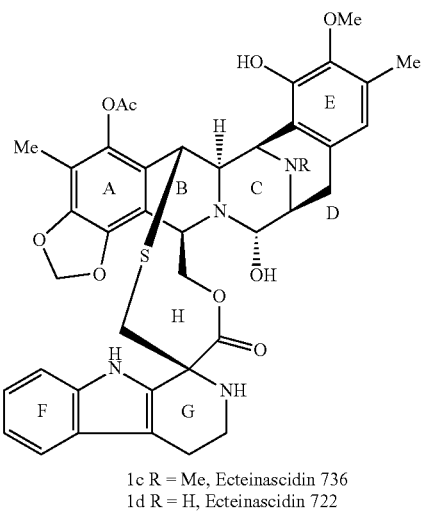

1c R = Me, Ecteinascidin 736
1d R = H, Ecteinascidin 722

-continued

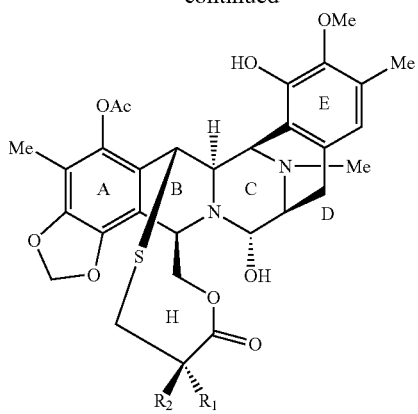

1e R₁ = H, R₂ = NHAc, Ecteinascidin 637
1f R₁, R₂ = O, Ecteinascidin 594

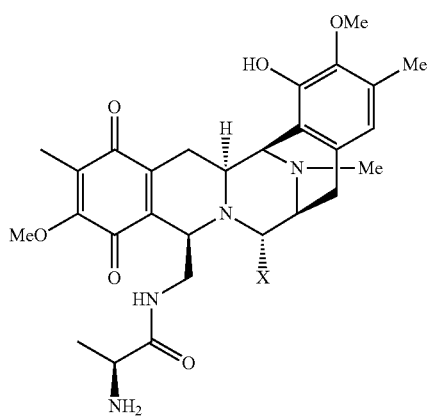

2 Safracin B X = OH
3 Cyanosaframycin B X = CN

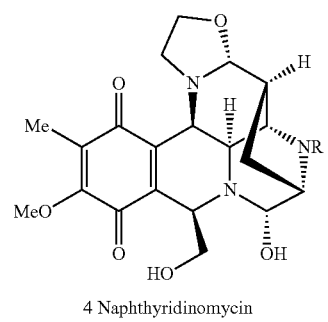

4 Naphthyridinomycin

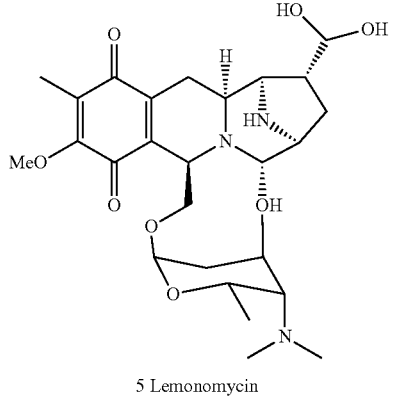

5 Lemonomycin

-continued

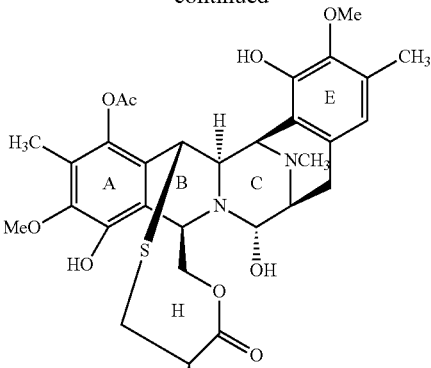

1g ecteinascidin 597

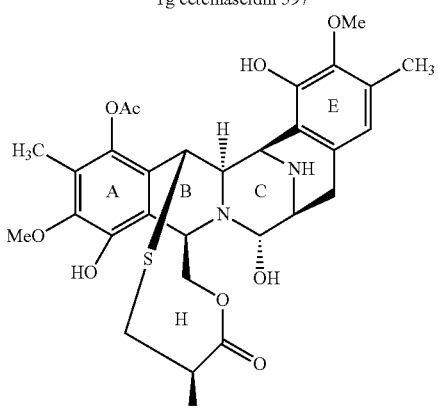

1h ecteinascidin 583

Due to the extremely low natural availability (1 gram from 1 ton of tunicate), the drug supply is becoming a key issue. PharmaMar has tried growing the sea squirt on underwater farms (300 tonnes) in Puerto Rico and Spain but only with limited success. To obtain enough amount of drug for cancer treatment, a simpler and more efficient process was thus needed. Total synthesis or hemisynthesis from simpler natural product became an important alternative and, in this particular case probably the only available alternative (Scott, J. D. et al. *Chem. Rev.* 2002, 102, 1669-1730).

To date, two total syntheses have been accomplished by Corey (*J. Am. Chem. Soc.* 1996, 118, 9202-9203; *Org. Lett.* 2000, 2, 993-996) and Fukuyama (T. *Synlett* 1999, 1103-1105; *J. Am. Chem. Soc.* 2002, 124, 6552-6554) respectively. A semi synthesis from cyanosaframycin B (3) has been developed by Cuevas, Manzanares and co-workers at PharmaMar (*Org. Lett.* 2000, 2, 2545-2548; *J. Org. Chem.* 2003, 68, 8859-8866). In addition, other synthetic approaches have been reported from a number of research groups, including that of Kubo (*J. Chem. Soc. Perkin Trans* 1 1997, 53-69; *Heterocycles* 1999, 51, 9-12; A. *Chem. Pharm. Bull.* 2000, 48, 1549-1557), Danishefsky (*Tetrahedron Lett.* 2000, 41, 2039-2042; *Tetrahedron Lett.* 2000, 41, 2043-2046; *Org. Lett.* 2002, 4, 43-46; *Chem. Int. Ed.* 2006, 45, 1754-1759), Williams (*Tetrahedron Lett.* 2001, 42, 543-546; *Tetrahedron Lett.* 2003, 44, 4635-4639; *Org. Lett.* 2003, 5, 2095-2098), Magnus (*Org. Lett.* 2003, 5, 2181-2184) and Liu (*Tetrahedron Lett.* 2003, 44, 7091-7094). A simpler synthetic analog of Et 743 named phthalascidin (Pt-650) that displayed virtually the same biological activities as the natural product has been discovered by Corey and Schreiber (*Proc. Natl. Acad. Sci. U.S.A.* 1996, 96, 3496-3501).

While both Corey and Fukuyama's syntheses are landmark achievement in organic synthesis, they are difficult to be applied into a large-scale production.

An alternative synthetic approach has been investigated and preliminary result has been published dealing with the synthesis of pentacyclic compound of Et 743 (De Paolis, M. et al. *Chem. Soc. Chem. Commun.* 2003, 2896-2897; De Paolis, M. et al. *Synlett* 2004, 729-731; Chen, X. et al. *J. Org. Chem.* 2005, 70, 4397-4408).

BRIEF SUMMARY OF THE INVENTION

Surprisingly, the present inventors have discovered a new and original synthesis of Et 637 and its conversion to Et-743 that is highly practical and applicable to large scale production of the drug. Such process comprises 31 longest linear steps with 1.7% overall yields from 3-methyl catechol. This synthesis is highly convergent and has been carried out on multigram scale. Furthermore, the discovered total synthesis is more efficient than the previous ones (Corey's synthesis: 35 longest linear steps from sesamol, overall yields: 0.72%; Fukuyama's synthesis: 50 longest linear steps from 3-methyl catechol, overall yields: 0.61%) and provides an attractive alternative to the PharmaMar's semi synthesis (21 steps started from cyanosaframycin in 1% overall yield). Furthermore the present inventors have also discovered a new and original synthesis of Et 597 and Et 583, biosynthetic precursors of Et 743 and other Et members In particular the new key intermediate of the following formula I

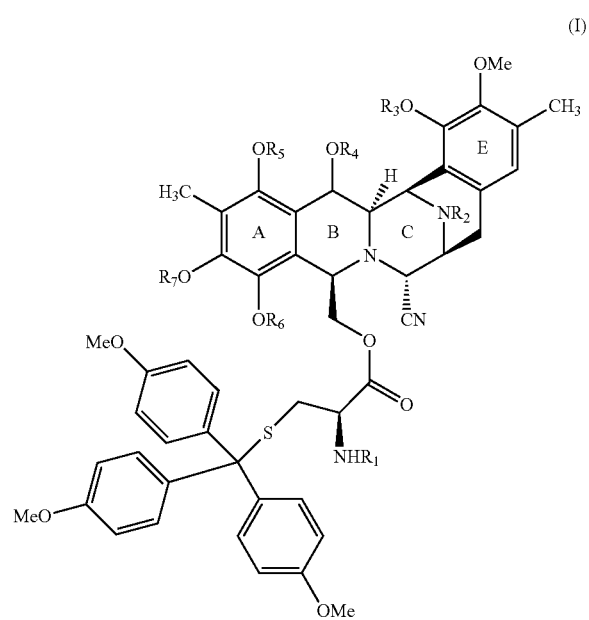

in which $R_1$ and $R_2$ represent independently of each other a $C_1$-$C_{12}$ alkyl group, a ($C_1$-$C_{12}$ alkoxy)carbonyl group, optionally substituted by one, two or three halogen atom, a ($C_2$-$C_{12}$ alkenyloxy)carbonyl group, an acyl group, a aryl($C_1$-$C_{12}$) alkyl group, an arylalkoxy carbonyl group, a ($C_1$-$C_{12}$ alkyl) sulfonyl group or an arylsulfonyl group, $R_3$ represents a O-protecting group, $R_4$ and $R_5$ represent independently of each other a hydrogen atom or a O-protecting group, $R_6$ represent a O-protecting group and $R_7$ represent a $C_1$-$C_{12}$ alkyl group or —$OR_6$ and —$OR_7$ form together a group —$OCH_2O$—;

allow the reduction of the number of steps involved in the present process, since its conversion in the compound of the following formula

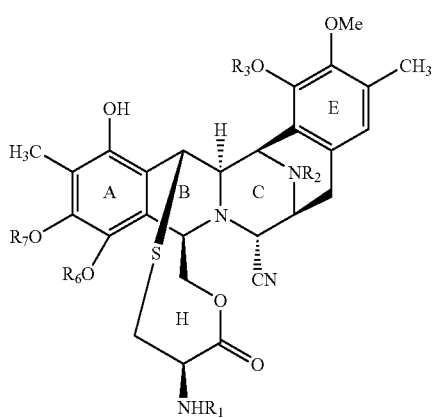

in which $R_1$, $R_2$, $R_3$, $R_6$ and $R_7$ have the same meaning as in formula I, necessitates only the use of a single simple step or of only two steps, in which, at the same time or successively the

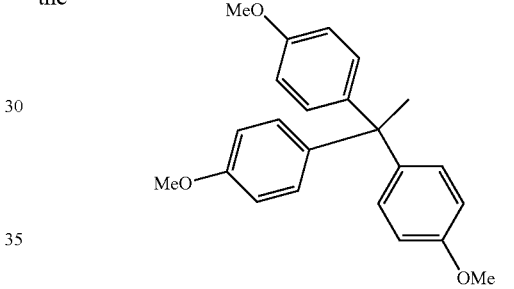

group is removed and a new cycle H is formed.

Therefore, the present invention concerns an Intermediate of the following formula

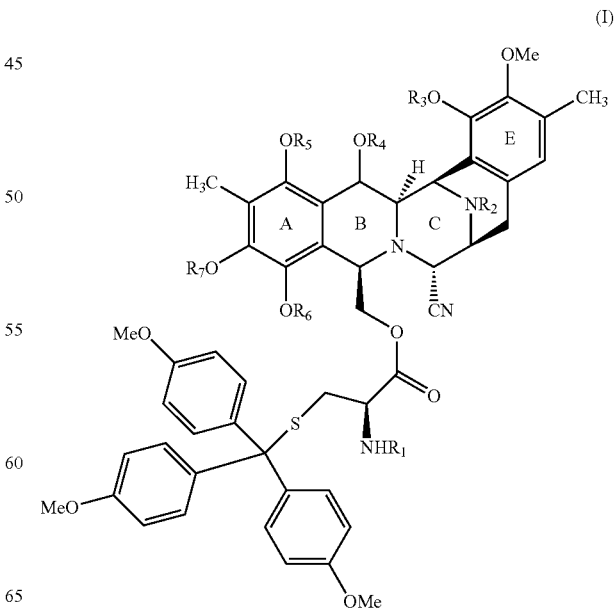

in which $R_1$ and $R_2$ represent independently of each other a $C_1$-$C_{12}$ alkyl group, a ($C_1$-$C_{12}$ alkoxy)carbonyl group, optionally substituted by one, two or three halogen atom, a ($C_2$-$C_{12}$ alkenyloxy)carbonyl group, an acyl group, a aryl($C_1$-$C_{12}$) alkyl group, an arylalkoxy carbonyl group, a ($C_1$-$C_{12}$ alkyl) sulfonyl group or an arylsulfonyl group, $R_3$ represents a O-protecting group, $R_4$ and $R_5$ represent independently of each other a hydrogen atom or a O-protecting group, $R_6$ represent a O-protecting group and $R_7$ represent a $C_1$-$C_{12}$ alkyl group or —$OR_6$ and —$OR_7$ form together a group —$OCH_2O$—.

DETAILED DESCRIPTION OF THE INVENTION

The term "($C_1$-$C_{12}$)alkyl" as used in the present invention refers to any linear or branched saturated hydrocarbon radical having from one to 12 carbon atoms, including, but not limited to, methyl, ethyl, n-propyl, iso-propyl, n-butyl, iso-butyl, sec-butyl, t-butyl, n-pentyl, n-hexyl and the like.

The term "($C_1$-$C_{12}$)alkoxycarbonyl" as used in the present invention refers to any —(C=O)—O—R radical wherein R is a ($C_1$-$C_{12}$)alkyl as defined above including, but not limited to ethoxycarbonyl, methoxycarbonyl, t-butyloxycarbonyl (t-BOC).

The term "$C_2$-$C_{12}$ alkenyl" as used in the present invention refers to any linear or branched chain alkenyl radicals containing from 1 to 12 carbon atoms including, but not limited to, ethenyl, propenyl, butenyl, pentenyl, hexenyl and the like.

The term "($C_1$-$C_{12}$)alkenyloxycarbonyl" as used in the present invention refers to any —(C=O)—O—R radical wherein R is a ($C_1$-$C_{12}$)alkenyl as defined above.

The term "aryl" as used in the present invention refers to a monocyclic or bicyclic carbocyclic ring system having one or more aromatic rings including, but not limited to, phenyl, naphthyl, tetrahydronaphthyl, indanyl and the like, in particular phenyl.

The term "aryl($C_1$-$C_{12}$)alkyl" as used in the present invention refers to any aryl group such as defined above linked to a $C_1$-$C_{12}$ alkyl radical such as defined above, for example, benzyl and the like.

The term "arylalkoxycarbonyl" as used in the present invention refers to any —(C=O)—O—R—Ar radical wherein R is a ($C_1$-$C_{12}$)alkyl as defined above and Ar is an aryl as defined above, including, but not limited to benzyloxycarbonyl (Cbz).

The term "($C_1$-$C_{12}$)alkylsulfonyl" as used in the present invention refers to any $SO_2$—R radical, wherein R is a ($C_1$-$C_{12}$)alkyl as defined above.

The term "arylsulfonyl" as used in the present invention refers to any $SO_2$—Ar radical, wherein Ar is an aryl as defined above.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise substituted methyl ethers, for example, methoxymethyl (MOM), benzyloxymethyl, 2-methoxyethoxymethyl, 2-(trimethylsilyl)ethoxymethyl, t-butyl, benzyl and triphenylmethyl, tetrahydropyranyl ethers, substituted ethyl ethers, for example, 2,2,2-trichloroethyl, silyl ethers, for example, trimethylsilyl, t-butyldimethylsilyl (TBS) and t-butyldiphenylsilyl; and esters prepared by reacting the hydroxyl group with a carboxylic acid for example, acetate, propionate, benzoate and the like. In particular an allyl or an acetyl group is a "O-Protecting group" according to the present invention.

Advantageously the Intermediate according to the present invention, has the following formula (I bis)

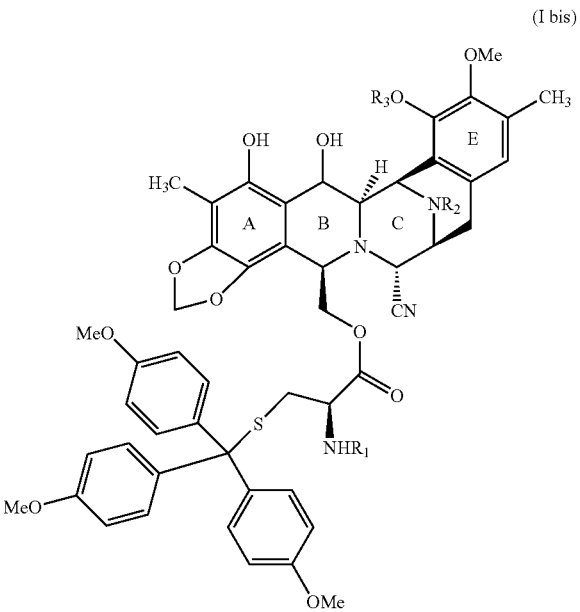

(I bis)

in which $R_1$, $R_2$ and $R_3$ have the same meaning as in formula (I).

In another advantageously embodiment $R_4$, $R_5$ and $R_6$ represent independently of each other a O-protecting group and $R_7$ represent a $C_1$-$C_{12}$ alkyl group, advantageously a methyl group. More advantageously $R_4$ and $R_5$ represent a MOM group, $R_6$ represent an allyl group and $R_7$ represent a methyl group.

In this case, advantageously the Intermediate according to the present invention has the following formula I ter:

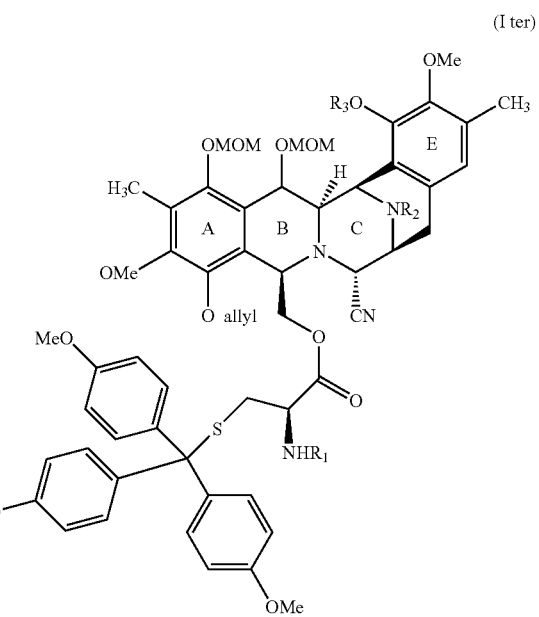

(I ter)

Advantageously $R_1$ represents a Troc group or an acyl group, more advantageously a Troc group. Advantageously $R_2$ represents an Alloc group or a Troc group, more advantageously an Alloc group. Advantageously $R_3$ represents an allyl group. More advantageously $R_1$ represents a Troc group, $R_2$ represents an Alloc group and $R_3$ represents an allyl group.

The present invention furthermore concerns a process of preparation of a compound of formula I according to the present invention which comprises the step (p) of coupling of the compound of the following formula II

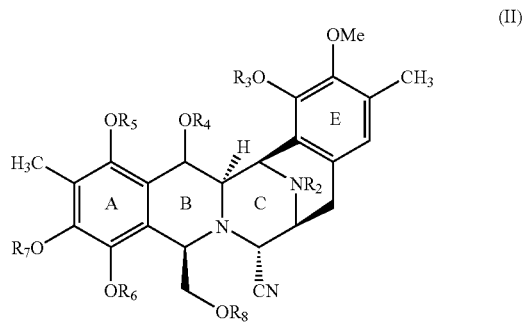

(II)

in which $R_2$, $R_3$, $R_4$, $R_5$, $R_6$ and $R_7$ have the same meaning as in formula I and $R_8$ represents H with the compound (R)—N—$R_1$—(S-4,4',4''-trimethoxyltrityl) Cys in which $R_1$ has the same meaning as in formula I, advantageously under standard conditions. In case where $R_1$ represents a Troc group, (R)—N-Troc-(S-4,4',4''-trimethoxyltrityl) Cys can be synthesized from commercial available (R)—S-trityl Cys in three-steps in 76% overall yield as follow: a) TrocCl, NaHCO$_3$, H$_2$O/1,4-dioxane, 45° C.; b) Et$_3$SiH, acid trifluoroacetic, CH$_2$Cl$_2$; and c) (p-4-MeOPh)$_3$CCl, CH$_2$Cl$_2$)

Advantageously in case where $R_1$ represents a Troc group, and more advantageously in case where $R_2$ represents an Alloc group and $R_3$ represents an allyl group, the conditions of step (p) are as follow: N-(3-dimethylaminopropyl)-N-ethyl carbodiimide (EDCI), 4-dimethylaminopyridine (DMAP), CH$_2$Cl$_2$, room temperature.

Advantageously in the case where $R_6$ represents a O-protecting group, more advantageously an allyl group, the process according to the present invention comprises a prior step (p1) of preparation of the compound of formula II in which $R_6$ represents a O-protecting group by the protection of the hydroxyl group with a O-protecting group $R_6$ of the compound of the following formula II bis

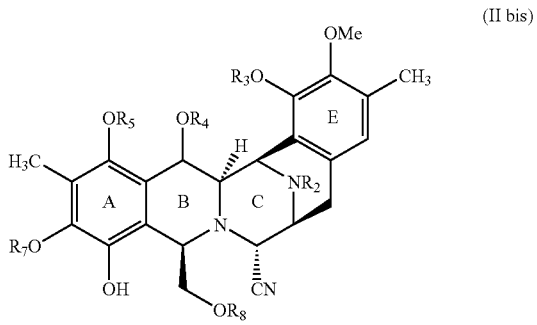

(II bis)

in which $R_2$, $R_3$, $R_4$, $R_5$, $R_7$ and $R_8$ have the same meaning as in formula I.

Advantageously in the case where $R_6$ represent an allyl group, the conditions of steps (p1) are as follow: allyl bromide, K$_2$CO$_3$ in acetonitrile at room temperature.

Advantageously, the process according to the present invention comprises a prior step (o) of preparation of the compound of formula II in which $R_6$ does not represent a O-protecting group or of the compound of formula II bis by removal of the O-protecting group $R_8$ of a compound of formula II or of the formula II bis in which $R_3$, $R_4$, $R_5$, $R_7$ and $R_2$ have the same meaning as above, $R_6$ has the same meaning as above and does not represent a O-protecting group and $R_8$ is different from $R_3$, $R_4$ and $R_5$ and represents a O-protecting group advantageously an acetyl group or a Troc group.

Therefore, in the case where $R_8$ represents an acetyl group, step (o) is a saponification, in particular with the following conditions: K$_2$CO$_3$ in MeOH at room temperature.

In the case where $R_8$ represents a Troc group, the conditions of step (o) are as follow: Zn, AcOH, Et$_2$O at room temperature.

More advantageously, the process according to the present invention comprises a prior step (n) of preparation of the compound of formula II in which —O$R_6$ and —O$R_7$ form together a group —OCH$_2$O—, $R_4$ and $R_5$ represent a hydrogen atom, $R_2$ and $R_3$ have the same meaning as above and $R_8$ is different from $R_3$ and represents a O-protecting group by a Pomerantz-Fritsch type cyclization (Bobbit, J. M. et al. *J. Org. Chem.* 1965, 30, 2247-2250) under acidic conditions, in particular with trifluoroacetic acid (TFA) in dichloromethane, with concomitant removal of the O-protecting group $R_9$, of the compound of the following formula III

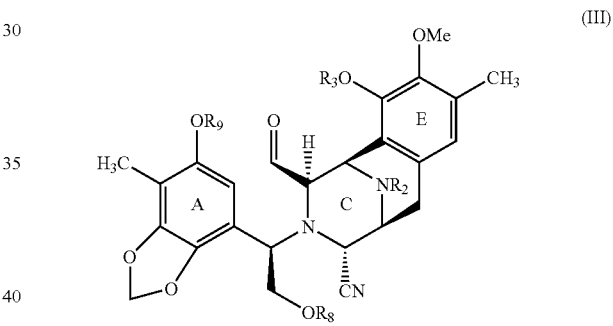

(III)

in which $R_2$ and $R_3$ have the same meaning as in formula II, $R_8$ is different from $R_3$ and represents a O-protecting group, advantageously an acetyl group and $R_9$ is different from $R_3$ and $R_4$ and represents a O-protecting group, advantageously MOM.

The process according to the present invention can comprises a prior step (l,m) of preparation of the compound of formula III by the removal of the O-protecting group $R_{10}$ of the compound of the following formula IV

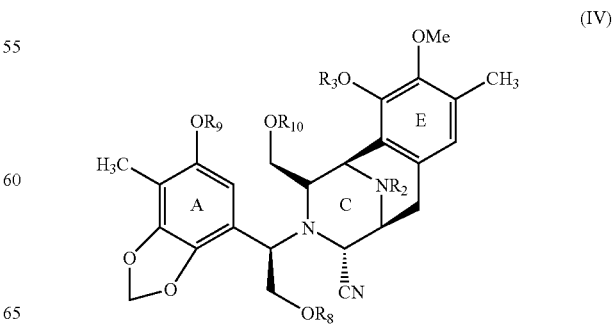

(IV)

in which $R_2$, $R_3$, $R_8$ and $R_9$ have the same meaning as in formula III and $R_{10}$ is different from $R_3$, $R_8$ and $R_9$ and represents a O-protecting group, advantageously a TBS group, and the oxidation of the deprotected hydroxyl group thus obtained, advantageously with a Dess-Martin reagent, more advantageously at room temperature.

In case where $R_{10}$ represents a TBS group, the removal of the O-protecting group $R_{10}$ consists in a desilylation, advantageously with the following conditions: $HF.H_2O$, MeCN at room temperature.

In another embodiment of the present invention, the process according to the present invention comprises a prior step (j,k) of preparation of the compound of formula IV by the reduction of the $YR_{11}$ group to alcohol of the compound of the following formula V

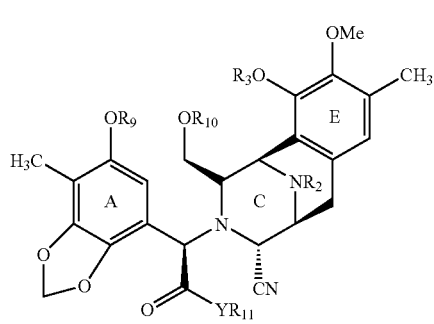

(V)

in which $R_2$, $R_3$, $R_9$ and $R_{10}$ have the same meaning as in formula IV, Y represents a oxygen atom, NH or a sulphur atom, advantageously a oxygen atom, and $R_{11}$ represents a $C_1$-$C_6$ alkyl group, advantageously an ethyl group, and the protection of the hydroxyl group obtained with a O-protecting group $R_8$ which has the same meaning as in formula IV.

Advantageously, $YR_{11}$ represents a O-ethyl group. In this case the conditions of the reduction reaction may be as follow: $LiBH_4$ in MeOH and THF at 0° C. to room temperature.

In case where $R_8$ represents an acetyl group, the protection of the hydroxyl group obtained with the O-protecting group $R_8$ is an acetylation, advantageously with the following conditions: $Ac_2O$, Pyridine (Py) and DMAP in $CH_2Cl_2$.

In an advantageous embodiment of the present invention, the process according to the present invention comprises a prior step (i) of preparation of the compound of formula V by oxidation, advantageously using a Dess-Martin reagent, more advantageously at room temperature, of the hydroxyl group of the compound of the following formula VI

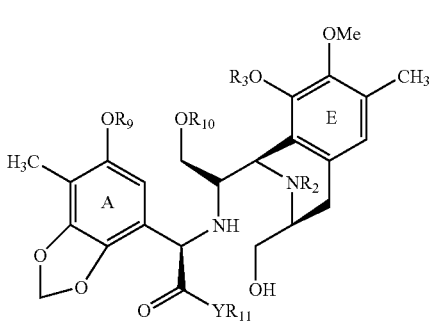

(VI)

in which $R_2$, $R_3$, $R_9$, $R_{10}$, Y and $R_{11}$ have the same meaning as in formula V and a zinc chloride-catalyzed Strecker reaction, advantageously using trimethylsilyl cyanide (TMSCN) and $ZnCl_2$.

In a particular embodiment of the present invention, the process according to the present invention comprises a prior step (g,h) of preparation of the compound of formula VI by protection with the O-protecting group $R_{10}$ which has the same meaning as in formula VI of the hydroxyl group of the compound of the following formula VII

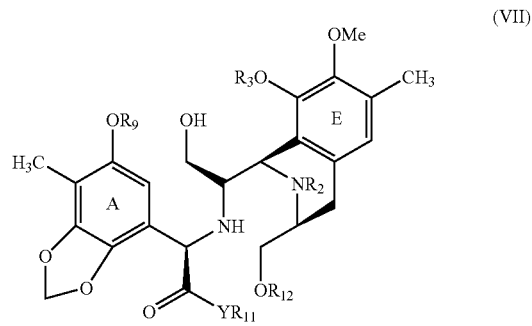

(VII)

in which $R_2$, $R_3$, $R_9$, Y and $R_{11}$ have the same meaning as in formula VI and $R_{12}$ is different from $R_3$, $R_9$ and $R_{10}$ and represents a O-protecting group, advantageously an acetyl group, and the removal of the O-protecting group $R_{12}$.

In case where $R_{12}$ represents an acetyl group, the removal of the O-protecting group $R_{12}$ consists in the hydrolysis of the acetate under mild basic conditions, in particular using $K_2CO_3$ in MeOH at room temperature.

In case where $R_{10}$ represents a TBS group, the protection with the O-protecting group $R_{10}$ can use the following conditions: TBSCl, imidazole, N,N-dimethyl formamide (DMF) at room temperature.

In another particular embodiment of the present invention, the process according to the present invention comprises a prior step (f) of preparation of the compound of formula VII by the diastereoselective N-alkylation of the chiral amino alcohol of the following formula IX

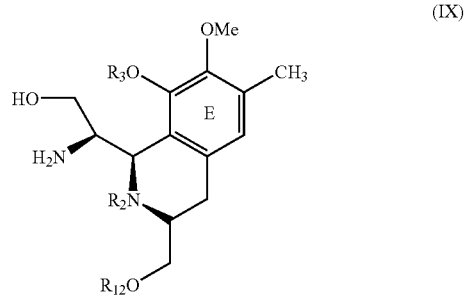

(IX)

in which $R_2$, $R_3$ and $R_{12}$ have the same meaning as in formula VII with a racemic benzyl halide of the following formula X

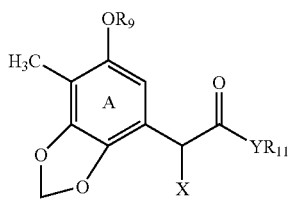
(X)

in which $R_9$, Y and $R_{11}$ have the same meaning as in formula VII and X represents a halogen atom, advantageously Br, advantageously using triethylamine (TEA) and MeCN and separation in particular by column chromatography of the compound of formula VII from its diastereoisomer of the following formula VIII

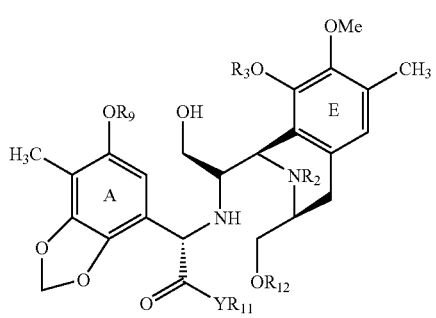
(VIII)

in which $R_2$, $R_3$, $R_9$, Y, $R_{11}$ and $R_{12}$ have the same meaning as in formula VII.

In a further particular embodiment of the present invention, the process according to the present invention comprises a prior step (e) of preparation of the compound of formula IX by treatment with TFA, advantageously at room temperature, of the compound of the following formula XI

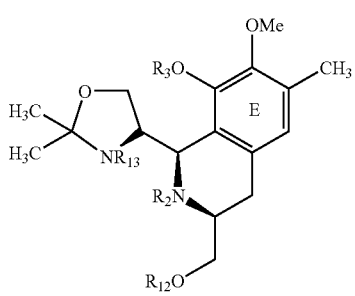
(XI)

in which $R_2$, $R_3$ and $R_{12}$ have the same meaning as in formula IX and $R_{13}$ is different from $R_2$ and represents a N-protecting group, advantageously a BOC group or by chemoselective hydrolysis, advantageously using $CeCl_3 \cdot 7H_2O$, MeCN and oxalic acid, more advantageously et room temperature during 3 hours, of the compound of formula XI in order to obtain a compound of the following formula XII

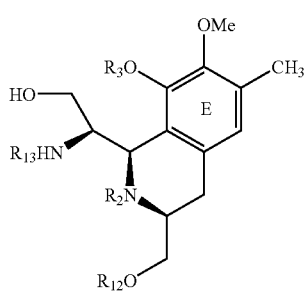
(XII)

in which $R_2$, $R_3$, $R_{12}$ and $R_{13}$ have the same meaning as in the above formula XI and removal of the N-protecting group $R_{13}$, advantageously, in case $R_{13}$ represents a BOC group, by using TFA/anisol in $CH_2Cl_2$, more advantageously at room temperature during 10 hours.

The term "N-protecting group" as used in the present invention refers to those groups intended to protect an amino group against undesirable reactions during synthetic procedures. Commonly used N-protecting groups are disclosed in Greene, "Protective Groups In Organic Synthesis," (John Wiley & Sons, New York (1981)). N-protecting groups comprise carbamates, amides, N-alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl, t-butyloxycarbonyl (BOC), benzyloxycarbonyl (Cbz), trichloroethoxycarbonyl (TROC), allyloxycarbonyl (Alloc), and the like.

In another advantageous embodiment of the present invention, the process according to the present invention comprises a prior step (b,c,d) of preparation of the compound of formula XI by protection of the hydroxyl groups and of the NH group with two different O-protecting groups $R_3$ and $R_{12}$ and a group $R_2$ which have the same meaning as in formula XI of the compound of the following formula XIII

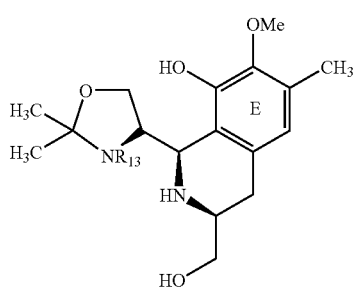
(XIII)

in which $R_{13}$ has the same meaning as in formula XI.

Advantageously, in case $R_2$ represents an Alloc group, the protection of the NH group with $R_2$ uses the following conditions: AllocCl, $NaHCO_3$ in $CH_2Cl_2$, more advantageously at room temperature during 2 hours.

Advantageously, in case $R_3$ represents an Allyl group, the protection of the hydroxyl group with $R_3$ uses the following conditions: AllylBr, $Cs_2CO_3$ in DMF, more advantageously at room temperature during 3 hours.

Advantageously, in case $R_{12}$ represents an acetyl group, the protection of the hydroxyl group with $R_{12}$ uses the following conditions: $Ac_2O$, Py in $CH_2Cl_2$, DMAP, more advantageously at room temperature during 1 hour.

In a further advantageous embodiment of the present invention, the process according to the present invention comprises a prior step (a) of preparation of the compound of formula XIII by condensation of the amino alcohol of the following formula 14

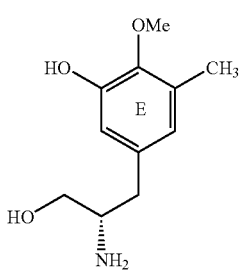

(14)

with the Garner's aldehyde of the following formula XV

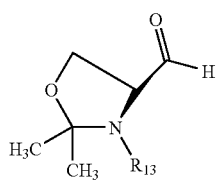

(XV)

in which $R_{13}$ has the same meaning as in formula XIII in the presence of molecular sieve, advantageously of 3 Å, under acidic conditions, advantageously AcOH in $CH_2Cl_2$, more advantageously at room temperature during 10 hours.

Advantageously the compound of formula X according to the present invention is obtained by the step (a) of conversion of the compound of the following formula XVIII

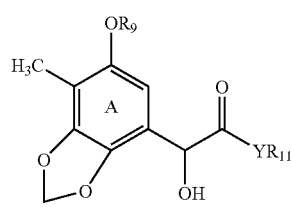

(XVIII)

in which $R_9$, Y and $R_{11}$ have the same meaning as in formula X, advantageously, in case X represents Br, by using $SOBr_2$ and benzyltriazole in $CH_2Cl_2$.

More advantageously the compound of formula XVIII according to the present invention is obtained by the step (β) of Suzuki-Miyaura cross-coupling (*Chem. Rev.* 1995, 95, 2457-2483) between trimethyl boroxine (TMB) and the compound of the following formula XIX

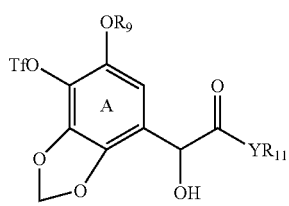

(XIX)

in which Y, $R_9$ and $R_{11}$ have the same meaning as in formula XVIII.

Advantageously this step uses the following conditions: TMB, $K_3PO_4$ with the catalyst $Pd[P(Ph)_3]_4$ in dioxane under reflux.

In particular the compound of formula XIX according to the present invention is obtained by the step (γ) of selective triflation using a 4-nitrophenyltriflate as sulfonylation agent (Neuville, L. et al. *J. Org. Chem.* 1999, 64, 7638-7642) of the compound of the following formula XX

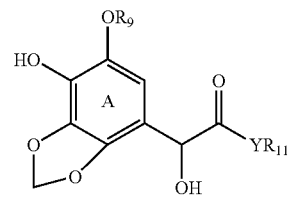

(XX)

in which Y, $R_9$ and $R_{11}$ have the same meaning as in formula XIX.

Advantageously, this step uses the following conditions: $K_2CO_3$ in DMF at room temperature.

More particularly, the compound of formula XX according to the present invention, in which Y represents a oxygen atom, is obtained by the step (δ) of hydroxyalkylation with $R_{11}$-glyoxalate in which $R_7$ has the same meaning as in formula XX of the compound of the following formula XXI

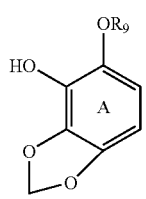

(XXI)

in which $R_9$ have the same meaning as in formula XX or the compound of formula XX according to the present invention, in which Y represents NH, is obtained by the step (δ1) of saponification of the compound of formula XX in which Y represents a oxygen atom and (δ2) coupling with an amine in presence of a coupling agent or the compound of formula XX according to the present invention, in which Y represents a sulphur atom, is obtained by the step (δ1) of saponification of the compound of formula XX in which Y represents a oxygen atom and (δ3) coupling with a thiol in presence of a coupling agent.

Advantageously the step (δ) uses the following conditions: LiCl in 1,1,1,3,3,3-hexafluoroisopropanol/toluene (¼) at room temperature.

In a more advantageously manner, in the above-described process according to the present invention, $R_1$ represents a Troc group, $R_2$ represents an Alloc group, $R_3$ represents an allyl group, $R_4$ represents an acetyl group, $R_5$ represents a MOM group, $R_6$ represents a TBS group and $R_8$ represents an acetyl group.

Advantageously, the present invention concerns the process of preparation of a compound of formula I which comprises the steps (f), (g, h), (i), (j, k), (l, m), (n), (o) and (p) as described above or the steps (a), (b, c, d), (e), (f), (g, h), (i), (j, k), (l, m), (n), (o) and (p) as described above or the steps (a), (b, c, d), (e), (f), (g, h), (i), (j, k), (l, m), (n), (o), (p), (α), (β), (γ), and (δ), optionally (δ1) and (δ2) or (δ1) and (δ3), as described above.

It concerns also a process of preparation of a compound of formula IX which comprises the steps (a), (b, c, d) and (e), as described above.

Furthermore, it concerns the step of preparation of a compound of formula X which comprises the steps ((α), (β), (γ), and (δ), optionally (δ1) and (δ2) or (δ1) and (δ3), as described above.

The present invention concerns furthermore the use of the intermediate of formula I according to the present invention for the preparation of the Ecteinascidin-743 of the following formula 1a

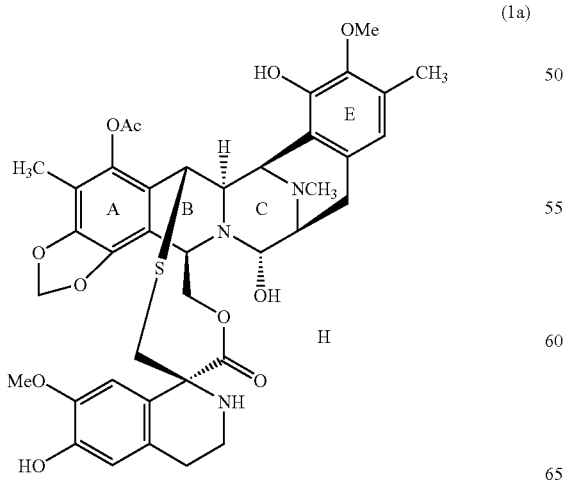

(1a)

or of the Ecteinascidin-770 of the following formula 57

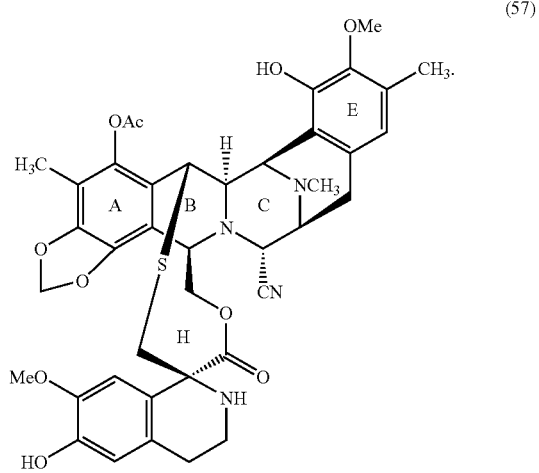

(57)

In particular the present invention concerns the process of preparation of the Ecteinascidin-743 of formula 1a which comprises the following steps:

q) dissolution of the compound of formula I according to the present invention in TFE containing 1% of TFA, advantageously at room temperature, and acetylation of the hydroxyl group in order to obtain the compound of formula XXII

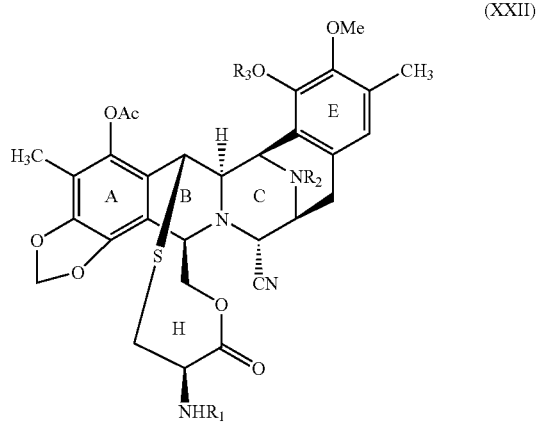

(XXII)

in which $R_1$, $R_2$ and $R_3$ have the same meaning as in formula I;

Advantageously the acetylation uses the following conditions: $Ac_2O$, Py in DMAP and $CH_2Cl_2$ at room temperature.

r) removal of the O-protecting group $R_3$ and of the group $R_2$, advantageously under Guibe's conditions (*Tetrahedron* 1998, 54, 2967-3042) followed by reductive N-methylation in order to obtain the compound of the following formula XXIII

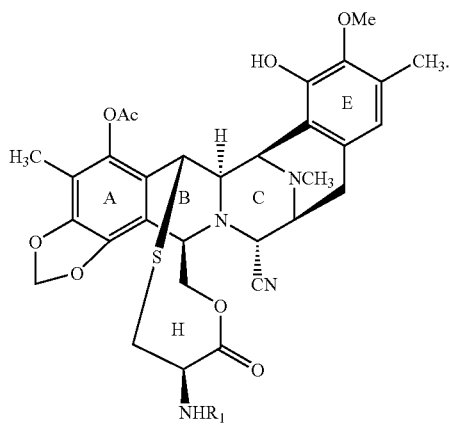

(XXIII)

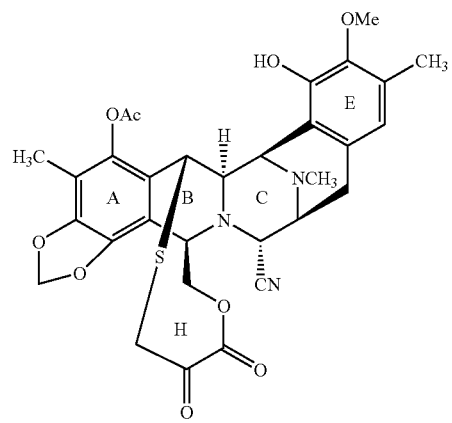

(55)

in which R₁ has the same meaning as in the above formula XXII;

Advantageously, the N-methylation uses the following conditions: NaBH₃CN in AcOH and HCHO at room temperature.

Advantageously, in case where $R_3$ represents an Allyl group and $R_2$ represents a Alloc group, the removal $R_2$ and $R_3$ uses the following conditions: n-Bu₃SnH with the catalyst PdCl₂(PPh₃)₂ in AcOH and CH₂Cl₂ at room temperature.

s) removal of the group $R_1$, in particular under reductive conditions, in order to obtain the compound of formula 54

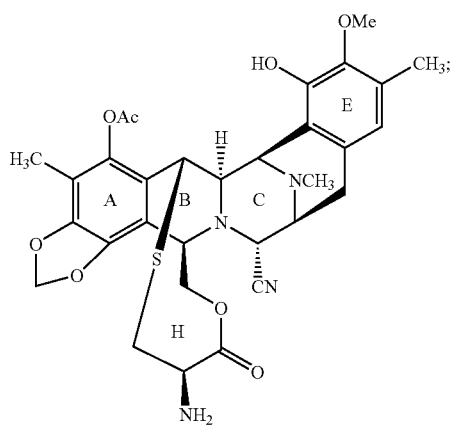

(54)

Advantageously, in case where $R_1$ represents a Troc group, the conditions are as follow: Zn in AcOH, advantageously at room temperature.

t) Oxidation, advantageously by using the following conditions: 4-formyl-1-methylpyridinium benzenesulfonate, 1,8-diazabicyclo[5,4,0]undec-7-ene (DBU), saturated oxalic acid, in DMF-CH₂Cl₂ at room temperature, of the compound of formula 54 in order to obtain the compound of the following formula 55 u) Pictet-Spengler reaction, advantageously using the following conditions: NaOAc in ETOH at room temperature, of the compound of formula 55 with 3-hydroxy-4-methoxyphenethyl amine in order to obtain the Ecteinascidin-770 of formula 57 (Suwanborirux, K. et al. *J. Nat. Prod.* 2002, 65, 935-937);

v) conversion of the Ecteinascidin-770 of formula 57 by treatment with a silver nitrate, advantageously using the following conditions: AgNO₃ in MeCN—H₂O at room temperature, in order to obtain the Ecteinascidin-743 of formula 1a.

Advantageously, the present invention concerns the process of preparation of Ecteinascidin-770 which comprises the steps (q), (r), (s), (t) and (u) as described above or the steps (f), (g, h), (i), (j, k), (l, m), (n), (o), (p), (q), (r), (s), (t) and (u) as described above or the steps (a), (b, c, d), (e), (f), (g, h), (i), (j, k), (l, m), (n), (o), (p), (q), (r), (s), (t) and (u) as described above or the steps (a), (b, c, d), (e), (f), (g, h), (i), (j, k), (l, m), (n), (o), (p), (q), (r), (s), (t), (u), (α), (β), (γ), and (δ), optionally (δ1) and (δ2) or (δ1) and (δ3), as described above.

Furthermore, the present invention concerns the process of preparation of Ecteinascidin-743 which comprises the steps (f), (g, h), (i), (j, k), (l, m), (n), (o), (p), (q), (r), (s), (t), (u) and (v) as described above or the steps (a), (b, c, d), (e), (f), (g, h), (i), (j, k), (l, m), (n), (o), (p), (q), (r), (s), (t), (u) and (v) as described above or the steps (a), (b, c, d), (e), (f), (g, h), (i), (j, k), (l, m), (n), (o), (p), (q), (r), (s), (t), (u), (v), (α), (β), (γ), and (δ), optionally (δ1) and (δ2) or (δ1) and (δ3), as described above.

In a particular process according to the present invention, the compound of formula II bis according to the present invention in which $R_8$ represent a O protecting group, in particular a Troc group, is obtained by step (8) of Swern oxidation of the compound of the following formula III bis

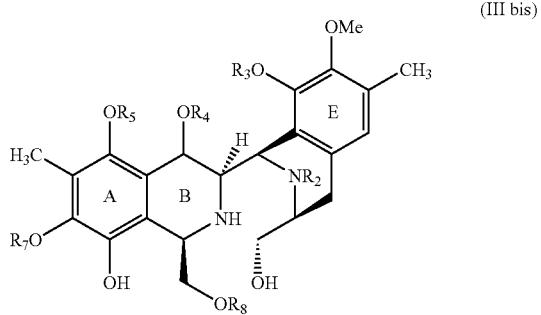

(III bis)

in which $R_2$, $R_3$, $R_4$, $R_5$ and $R_7$ have the same meaning as in formula II bis and $R_8$ represent a O protecting group, in particular a Troc group, followed by a zinc chloride-catalyzed intramolecular Strecker reaction.

Advantageously, the conditions of the Swern oxidation are as follow:

Oxalyl chloride, DMSO, $CH_2Cl_2$ at −60° C.

Advantageously, the conditions of the Strecker reaction are as follow: TMSCN in $CH_2Cl_2$ at room temperature.

In particular, the compound of formula III bis according to the present invention is obtained by a prior step (7) of Pictet-Spengler reaction of the compound of the following formula IV bis

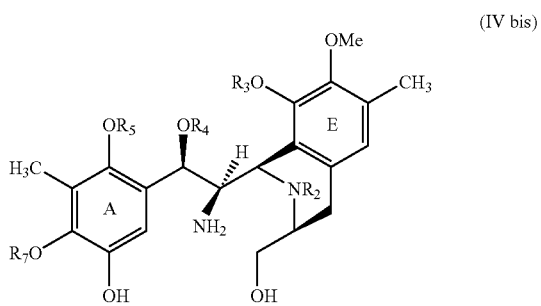

(IV bis)

in which $R_2$, $R_3$, $R_4$, $R_5$ and $R_7$ have the same meaning as in formula III bis with the compound 2-O—$R_8$-acetaldehyde in which $R_8$ has the same meaning as in formula III bis, advantageously in the presence of acetic acid and molecular sieves. Advantageously, the Pictet-Spengler reaction is realized in dichloromethane in the presence of a 3 Å molecular sieves.

Advantageously $R_8$ represent a Troc group and 2-O-Troc-acetaldehyde is prepared in two steps from ethylene glycol.

Particularly, the compound of formula IV bis according to the present invention is obtained by prior steps (4, 5, 6) as follow:

(4)—protection of the two hydroxyl groups by two O-protecting group $R_4$ and $R_5$ of the compound of the following formula V bis

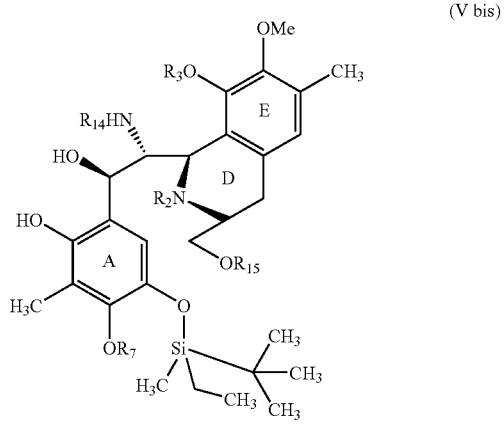

(V bis)

in which $R_2$, $R_3$ and $R_7$ have the same meaning as in formula IV bis, $R_{14}$ is different from $R_2$ and represent a N-protecting group, advantageously a Boc group, and $R_{15}$ is different from $R_3$, $R_4$, $R_5$ and $R_7$ and represent a O-protecting group, advantageously an acetyl group;

Advantageously the two O-protecting groups $R_4$ and $R_5$ are identical. More advantageously they represent a MOM group. In this case the conditions are as follow:

MOMCl, DIPEA (N,N-diisopropylethylamine), $CHCl_3$ at a temperature of 0° C. to reflux;

(5)—simultaneous removal of the O-silyl protective group and of the N-protecting group $R_{14}$ by a Ohfune's procedure; in the case where $R_{14}$ represents a Boc group the conditions are as follow: tert-butyldimethylsilyl-OTf, 2,6-lutidine in $CH_2Cl_2$ at −78° C. and then KF in MeOH at room temperature.

(6)—removal of the O-protecting group $R_{15}$. In case where $R_{15}$ represents an acetyl group, the conditions are as follow: $K_2CO_3$ in MeOH at room temperature;

Advantageously the compound of formula V bis according to the present invention is obtained by a prior steps (3) of stereoselective phenolic aldol condensation of the compound of the following formula VI bis

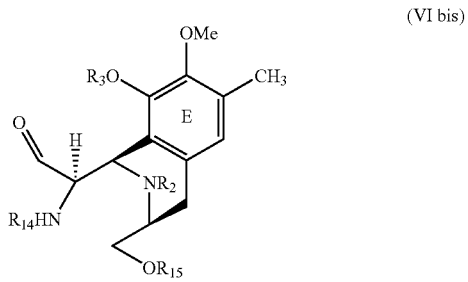

(VI bis)

in which $R_2$, $R_3$, $R_{14}$ and $R_{15}$ have the same meaning as in formula V bis, with magnesium phenolate of the compound of the following formula VII bis

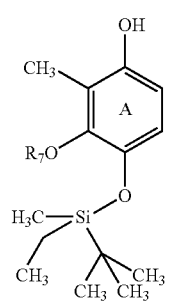

(VII bis)

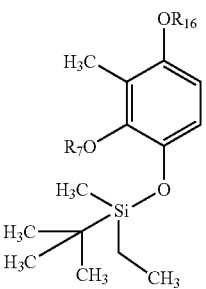

(XIII bis)

in which $R_7$ has the same meaning as in formula V bis.

Advantageously the conditions of the reaction are as follow:

MeMgCl in THF at room temperature.

In a particular process according to the present invention, the compound of formula VII bis according to the present invention is obtained by a prior steps (2) of Swern oxidation of the primary alcohol of the compound of the following formula VIII bis

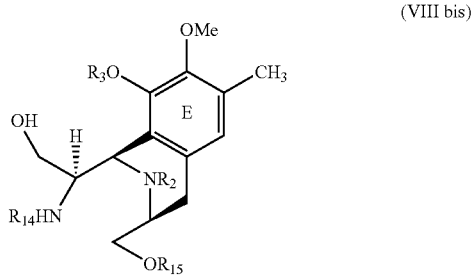

(VIII bis)

in which $R_2$, $R_3$, $R_{14}$ and $R_{15}$ have the same meaning as in formula VI bis.

Advantageously the conditions of the reaction are as follow:

Oxalyl chloride, DMSO and $CH_2Cl_2$ at –60° C., then $Et_3N$.

Particularly, the compound of formula VIII bis according to the present invention is obtained by a prior step (1) of selective hydrolysis of the oxazolidine of the compound of the following formula IX bis

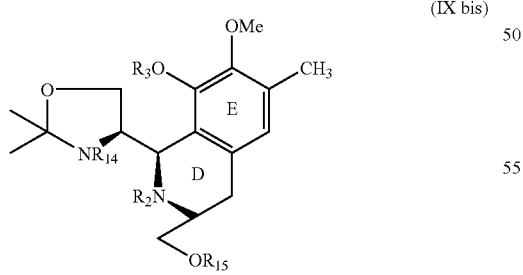

(IX bis)

in which $R_2$, $R_3$, $R_{14}$ and $R_{15}$ have the same meaning as in formula VIII bis, advantageously using $CeCl_3$ and oxalic acid in acetonitrile, more advantageously at room temperature.

In an advantageous process, the compound of formula VII bis according to the present invention is obtained by removal of the $R_{16}$ O-protecting group of the compound of the following formula XIII bis in which $R_7$ has the same meaning as in formula VII bis.

Advantageously $R_{16}$ represent a MOM group and the conditions are as follow:

TMSBr in $CH_2Cl_2$ at a temperature of –20° C. to 0° C.

Advantageously, in the process according to present invention $R_1$ represents a Troc group, $R_2$ represents an Alloc group, $R_3$ represents an allyl group, $R_8$ represents an acetyl group, $R_4$, $R_5$ and $R_9$ represent a MOM group, $R_{10}$ represents a TBS group and $R_{12}$ represents an acetyl group.

Advantageously, the present invention concerns the process of preparation of a compound of formula I which comprises the steps (1), (2), (3), (4, 5, 6), (7), (8), (o) and (p) as described above.

The present invention concerns also the use of the intermediate of formula I according to the present invention for the preparation of the Ecteinascidin-597 of the following formula 1g

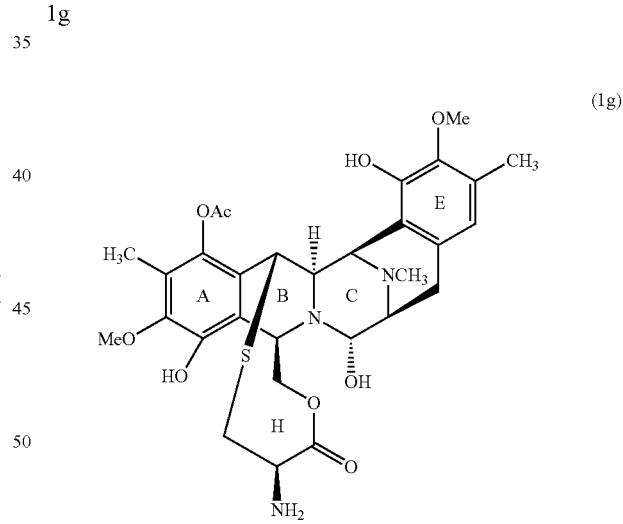

(1g)

or of the Ecteinascidin-583 of the following formula 1h

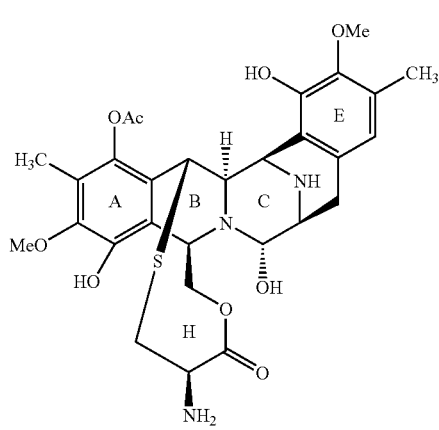

(1h)

In particular the present invention concerns the process of preparation of the Ecteinascidin-597 of formula 1g and/or of the Ecteinascidin-583 of formula 1h which comprises the following steps:

9) dissolution of the compound of formula I according to the present invention in which $R_7$ represent a methyl group in $CH_2Cl_2$ containing TFA in the presence of $Et_3SiH$ in order to obtain the compound of formula X bis

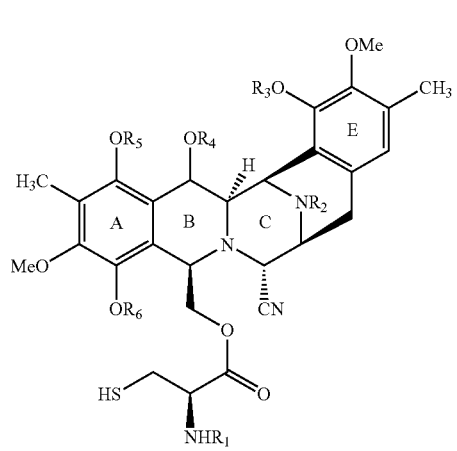

(X bis)

in which $R_1$, $R_2$, $R_3$, $R_4$, $R_5$ and $R_6$ have the same meaning as above;

10) treatment of the compound of formula X bis with TMSBr and simultaneous removal of the O-protecting groups $R_4$ and $R_5$ followed by the acetylation of the hydroxyl group in order to obtain the compound of the following formula XI bis

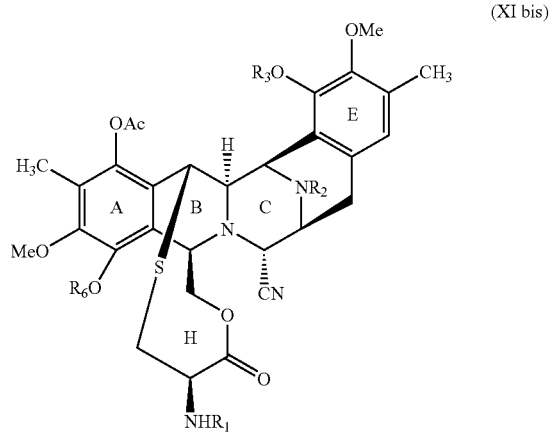

(XI bis)

in which $R_1$, $R_2$, $R_3$ and $R_6$ have the same meaning as in the above formula X bis;

11) removal of the O-protecting groups $R_3$ and $R_6$ and of the group $R_2$ in order to obtain the compound of the following formula XII bis

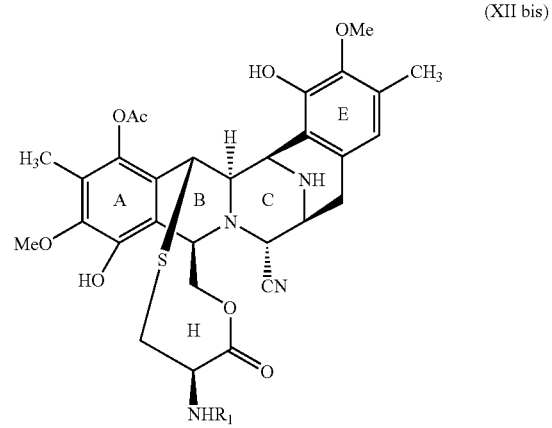

(XII bis)

in which $R_1$ has the same meaning as in the above formula XI bis;

12) reductive N-methylation, removal of the group $R_1$ and conversion of aminonitrile to aminal, advantageously using $AgNO_3$ in a mixture of acetonitrile and water, in order to obtain the compound of formula 1g

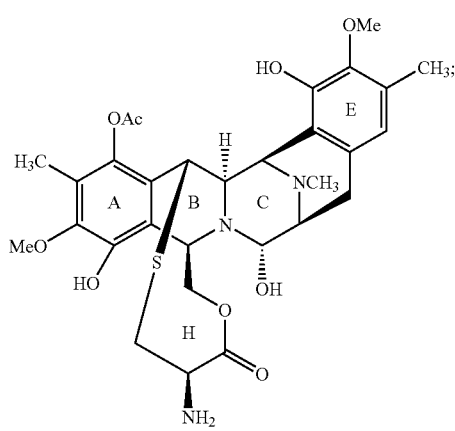

(1g)

13) or removal of the group $R_1$ and conversion of aminonitrile to aminal, advantageously using $AgNO_3$ in a mixture of acetonitrile and water, in order to obtain the compound of formula 1h

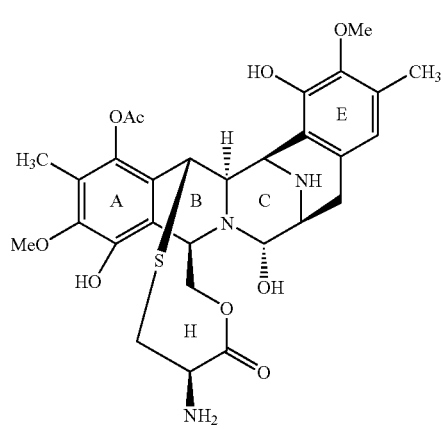

(1h)

Advantageously, the present invention concerns the process of preparation of Ecteinascidin-597 which comprises the steps (9), (10), (11) and (12) as described above or the steps (1), (2), (3), (4, 5, 6), (7), (8), (o), (p), (9), (10), (11) and (12) as described above.

Furthermore, the present invention concerns the process of preparation of Ecteinascidin-583 which comprises the steps (9), (10), (11) and (13) as described above or the steps (1), (2), (3), (4, 5, 6), (7), (8), (o), (p), (9), (10), (11) and (13) as described above.

Having generally described this invention, a further understanding of characteristics and advantages of the invention can be obtained by reference to certain specific examples and figures which are provided herein for purposes of illustration only and are not intended to be limiting unless otherwise specified.

EXPERIMENTAL SECTION

Preparation of Et 743

The retro synthetic scheme of Et 743 is depicted in the Scheme 1. It was anticipated that cyclization of suitably protected carbinolamine 8, that embodies all the requisite functionalities of Et 637 would afford the desired hexacyclic compound 6 whose conversion to natural products are known. The C-4 hydroxy group was strategically positioned in compound 8 to facilitate the formation of the 10-membered lactone via an intramolecular carbon-sulphur bond forming process. Compound 8 in turn could be prepared by assemblage of fully functionalized tetrahydroisoquinoline 9 and suitably protected cysteine 10. Intermolecular N-alkylation of 12 by benzyl bromide 11 followed by intramolecular Strecker reaction was projected for the preparation of 9. The Pictet-Spengler reaction (Cox, E. D. et al. *Chem. Rev.* 1995, 95, 1797-1842) between Garner's aldehyde 13 and amino alcohol 14 was in turn expected to provide the tetrahydroisoquinoline 12. Overall, Et 743 was expected to be synthesized from five readily accessible building blocks; 7, 10, 11, 13, and 14 in a highly convergent manner.

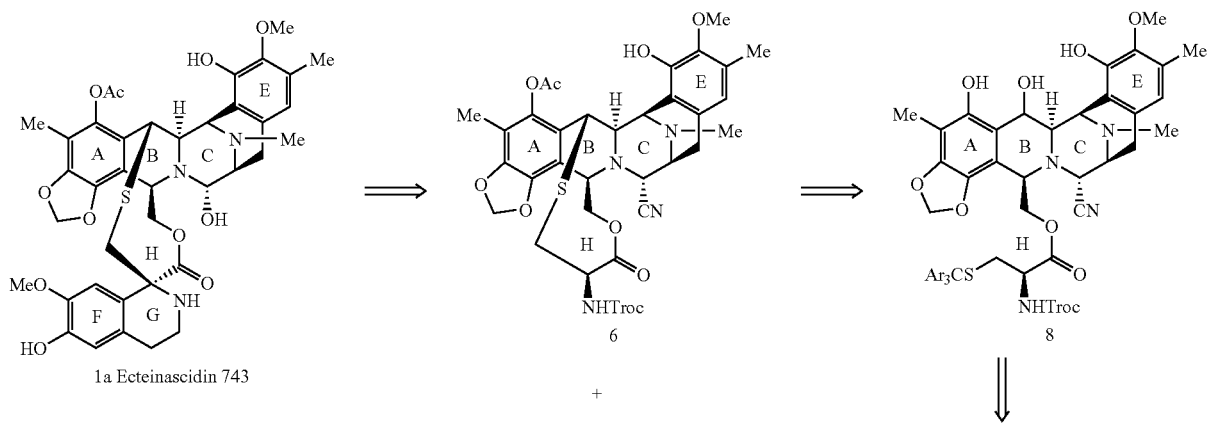

Scheme 1

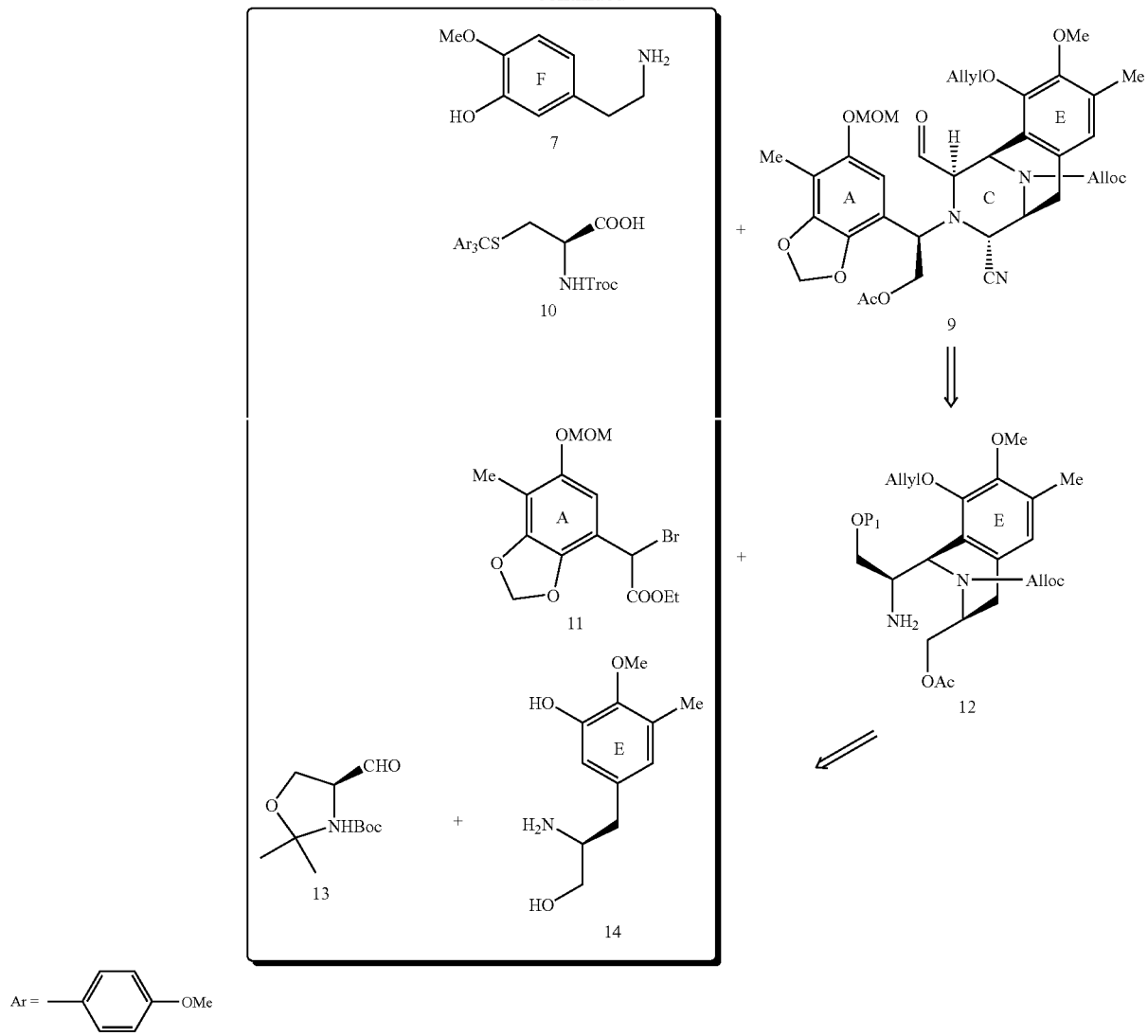

Synthesis of Benzyl Bromide 11.

Compound 11 was synthesized as shown in the Scheme 2. Masking the hydroxyl group of sesamol (15) by MOMCl followed by a sequence of regioselective lithiation/boration/oxidation afforded phenol 16. Hydroxyalkylation of 16 with ethyl glyoxalate under the newly developed conditions (LiCl, 1,1,1,3,3,3-hexafluoroisopropanol/toluene=¼, room temperature) furnished α-hydroxy ester in excellent yield. Selective triflation of 17 using 4-nitrophenyltriflate (18) as sulfonylation agent developed by Zhu and co workers (*J. Org. Chem.* 1999, 64, 7638-7642) provided 19. Suzuki-Miyaura cross-coupling (*Chem. Rev.* 1995, 95, 2457-2483) between 19 and trimethyl boroxine afforded 20 which is converted to bromide 11 in excellent yield.

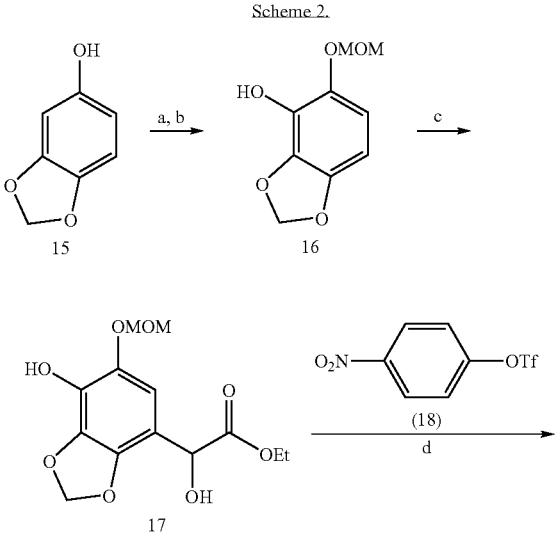

Scheme 2.

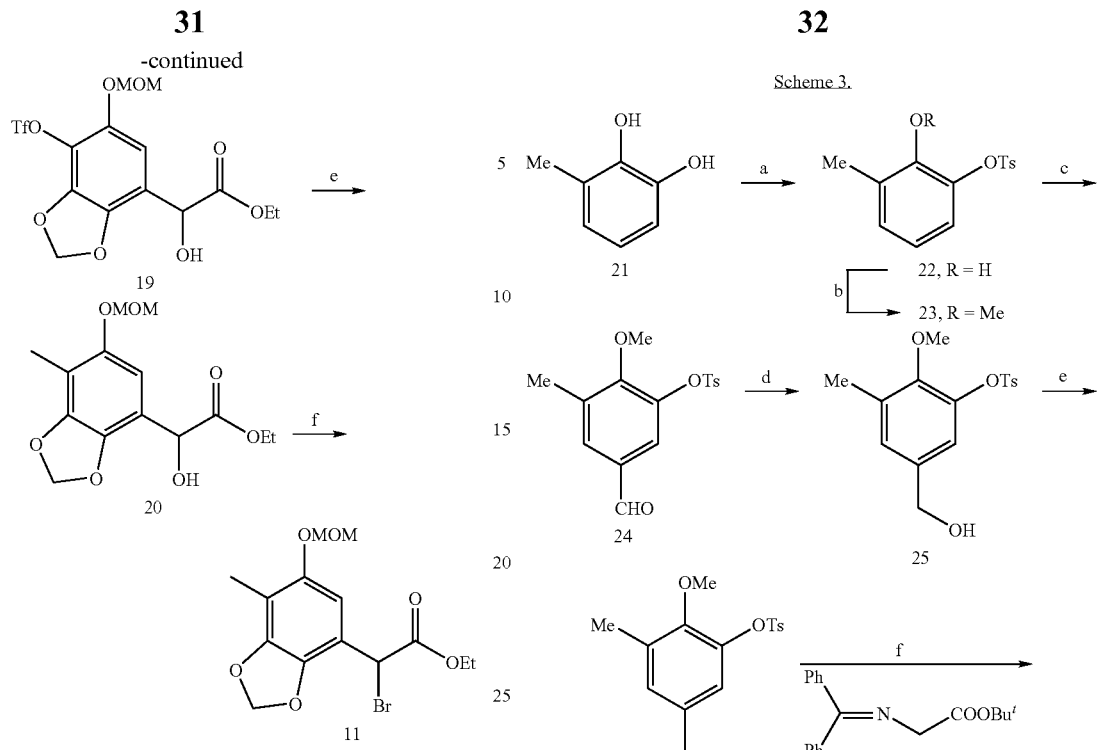

Reagents and condition:
a) MOMCl, NaH, Et$_2$O/DMF, 96%;
b) n-BuLi, B(OMe)$_3$, THF then AcOH, H$_2$O$_2$, 95%;
c) LiCl, 3Å, HFIP/toluene, ethyl glyoxalate, rt, 97%;
d) K$_2$CO$_3$, DMF, rt, 94%;
e) TMB, K$_3$PO$_4$, Pd[P(Ph)$_3$)$_4$], dioxane, refluxing, 93%;
f) SOBr$_2$, benzyltriazole, CH$_2$Cl$_2$, 91%

Synthesis of Amino Alcohol 14.

The protected L-3-hydroxy-4-methoxy-5-methyl phenylalanyl (14) was prepared featuring a key enantioselective alkylation step (Scheme 7). Regioselective mono-protection of 3-methyl catechol (21) with tosyl chloride followed by methylation provided compound 23. The tosylation was conducted at lower temperature with a slight default in tosyl chloride to avoid bis-tosylation. Formylation of 23 with α,α-dichloromethyl methyl ether in the presence of titanium chloride (1M in dichloromethane) provided 24 in 85% yield as the only isolable regioisomer. The presence of a tosyloxy function at C-3 might account for the observed high regioselectivity. Reduction of aldehyde 24 to alcohol 25 (NaBH$_4$, MeOH-THF—H$_2$O) followed by bromination (PBr$_3$, toluene-CH$_2$Cl$_2$=4/1) furnished 26 in 96% overall yield. Following Corey's procedure (J. Am. Chem. Soc. 1997, 119, 12414-12415), alkylation of N-(diphenylmethylene)glycine tert-butyl ester 27 by 3-tosyloxy-4-methoxy-5-methyl benzyl bromide 26 in the presence of a catalytic amount of O-(9)-allyl-N-(9'-anthracenylmethyl)cinchonidium bromide 28 (0.1 equiv) afforded, after chemoselective hydrolysis of the imine function (THF—H$_2$O-ACOH), the amino ester 29 in 85% overall yield. Reduction of ester to alcohol followed by de-tosylation under basic conditions gave the amino alcohol 14.

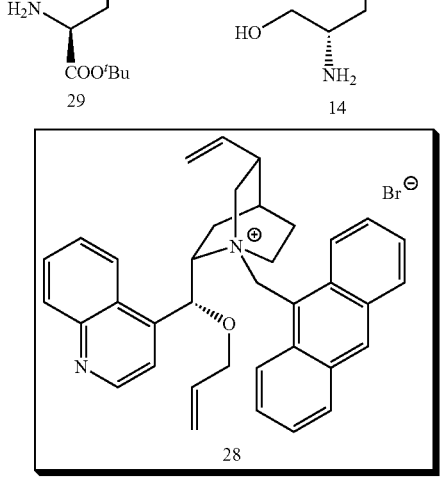

Reagents and conditions:
a) TsCl, Et$_3$N, CH$_2$Cl$_2$, -70° C.;
b) MeI, K$_2$CO$_3$, acetone, 55° C., 84% for two steps;
c) TiCl$_4$ in CH$_2$Cl$_2$, Cl$_2$CHOCH$_3$, 0° C. → r.t., 85%;
d) NaBH$_4$, MeOH: THF: H$_2$O (1:1:0.1), 0° C., quantitative;
e) PBr$_3$, toluene/CH$_2$Cl$_2$, (4:1), 0° C. → r.t., 96%;
f) 27, 28 (10%), CsOH•H$_2$O, CH$_2$Cl$_2$, -78° C. then after work up THF: H$_2$O: AcOH, (1:1:1), 85%;
g) LiBH$_4$, MeOH, Et$_2$O, r.t.;
h) NaOH 2N aq., EtOH, reflux, 80%.

The (S) configuration of amino ester 14 was assigned, taking for granted the Corey's empirical model. To confirm this assignment, both (S)— and (R)—O-methyl mandelic amides 30 and 31 were synthesized (Assignment of absolute configuration of amino alcohol 14, provided below.). The calculated chemical shift differences (ΔδArCH$_2$(30-31)=−0.08 ppm; ΔδTBDMSOCH$_2$ (30-31)=0.09 ppm) are in accord with the S configuration of the amino alcohol, hence that of the amino ester 14 (Trost, B. M. et al. *J. Org. Chem.* 1994, 59, 4202-4205; Helmchen, G. et al. *Tetrahedron Lett.* 1972, 3873-3878). In addition, analysis of $^1$H NMR spectra of compounds 30 and 31 indicated that the de of 30 and 31, hence the ee of their precursor 14, is higher than 90%.

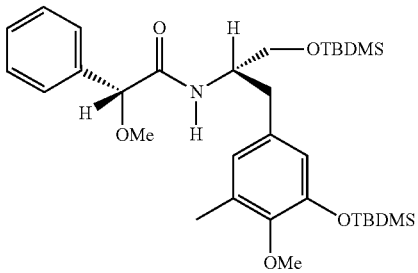

31

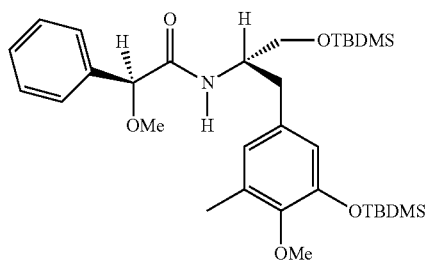

30

Assemblage of Fragments 13 and 14 to 12.

Condensation of Garner's aldehyde 13 (*J. Org. Chem.* 1987, 52, 2361-2364; *J. Org. Chem.* 1988, 53, 2979-2984. *J. Org. Chem.* 1988, 53, 4395-4398); and amino alcohol 14 in the presence of molecular sieve under acidic conditions provided tetrahydroisoquinoline 32 in excellent yield and diastereoselectivity. The configuration of newly created chiral center was deduced from detailed NMR studies and was late confirmed by X-ray analysis of its derivative (cf infra). Protecting group manipulation of 32 provided compound 33 which upon chemoselective hydrolysis of the oxazolidine (CeCl$_3$.7H$_2$O, MeCN, oxalic acid, room temperature (rt), 3 h) and removal of the N-Boc function (TFA/anisol, CH$_2$Cl$_2$, rt, 10 h) provided amino alcohol 12 in excellent yield. Alternatively, treatment of 33 with TFA provided one-step synthesis of 12 in 72% yield.

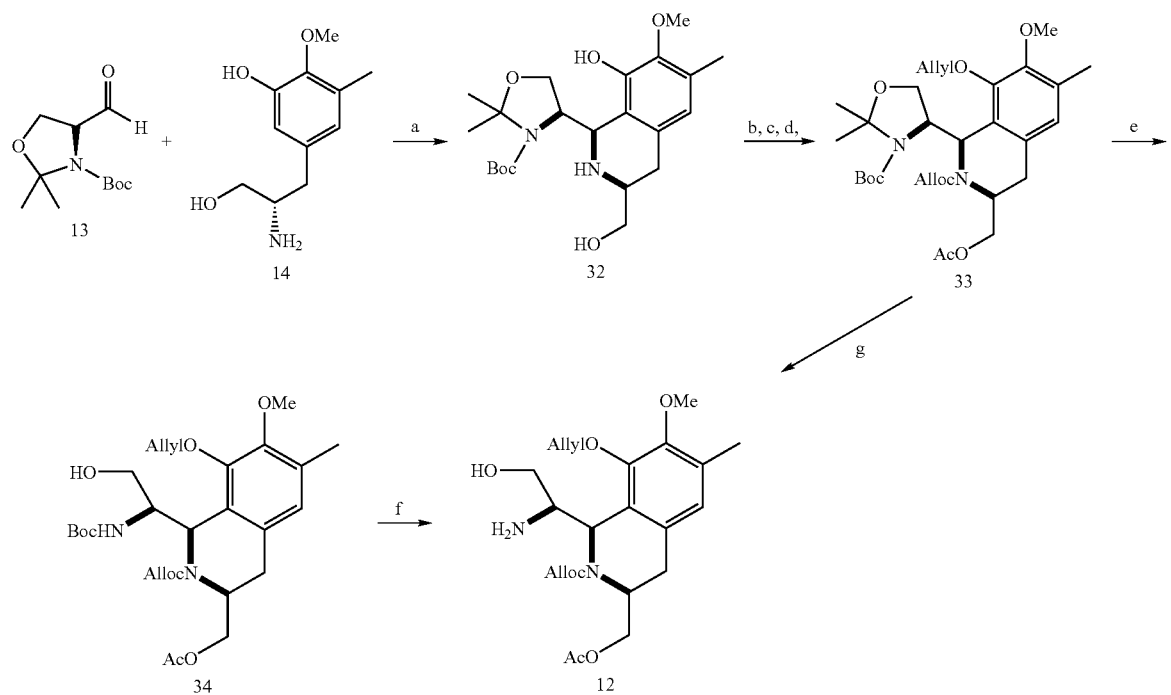

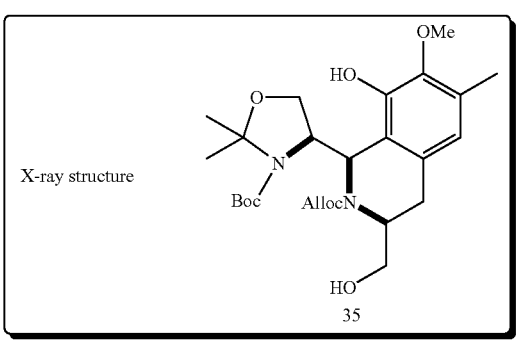

Reagents and conditions:
a) AcOH/CH$_2$Cl$_2$, 3Å, rt, 20 h, 84%;
b) AllocCl, NaHCO$_3$/CH$_2$Cl$_2$, rt, 2 h, 88%;
c) AllylBr, CsCO$_3$, DMF, rt, 3 h, 86%;
d) Ac$_2$O/Py, CH$_2$Cl$_2$, DMAP, rt, 1 h, 92%;
e) CeCl$_3$•7H$_2$O, MeCN, oxalic acid, rt, 3 h, 91%
f) TFA/anisole, CH$_2$Cl$_2$, rt, 10 h, 85%;
g) TFA in CH$_2$Cl$_2$, rt, 72%.

Synthesis of Compound 6.

One of the key step in the present synthesis is the diastereoselective N-alkylation of chiral amino alcohol by a racemic benzyl bromide. Under optimized conditions, coupling of 12 and 11 took place smoothly (triethylamine in acetonitrile) to provide two separable diastereomers 36 and 37 in 91% yield in a ratio of 1/3. The observed stereoselectivity could be explained by a S$_N$1 mechanism via an ortho methide intermediate (Van DeWater, R. W. *Tetrahedron* 2002, 58, 5367-5405). The desired diastereomer 37 (cf infra for determination of stereochemistry) was isolated in 68% yield. Masking of the primary hydroxyl group as TBS ether and hydrolysis of acetate under mild basic conditions afforded compound 38. Oxidation of hydroxyl group using Dess-Martin reagent followed by Zinc chloride-catalyzed Strecker reaction provided amino nitrile 39. Reduction of ester to alcohol followed by acetylation afforded compound 40 which upon desilylation and oxidation was converted to 9. The Pomerantz-Fritsch type cyclization (Bobbit, J. M. et al. *J. Org. Chem.* 1965, 30, 2247-2250) of 9 took place smoothly under acidic conditions (TFA in dichloromethane) to afford hexacyclic compound 41 with concomitant removal of the phenolic MOM protecting group. Saponification of 41 followed by coupling of the resulting alcohol 42 with (R)—N-Troc-(S-4,4',4"-trimethoxyltrityl) Cys (10) (Synthesized from commercial available (R)—S-trityl Cys in three-steps in 76% overall yield: a) TrocCl, NaHCO$_3$, H$_2$O/1,4-dioxane, 45° C.; b) Et$_3$SiH, TFA, CH$_2$Cl$_2$; c) (p-4-MeOPh)$_3$CCl, CH$_2$Cl$_2$) under standard conditions afforded the compound 8 in 94% yield. Gratifyingly, by simply dissolving 8 in TFE containing 1% of TFA, the bridged macrocycle 43 was produced in 77% isolated yield as the corresponding acetate. In this operationally simple experiment, a complex reaction sequence involving S-trityl deprotection, 1,4-β elimination leading to ortho quino methide and macrocyclization via an intramolecular Michael addition occurred in a highly ordered manner, to accomplish the key C—S bond forming process. Simultaneous removal of N-Alloc and O-allyl functions under Guibé's conditions (*Tetrahedron* 1998, 54, 2967-3042) followed by reductive N-methylation provided the key intermediate 6 in excellent overall yield.

Scheme 5.

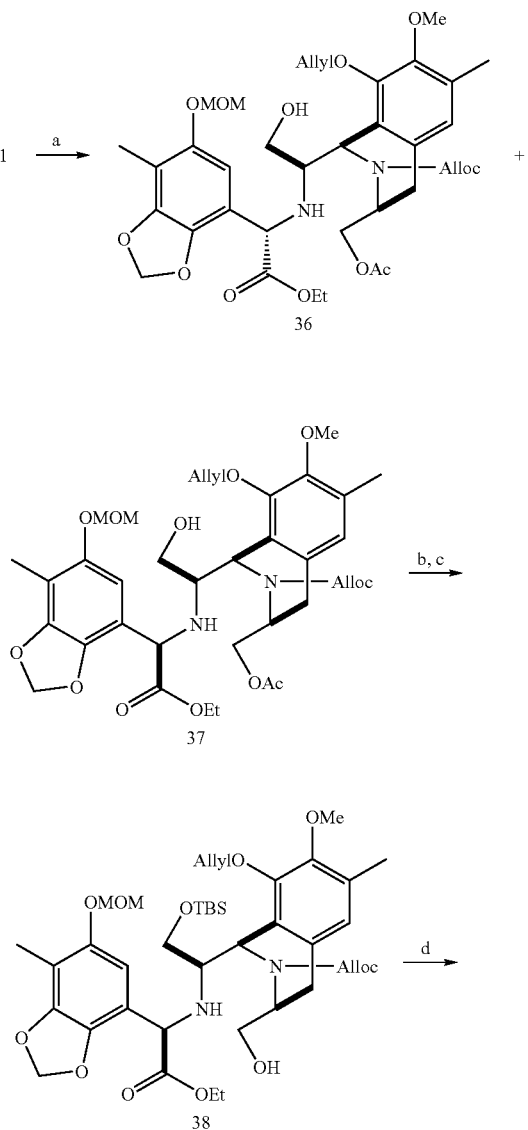

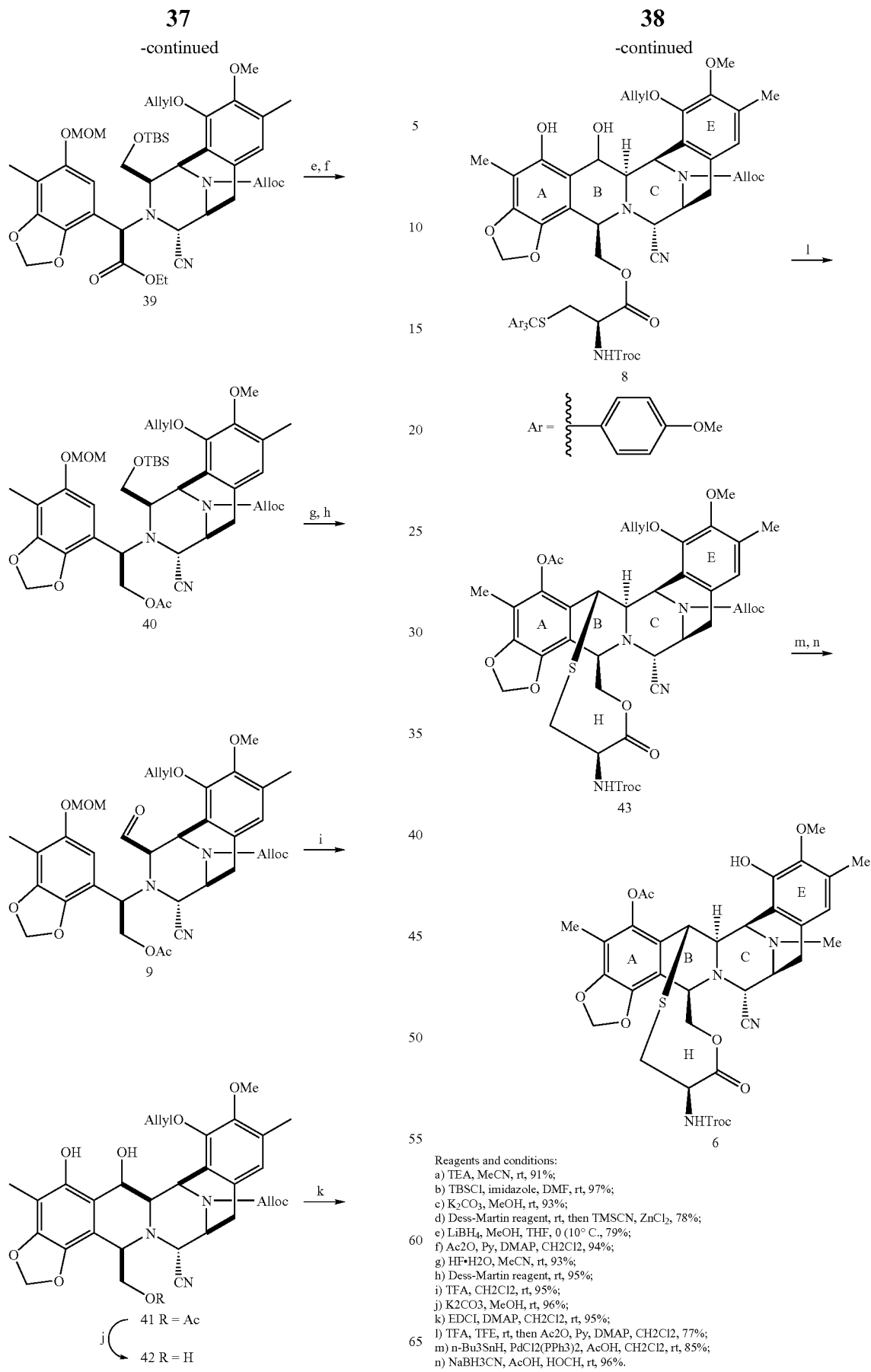

The stereochemistry of compounds 36 and 37 was determined by their transformation into the corresponding lactones 45 and 48 (scheme 6). Detailed spectroscopic studies including nOe allowed the determination of the relative stereochemistry of both compounds 45 and 48, hence that of 36 and 37.

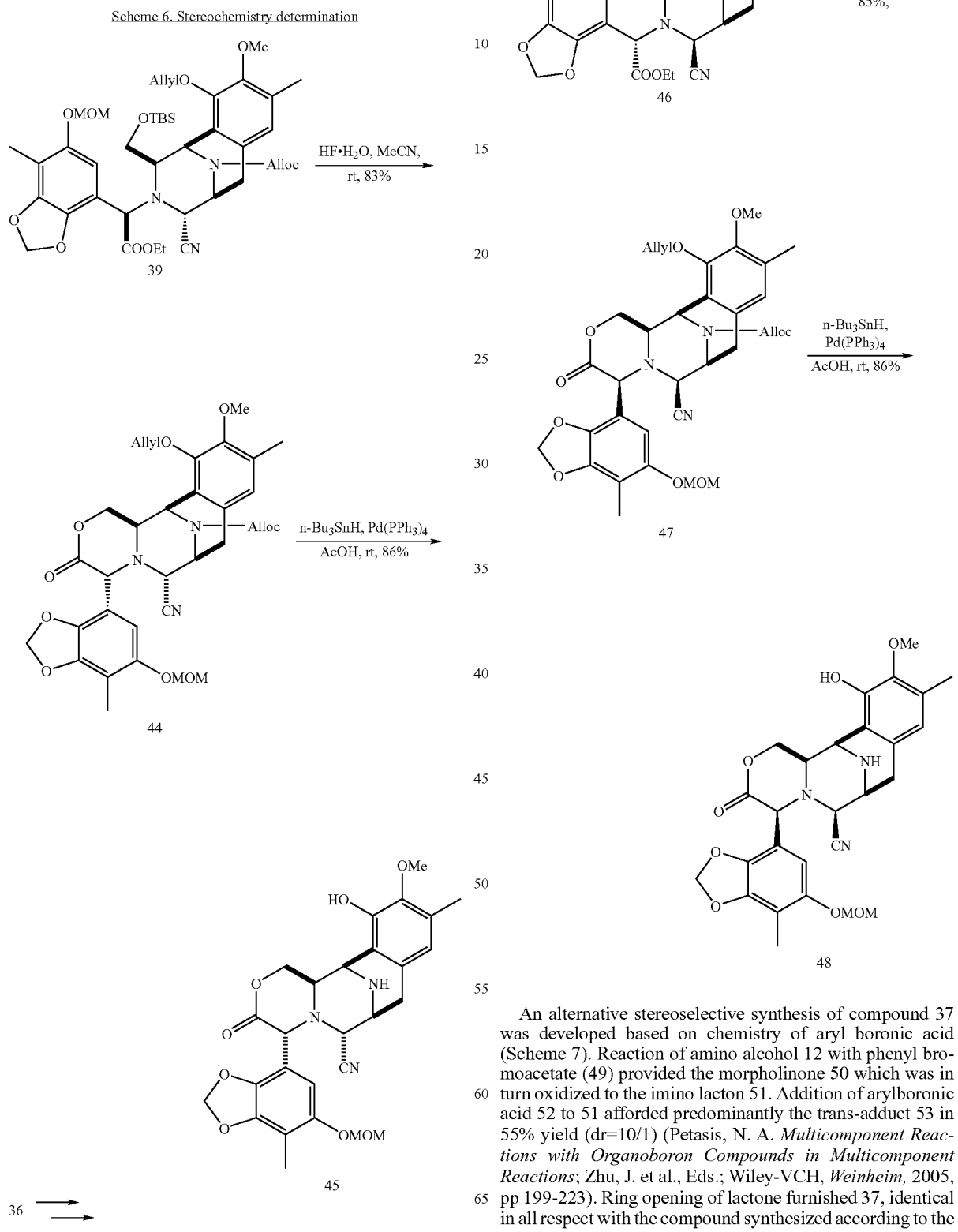

An alternative stereoselective synthesis of compound 37 was developed based on chemistry of aryl boronic acid (Scheme 7). Reaction of amino alcohol 12 with phenyl bromoacetate (49) provided the morpholinone 50 which was in turn oxidized to the imino lacton 51. Addition of arylboronic acid 52 to 51 afforded predominantly the trans-adduct 53 in 55% yield (dr=10/1) (Petasis, N. A. *Multicomponent Reactions with Organoboron Compounds in Multicomponent Reactions*; Zhu, J. et al., Eds.; Wiley-VCH, *Weinheim*, 2005, pp 199-223). Ring opening of lactone furnished 37, identical in all respect with the compound synthesized according to the scheme 5.

Scheme 7.

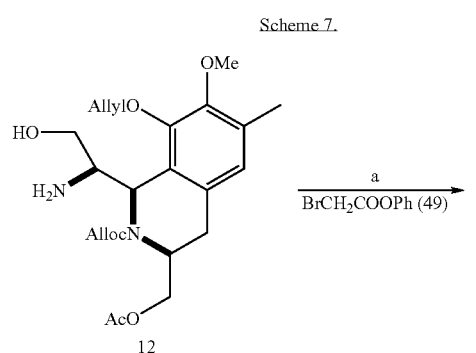

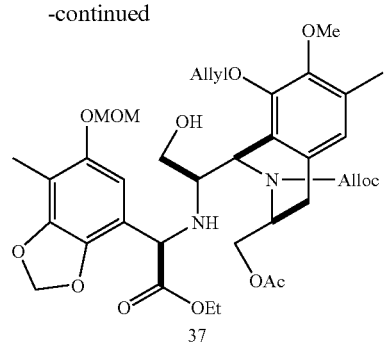

Reagents and Conditions:
a) BrCH₂COOPh (49), Diisopropyl ethylamine, MeCN, 10° C., 90%;
b) Pb(OAc)₄, MeCN, rt, 82%;
c) TFA, CH₂Cl₂, rt, 55%; d)K₂CO₃, EtOH, -20° C., 94%.

Total Synthesis of Et 743.

Conversion of 6 to Et-743 was realized according to the procedures developed by Corey and co-workers. Removal of N-Troc under reductive conditions followed by oxidation of the resulting primary amine 54 afforded keto ester 55. Pictet-Spengler reaction of 55 with 3-hydroxy-4-methoxyphenethyl amine (56) provided 57 (Et 770) (Suwanborirux, K. et al. *J. Nat. Prod.* 2002, 65, 935-937) which was converted in Et-743 by treatment with silver nitrate in 93% yield.

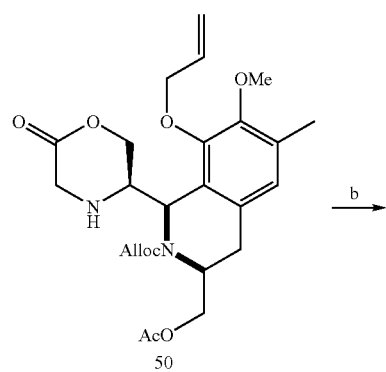

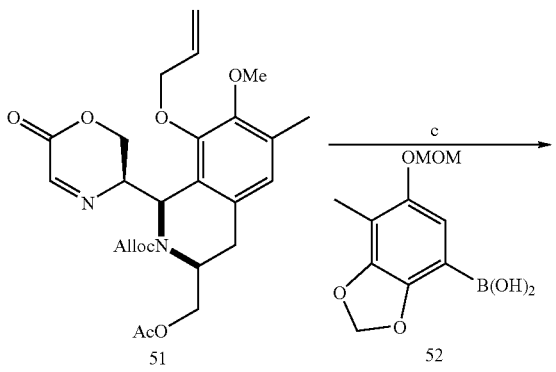

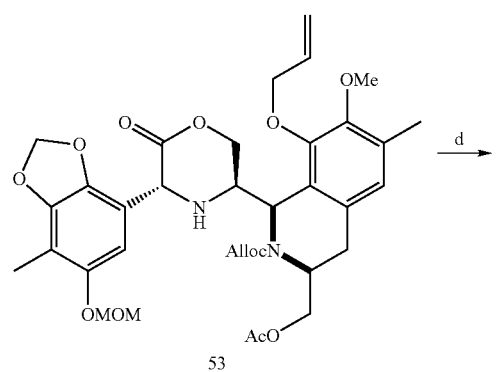

Scheme 8.

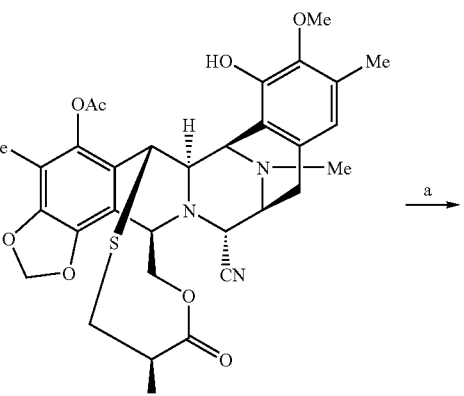

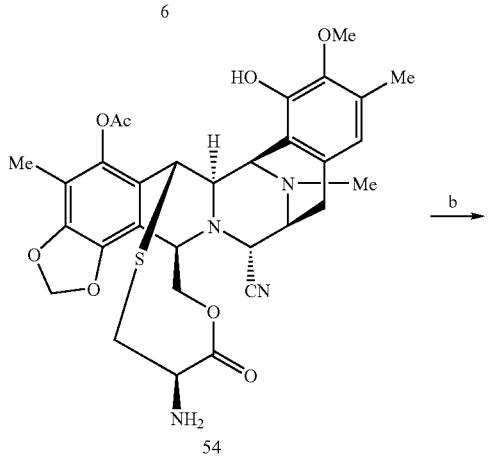

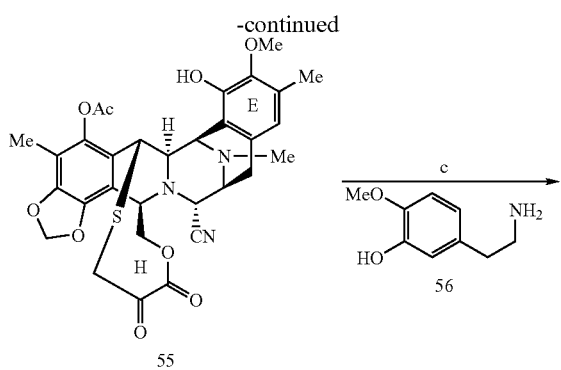

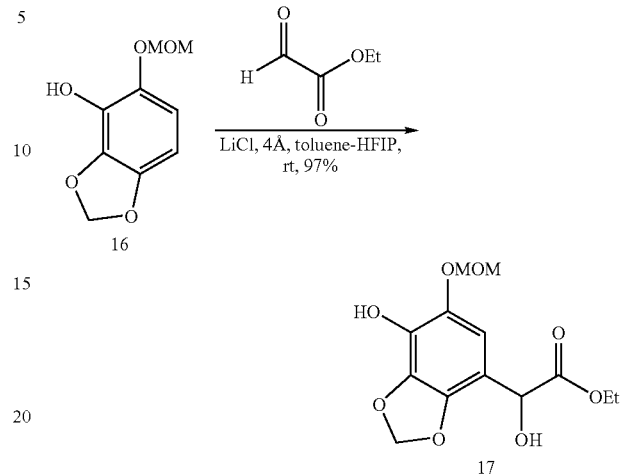

Compound 17

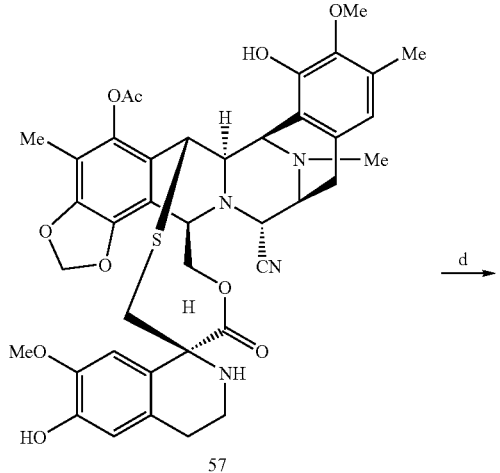

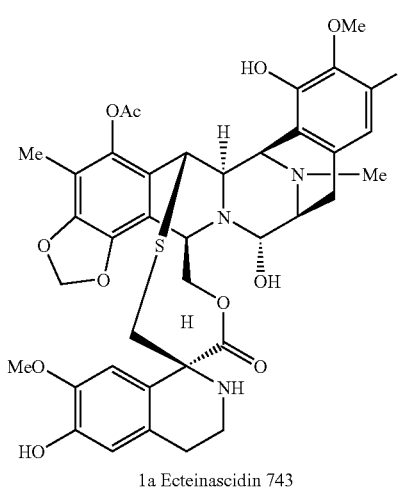

1a Ecteinascidin 743

Reagents and conditions:
a) AcOH, Zn, rt, 92%;
b) 4-formyl-1-methylpyridinium benzenesulfonate, DBU, sat. oxalic acid, DMF-CH₂Cl₂, rt, 53%;
c) NaOAc, EtOH, rt, 95%;
d) AgNO₃ MeCN-H₂O, rt, 91%

A solution of 2-hydroxylsesamol 16 (0.99 g, 5 mmol), ethyl glyoxylate (612 mg, 6 mmol), lithium chloride (424 mg, 10 mmol) and the 4 Å molecular sieves (0.5 g) in toluene and 1,1,1,3,3,3-hexfluoroisopropanol (4:1, v/v, 20 ml) at room temperature was stirred at room temperature for 24 hours. The solution was diluted with dichloromethane (100 ml) and filtered. The filtrate was concentrated under reduced pressure and the residue was purified by flash column chromatography (33% EtOAc in heptane) to afford phenolic alcohol 17 (1.45 g, 97%) as a colorless oil. IR (neat film) $\nu$3428, 2904, 2358, 1734, 1654, 1499, 1461, 137, 01215, 1046, 994, 931 cm$^{-1}$; $^1$H NMR (300 MHz, CDCl$_3$) δ 6.56 (s, 1H), 6.36 ((s, 1H), 5.99 (d, J=1.3 Hz, 1H), 5.92 (d, J=1.3 Hz, 1H), 5.13 (d, J=5.9 Hz, 1H), 5.08 (d, J=6.6 Hz, 1H), 5.06 (d, J=6.6 Hz, 1H), 4.23 (m, 2H), 3.52 (s, 3H), 3.43 (d, J=5.9 Hz, 1H), 1.23 (t, J=7.1 Hz, 3H); $^{13}$C NMR (75 MHz, CDCl$_3$) δ173.04, 142.27, 141.51, 134.43, 132.31, 110.73, 108.35, 102.13, 97.56, 68.29, 62.21, 56.53, 14.00; HRMS (ESI$^+$) m/z: Calc. for C$_{13}$H$_{16}$O$_8$Na (M+Na)$^+$ 323.0743, found 323.0745.

Triflate 19

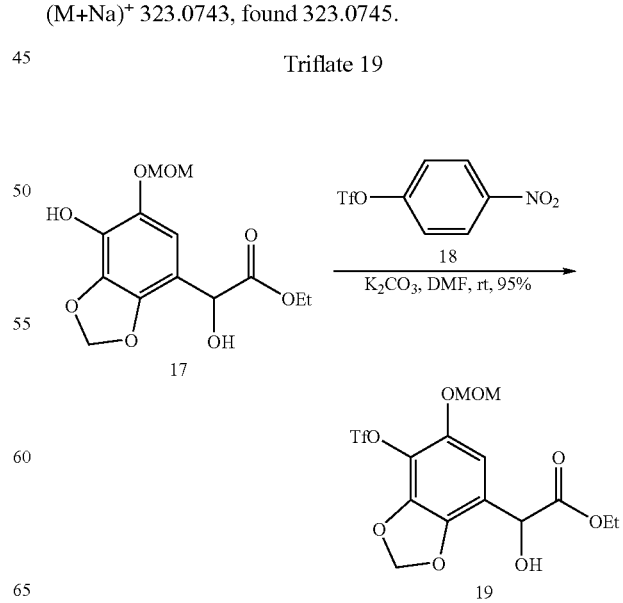

A suspension of alcohol 17 (3 g, 10 mmol), potassium carbonate (2.8 g, 20 mmol), and p-nitrophenol trifluoromethyl sulfonate (3 g, 11.0 mmol) in DMF (40 ml) was stirred at 23° C. for 1 hour. The reaction mixture was diluted with diethyl ether (1000 ml) and filtered. The filtrate was washed with water (4×100 ml), brine, dried over sodium sulfate and evaporated to dryness under reduced pressure. The residue was purified by flash column chromatography (25% EtOAc in heptane) to afford triflate 19 (4.1 g, 95%) as a colorless oil. IR (neat film) ʋ3452, 2910, 2358, 1738, 1643, 1494, 1461, 1425, 1365, 1210, 1136, 1103, 1054, 988, 943, 830 cm$^{-1}$;

$^1$H NMR (300 MHz, CDCl$_3$) δ 6.70 (s, 1H), 6.08 (d, J=1.1 Hz, 1H), 6.04 (d, J=1.1 Hz, 1H), 5.17 (d, J=5.7 Hz, 1H), 5.16 (d, J=6.7 Hz, 1H), 5.13 (d, J=6.7 Hz, 1H), 4.26 (m, 2H), 3.49 (s, 3H), 3.48 (d, J=5.7 Hz, 1H), 1.26 (t, J=7.1 Hz, 3H);

$^{13}$C NMR (75 MHz, CDCl$_3$) δ172.30, 145.25, 141.64, 140.19, 123.35, 120.66, 119.04, 116.41, 106.51, 103.34, 96.12, 68.16, 62.65, 56.48, 13.99; HRMS (ESI$^+$) m/z: Calc. for C$_{14}$H$_{15}$F$_3$O$_{10}$NaS (M+Na)$^+$ 455.0236, found 455.0199.

Compound 20

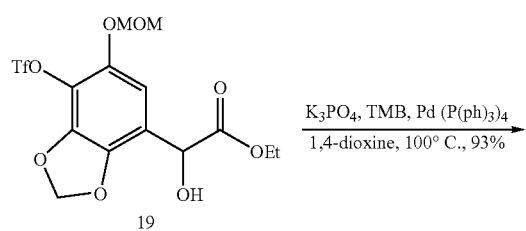

To a solution of triflate 19 (864 mg, 2 mmol), K$_3$PO$_4$ (636 mg, 3 mmol), Pd (Ph$_3$P)$_4$ (70 mg, 0.06 mmol) in 1,4-dioxane (20 ml), trimethylboroxine (300 mg, 2.4 mmol) was added dropwise under argon. After being stirred at 100° C. for 4 hours, the reaction mixture was cooled to room temperature and diluted with dichloromethane (200 ml) and filtered. The filtrate was concentrated under reduced pressure and the residue was purified by flash column chromatography (25% EtOAc in heptane) to afford compound 20 (554 mg, 93%) as a colorless oil. IR (neat film) ʋ3484, 2904, 1736, 1492, 1432, 1208, 1152, 1110, 1055, 985, 934 cm$^{-1}$; $^1$H NMR (500 MHz, CDCl$_3$) δ 6.49 (s, 1H), 5.95 (s, 1H), 5.90 (s, 1H), 5.15 (d, J=6.2 Hz, 1H), 5.08 (bs, 2H), 4.24 (m, 2H), 3.46 (s, 3H), 3.42 (d, J=6.2 Hz, 1H), 2.10 (s, 1H), 1.23 (t, J=7.1 Hz, 3H); $^{13}$C NMR (75 MHz, CDCl$_3$) δ173.05, 151.17, 146.73, 139.66, 116.38, 110.97, 105.52, 101.34, 95.76, 68.81, 62.24, 56.10, 14.06, 8.98; HRMS (ESI$^+$) m/z: Calc. for C$_{14}$H$_{18}$O$_7$Na (M+Na)$^+$ 321.0950, found 321.0933.

Bromide 11

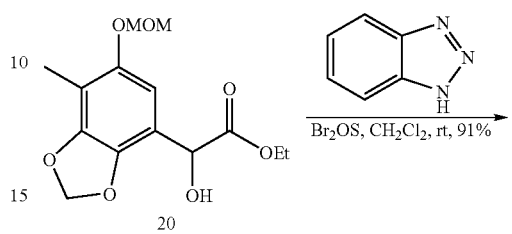

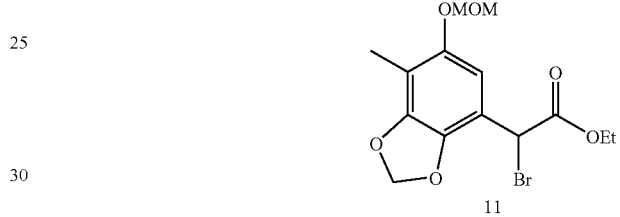

To a solution of alcohol 20 (2.98 g, 10 mmol) in dichloromethane (30 ml), a stock solution of benzotriazole and thionyl bromide in dichloromethane (12 ml, 1.0 N, 1:1, M/M) were added dropwise. After being stirred at room temperature for another 20 min, the reaction mixture was diluted with diethyl ether (500 ml) and filtered through a short ped of celite. The filtrate was washed with water and brine, dried over sodium sulfate, and concentrated under reduced pressure. The residue was purified by flash column chromatography (14% EtOAc in heptane) to afford bromide 11 (3.28 g, 91%) as a pale yellow oil. IR (neat film) ʋ2902, 1745, 1490, 1432, 1366, 1232, 1151, 1111, 1058, 987, 934 cm$^{-1}$; $^1$H NMR (500 MHz, CDCl$_3$) δ 6.76 (s, 1H), 5.96 (s, 2H), 5.49 (s, 1H), 5.13 (d, J=6.4 Hz, 1H), 5.09 (d, J=6.4 Hz, 1H), 4.25 (m, 2H), 3.48 (s, 3H), 2.10 (s, 3H), 1.29 (t, J=9.1 Hz, 3H); $^{13}$C NMR (75 MHz CDCl$_3$, 293 K) δ167.45, 151.25, 146.47, 139.78, 113.68, 111.99, 106.56, 101.53, 95.80, 62.63, 56.22, 40.67, 13.94, 9.09; HRMS (ESI$^+$) m/z: Calc. for C$_{14}$H$_{17}$BrO$_6$Na (M+Na)$^+$ 383.0106, 385.0086, found 383.0073, 385.0094.

Compound 32

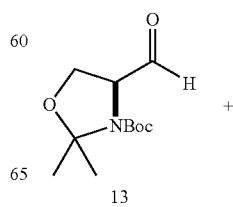

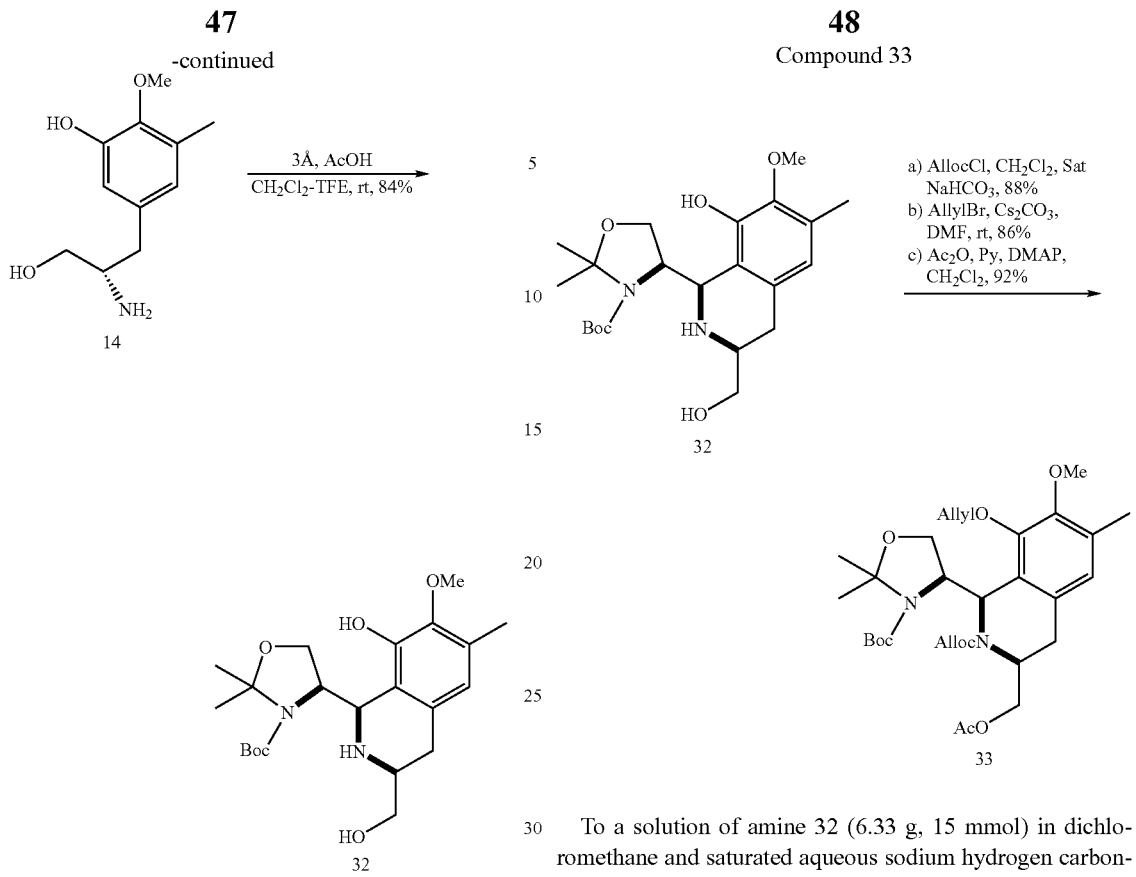

Compound 33

To a solution of amine alcohol 14 (2.11 g, 10 mmol), (S)-Garner's aldehyde 13 (2.77 g, 12 mmol) and the 3 Å molecular sieves (2.0 g) in dichloromethane and 2, 2, 2-trifluoroethanol (7:1, v/v, 40 ml), acetic acid (1.5 g, 1.43 ml, 2.5 mmol) was added dropwise. After being stirred at room temperature for 24 h, the reaction mixture was diluted with dichloromethane and filtered. The filtrate was concentrated under reduced pressure and the residue was purified by flash column chromatography (5% MeOH in dichloromethane) to afford compound 32 (3.54 g, 84%) as a pale yellow oil. $[\alpha]_D^2$ $_{6}$-6.0° (c=1.87, CHCl$_3$). IR (neat film) ν3358, 2977, 2932, 1680, 1454, 1391, 1365, 1236, 1171, 1090, 1061, 1022, 1003, 851 cm$^{-1}$; $^1$H NMR (300 MHz, CDCl$_3$) δ6.45 (s, 1H), 4.91 & 4.83 (bs, 1H), 4.69 & 4.61 (bs, 1H), 3.87 & 3.84 (bs, 1H), 3.75 (s, 3H), 3.69 (dd, J=10.5, 3.0 Hz, 2H), 3.55-3.46 (m, 1H), 2.99 (bs, 1H), 2.70-2.59 (m, 1H), 2.47 (d, J=15.4 Hz, 1H), 2.23 (s, 3H), 1.68 & 1.61 (bs, 3H), 1.50 (bs, 9H), 1.45 (s, 3H); $^{13}$C NMR (125.7 MHz, CD$_3$OD) δ 153.30, 152.69, 152.55, 146.37, 145.70, 144.04, 143.52, 133.10, 132.17, 129.27, 128.55, 122.26, 121.85, 119.93, 119.58, 94.83, 94.03, 80.90, 79.86, 66.01, 64.93, 64.27, 60.76, 60.45, 59.18, 53.15, 52.41, 32.41, 28.50, 26.55, 25.65, 24.27, 23.13, 15.64; HRMS (ESI$^+$) m/z: Calc. for C$_{22}$H$_{35}$N$_2$O$_6$ (M+H)$^+$ 423.2495, found 423.2469. Amine alcohol 14: $^1$H NMR (300 MHz, CD$_3$OD) δ 6.55 (s, 1H), 6.50 (s, 1H), 3.72 (s, 3H), 3.51 (dd, J=10.7, 4.3 Hz, 1H), 3.34 (dd, J=10.3, 6.7 Hz, 1H), 2.61 (dd, J=13.4, 6.3 Hz, 1H), 2.40 (dd, J=13.4, 7.8 Hz, 1H), 2.20 (s, 3H); MS (ESI$^+$) m/z: (M+Na)$^+$ 276.1

To a solution of amine 32 (6.33 g, 15 mmol) in dichloromethane and saturated aqueous sodium hydrogen carbonate (100 ml, 1:1, v/v), allyl chloroformate (2.0 g, 1.1 equiv) was added dropwise. After being stirred at room temperature for 2 hours, the reaction mixture was diluted with dichloromethane (800 ml) and separated. The organic layer was washed with brine, dried with sodium sulfate and evaporated to dryness under reduced pressure. The residue was purified by flash column chromatography (33% EtOAc in heptane) to afford N-Alloc derivative of 32 (6.67 g, 88%) as a white solid. $[\alpha]_D^2$ $^{4.9}$-15.5° (c=0.75, CHCl$_3$). IR (film) ν3414, 2939, 1676, 1459, 1393, 1302, 1239, 1150, 1101, 1065, 1004, 846 cm$^{-1}$; $^1$H NMR (300 MHz, CDCl$_3$) δ 6.52 (s, 1H), 5.8-5.98 (m, 2H), 5.74 (d, J=10.2 Hz, 1H), 5.40 (bd, J=16.0 Hz, 1H), 5.19 (dd, J=10.6, 1.25 Hz, 1H), 4.56-4.73 (m, 2H), 4.25-4.45 (m, 1H), 3.98-4.14 (m, 2H), 3.91 (dd, J=9.1, 5.0 Hz, 2H), 3.72s, 3H), 3.67 (m, 1H), 2.72-3.27 (m, 2H), 2.24 (s, 3H), 1.71 & 1.79 (s, 3H), 1.46 (s, 3H), 1.03 & 1.23 (s, 9H); $^{13}$C NMR (75 MHz, CDCl$_3$) δ 157.49, 152.16, 145.70, 145.33, 143.93, 132.35, 131.83, 129.47, 120.98, 120.69, 117.14, 95.50, 94.77, 79.38, 67.02, 66.44, 65.27, 60.62, 60.39, 58.29, 55.59, 51.80, 30.05, 27.95, 27.57, 26.73, 24.26, 22.98, 22.69, 15.65; HRMS (ESI$^+$) m/z: Calc. for C$_{26}$H$_{35}$N$_2$O$_8$Na (M+Na)$^+$ 529.2526, found 529.2513. A suspension of N-Alloc derivative of 32 (10.1 g, 20 mmol), cesium bicarbonate (13 g, 40 mmol), sodium iodide (300 mg, 0.1 eq) and allyl bromide (7.26 mg, 3 equiv) in DMF (80 ml) was stirred at room temperature for 3 hours. The reaction mixture was diluted with diethyl ether (1500 ml) and washed with water and brine, dried with sodium sulfate and evaporated to dryness under reduced pressure. The residue was purified by flash column chromatography (25% EtOAc in heptane) to afford ether N-Alloc-O-Allyl derivative of 32 (9.4 g, 86%) as colorless oil. $[\alpha]_D^2$ $^{5.2}$-8.2° (c=1.0, CHCl$_3$). IR (neat film)

ν3481, 2933, 1693, 1455, 1389, 1364, 1295, 1253, 1172, 1150, 1067, 993, 927 cm$^{-1}$; $^1$H NMR (300 MHz, CDCl$_3$) δ 6.71 (s, 1H), 6.1-5.84 (m, 2H), 5.67 (d, J=10.5 Hz, 1H), 5.11-5.48 (m, 4H), 4.21-4.73 (m, 5H), 3.97-4.10 (m, 2H), 3.93 (dd, J=9.1, 4.8 Hz, 1H), 3.74 & 3.78 (s, 3H), 3.69 (m, 1H), 2.77 3.57 (m, 3H), 2.19 & 2.23 (s, 3H), 1.71 & 1.78 (s, 3H), 1.42 & 1.45 (s, 3H), 1.02 & 1.20 (s, 9H); $^{13}$C NMR (75 MHz, CDCl$_3$) δ 157.69, 157.40, 152.72, 152.02, 149.72, 149.14, 148.58, 148.15, 134.71, 134.27, 132.18, 131.65, 131.33, 131.13, 130.96, 127.76, 127.38, 124.56, 118.10, 117.92, 117.60, 95.73, 94.89, 79.41, 74.41, 67.16, 66.73, 65.48, 60.15, 57.83, 55.67, 52.97, 52.33, 30.16, 29.70, 28.13, 27.57, 26.96, 26.73, 24.32, 22.86, 15.62; HRMS (ESI$^+$) m/z: Calc. for C$_{29}$H$_{42}$N$_2$O$_8$Na (M+Na)$^+$ 569.2839, found 529.2862. A solution of N-Alloc-O-Allyl derivative of 32 (5.46 g, 10 mmol), acetic anhydride (5 ml), pyridine (10 ml) and DMAP (61 mg, 0.05 equiv) in dichloromethane (50 ml) was stirred at room temperature for 1 hour. After usual work up, the residue was purified by flash column chromatography (16% EtOAc in heptane) to afford compound 33 (5.4 g, 92%) as colorless oil. [α]$_D^{25.5}$-11.9° (c=1.0, CHCl$_3$). IR (neat film) ν2936, 1745, 1692, 1454, 1383, 1364, 1295, 1238, 1172, 1151, 1099, 1067, 993, 931, 847 cm$^{-1}$; $^1$H NMR (300 MHz, CDCl$_3$) δ 6.71 (s, 1H), 6.20-5.83 (m, 2H), 5.66 (bs, 1H), 5.52-5.10 (m, 4H), 4.74-4.23 (m, 7H), 4.16-4.02 (m, 2H), 3.90 (dd, J=8.7, 4.8 Hz, 1H), 3.79 & 3.74 (s, 3H), 3.29 & 2.93 (t, J=13.6 Hz, 1H), 2.87-2.75 (m, 1H), 2.22 & 2.18 (s, 3H), 2.09 (s, 3H), 1.79 & 1.72 (s, 3H), 1.45 & 1.43 (s, 3H), 1.20 & 1.03 (s, 9H); $^{13}$C NMR (75 MHz, CDCl$_3$) δ 170.55, 170.52, 156.67, 155.97, 152.69, 151.99, 149.84, 149.20, 148.61, 148.12, 134.19, 132.32, 131.39, 130.90, 130.61, 127.79, 124.47, 117.84, 95.76, 94.89, 79.35, 74.44, 66.55, 65.85, 65.42, 60.15, 57.94, 52.59, 52.18, 30.19, 28.13, 27.60, 26.96, 26.67, 24.26, 22.77, 20.85, 15.62; HRMS (ESI$^+$) m/z: Calc. for C$_{31}$H$_{44}$N$_2$O$_9$Na (M+Na)+611.2945, found 611.2927

Compound 34

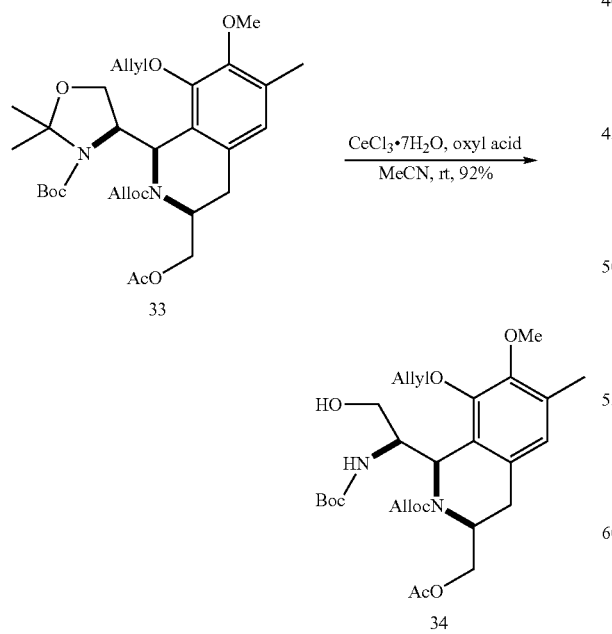

A solution of compound 33 (2.94 g, 5 mmol), CeCl$_3$·7H$_2$O (3.8 g, 2 equiv) and oxalic acid (23 mg, 0.05 equiv) in acetonitrile (25 ml) was stirred at room temperature for 3 hours. The reaction was quenched by adding solid sodium hydrogen carbonate at 0° C. and stirred for another 10 min. The reaction mixture was diluted with dichloromethane (500 ml) and filtered. The filtrate was concentrated under reduced pressure and the residue was purified by flash column chromatography (33% EtOAc in heptane) to afford alcohol 34 (2.52 g, 92%) as colorless oil. [α]$_D^{25.8}$-21.3° (c=0.65, CHCl$_3$). IR (neat film) ν3436, 2934, 1743, 1694, 1503, 1454 1400, 1308, 1280, 1230, 1169, 1057, 995, 932 cm$^{-1}$; $^1$H NMR (300 MHz, CDCl$_3$) δ 6.72 (s, 1H), 6.16-5.81 (m, 2H), 5.69-5.61 (m, 1H), 5.46-5.81 (m, 5H), 4.70-4.37 (m, 4H), 4.30-3.82 (m, 3H), 3.78 & 3.745 (s, 3H), 3.68-3.54 (m, 1H), 3.21 & 3.02 (dd, J=15.1, 12.7 Hz, 1H), 2.75 (dd, J=15.5, 6.1 Hz, 1H), 2.20 (s, 3H), 2.10 & 2.08 (s, 3H), 1.18 & 1.07 (s, 9H); $^{13}$C NMR (75 MHz, CDCl$_3$) δ 170.75, 170.49, 157.66, 155.33, 154.23, 149.89, 149.22, 148.53, 147.86, 134.04, 132.03, 131.63, 129.88, 129.47, 126.80, 124.53, 123.95, 119.47, 118.65, 117.63, 78.95, 78.74, 73.53, 67.22, 66.93, 65.54, 64.75, 62.07, 60.18, 60.01, 54.66, 53.67, 52.21, 50.32, 49.91, 29.67, 28.16, 27.78, 20.91, 20.74, 15.65; HRMS (ESI$^+$) m/z: Calc. for C$_{29}$H$_{40}$N$_2$O$_9$Na (M+Na)$^+$ 571.2632, found 571.2633.

Compound 12

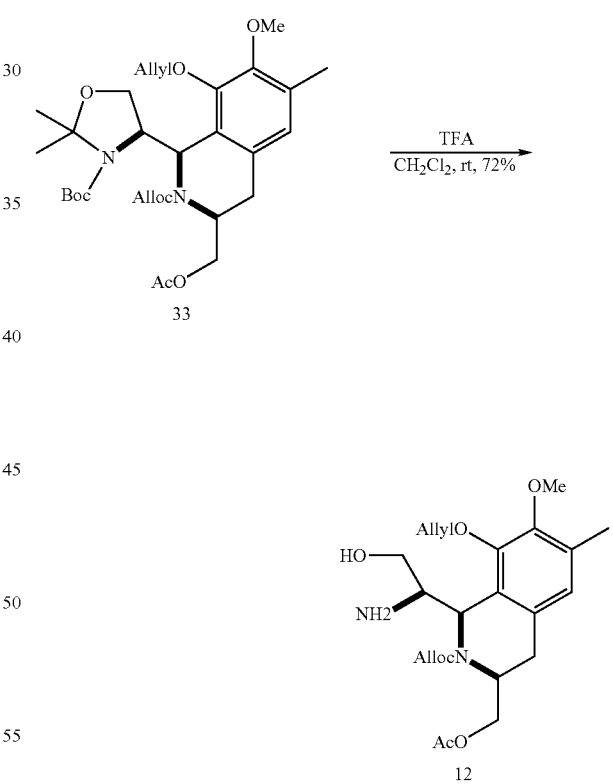

Method A: A solution of ester 33 (2.94 g, 5 mmol) in dichloromethane and trifluoroacetic acid (6:1, v/v, 20 ml) was stirred at room temperature for 4 hours. The mixture was diluted with dichloromethane (500 ml) and washed with saturated aqueous sodium hydrogen carbonate solution, brine, dried over sodium sulfate and evaporated to dryness under reduced pressure. The residue was purified by flash column chromatography (5% MeOH in dichloromethane) to afford amino alcohol 12 (1.61 g, 72%) as colorless oil.

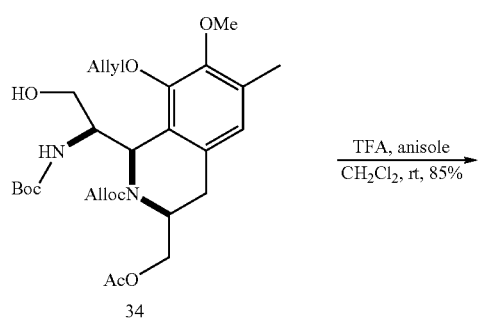

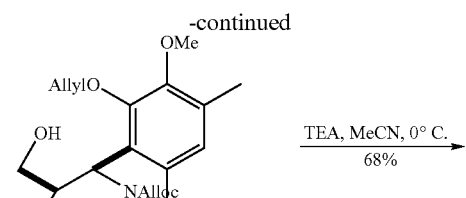

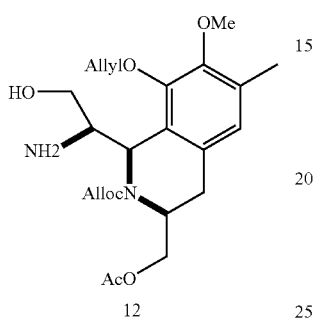

Method B: A solution of alcohol 34 (2.74 g, 5 mmol) and anisole (5.4 ml, 10 equiv) in dichloromethane and trifluoroacetic acid (8:1, v/v, 20 ml) was stirred at room temperature for 10 hours. The mixture was diluted with dichloromethane (500 ml) and washed with saturated aqueous sodium hydrogen carbonate solution, brine, dried over sodium sulfate and evaporated to dryness under reduced pressure. The residue was purified by flash column chromatography (5% MeOH in dichloromethane) to afford amino alcohol 12 (1.9 g, 85%) as colorless oil. $[\alpha]_D^{23.1}$ -19.7° (c=0.8, CHCl$_3$). IR (neat film) $\nu$ 3375, 2941, 1741, 1692, 1460, 1398, 1309, 1235, 1070, 995, 933 cm$^{-1}$; $^1$H NMR (500 MHz, CDCl$_3$) $\delta$ 6.77 (s, 1H), 6.07 & 5.90 (m, 2H), 5.20-5.52 (m, 5H), 4.03-4.71 (m, 7H), 3.81 (s, 3H), 3.50-3.79 (m, 2H), 2.69-3.06 (m, 3H), 2.27 (s, 3H), 2.07 (s, 3H); $^{13}$C NMR (75 MHz, CDCl$_3$) $\delta$ 170.78, 157.39, 149.90, 148.45, 133.85, 132.36, 132.17, 131.93, 129.48, 127.74, 125.03, 118.82, 118.50, 118.30, 118.01, 73.84, 67.08, 66.80, 65.71, 64.90, 64.01, 63.58, 60.14, 55.40, 53.38, 52.79, 52.04, 29.82, 20.81, 15.77; HRMS (ESI$^+$) m/z: Calc. for C$_{23}$H$_{33}$N$_2$O$_7$ (M+H)$^+$ 449.2632, found 449.2633.

Compound 37

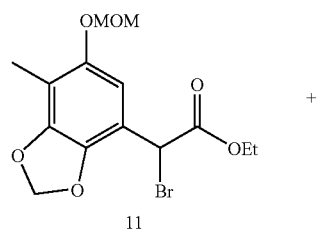

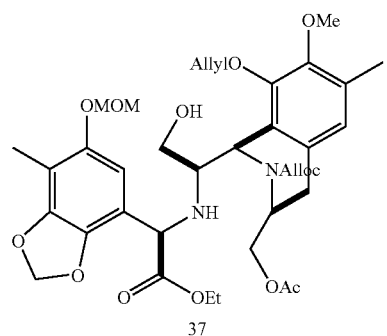

A solution of bromide 12 (2.35 g, 5.25 mmol), amine 12 (1.80 g, 5 mmol) and triethyl amine (1.4 ml, 10 mmol) in acetonitrile (30 ml) was stirred at 0° C. for 14 hours. The reaction mixture was concentrated under reduced pressure and the residue was purified by flash column chromatography (25% EtOAc in heptane) to afford coupled product 37 (2.54 g, 68%) as colorless oil. $[\alpha]_D^{23.6}$ -39.6° (c=1.0, CHCl$_3$). IR (neat film) $\nu$ 3475, 2933, 2358, 1738, 1694, 1453, 1428, 1325, 1308, 1232, 1111, 1055, 992, 932 cm$^{-1}$; $^1$H NMR (500 MHz, CDCl$_3$) $\delta$ 6.82 (s, 1H), 6.16 & 6.11 (s, 1H), 6.11-6.16 (m, 1H), 6.0-6.11 (m, 1H), 5.84 (s, 1H), 5.82 (s, 1H), 5.39-5.59 (m, 2H), 5.16-5.30 (m, 3H), 5.06 (d, J=6.6 Hz, 1H), 5.00 (d, J=6.6 Hz, 1H), 4.65-4.74 (m, 1H), 4.49-4.62 (m, 2H), 4.31-4.48 (m, 2H), 3.90-4.20 (m, 4H), 3.74 (bs, 3H), 3.52-3.66 (m, 1H), 3.42 (bs, 3H), 3.27-3.49 (m, 2H), 3.20 & 3.05 (s, 1H), 3.04 (t, J=14.0 Hz, 1H), 2.84 & 2.71 (bs, 2H), 2.48 (bs, 1H), 2.26 (s, 3H), 2.04 (s, 3H), 1.66 & 1.69 (s, 3H), 1.07 (t, J=7.0 Hz, 3H); $^{13}$C NMR (75 MHz, CDCl$_3$) $\delta$ 171.01, 156.47, 155.45, 151.03, 149.86, 148.03, 147.68, 146.75, 139.80, 133.89, 132.38, 132.03, 130.20, 128.43, 127.93, 125.31, 125.02, 118.22, 117.49, 117.31, 116.50, 110.45, 107.31, 101.11, 95.35, 73.74, 66.64, 65.22, 64.17, 63.50, 61.11, 59.95, 59.46, 57.24, 55.96, 52.79, 52.79, 52.12, 51.80, 29.17, 28.82, 19.81, 15.94, 13.99, 8.84; HRMS (ESI$^+$) m/z: Calc. for C$_{37}$H$_{48}$N$_2$O$_{13}$Na (M+Na)$^+$ 751.3054, found 751.3069.

Compound 38

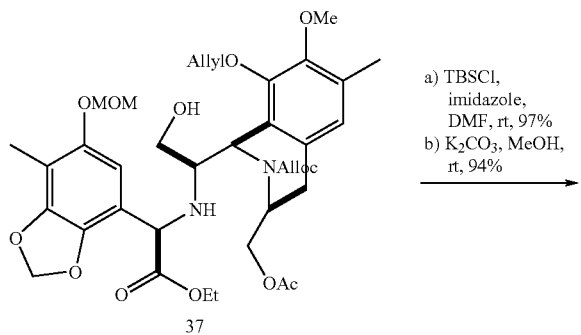

A solution of alcohol 37 (3.64 g, 5 mmol), imidazole (1.02 g, 3 equiv) and TBSCl (1.13 g, 1.5 equiv) in DMF (15 ml) was stirred at 23° C. for 3 hours. The reaction mixture was diluted with diethyl ether (1000 ml), washed with water and brine, dried with sodium sulfate. After removal of the volatile, the residue was purified by flash column chromatography (20% EtOAc in heptane) to afford silyl ether of 37 (4.08 g, 97%) as colorless oil. $[\alpha]_D^{3\ 2.8}$-36.5° (c=1.0, CHCl$_3$). IR (neat film) v 2929, 1742, 1696, 1461, 1396, 1306, 1234, 1111, 1058, 993, 935, 837 cm$^{-1}$; $^1$H NMR (300 MHz, CDCl$_3$) δ 6.77 (s, 1H), 6.33 (s, 1H), 6.00-6.19 (m, 1H), 5.80-5.94 (m, 1H), 5.81 (bs, 1H), 5.77 (d, J=1.1 Hz, 1H), 5.66 (d, J=10.2 Hz, 1H), 5.32 (dd, J=17.0, 1.5 Hz, 1H),), 5.22-5.31 (m, 1H), 5.14 (t, J=10.2 Hz, 2H), 4.99 (t, J=6.4 Hz, 2H), 4.42-4.66 (m, 4H), 4.21-4.39 (m, 2H), 4.00-4.13 (1H, m), 3.83-3.99 (m, 3H), 3.76 (s, 3H), 3.64-3.74 (m, 2H), 3.41 (s, 3H), 2.91-3.03 (m, 2H), 2.74 (dd, J=15.4, 6.7 Hz, 1H), 2.36 (m, 1H), 2.24 (s, 3H), 2.04 (s, 3H), 1.82-1.94 (m, 1H), 1.80 & 1.67 (s, 3H), 1.05 (t, J=7.0 Hz, 3H), 0.90 (s, 9H), 0.06 (s, 6H); $^{13}$C NMR (75 MHz, CDCl$_3$) δ 171.58, 170.79, 156.15, 150.92, 149.86, 148.42, 146.19, 140.12, 134.67, 132.72, 131.26, 130.14, 128.76, 124.72, 117.80, 116.95, 116.77, 110.14, 106.36, 100.79, 95.82, 66.37, 65.27, 64.74, 60.62, 59.91, 58.14, 56.14, 52.89, 51.38, 29.39, 26.00, 20.33, 18.44, 15.86, 13.93, 8.88, -5.40; HRMS (ESI$^+$) m/z: Calc. for C$_{43}$H$_{62}$N$_2$O$_{13}$NaSi (M+Na)$^+$ 865.3919, found 865.3905. A solution of TBS ether of 37 (2.52 g, 3 mmol) and potassium carbonate (0.828 g, 2 equiv) in methanol (15 ml) was stirred at 23° C. for 2 hours. The reaction mixture was diluted with dichloromethane (500 ml), washed with water and brine, dried with sodium sulfate and evaporated to dryness. The residue was purified by flash column chromatography (33% EtOAc in heptane) to afford alcohol 38 (2.25 g, 94%) as colorless oil. $[\alpha]_D^{2\ 3.5}$-27.5° (c=1.0, CHCl$_3$). IR (neat film) v 3409, 2930, 1738, 1695, 1399, 1307, 1255, 1111, 1059, 994, 926, 837 cm$^{-1}$; $^1$H NMR (300 MHz, CDCl$_3$) δ 6.78 (s, 1H), 6.28 (s, 1H), 5.97-6.17 (m, 1H), 5.87 (s, 1H), 5.83 (s, 1H), 5.59-5.95 (m, 2H), 5.35 (d, J=17.0 Hz, 1H), 5.15 (d, J=9.2 Hz, 1H), 5.02 (bs, 2H), 4.37-4.67 (m, 4H), 4.02-4.18 (m, 2H), 3.75 (s, 3H), 3.73-3.99 (m, 5H), 3.54-3.62 (m, 1H), 3.42 (s, 3H), 3.20-3.45 (m, 2H), 2.93-3.08 (m, 1H), 2.41-2.75 (m, 1H), 2.24 (s, 3H), 2.05 (s, 3H), 1.85 (m, 1H), 1.05 (t, J=7.2 Hz, 3H), 0.80 (s, 9H), 0.02 & -0.01 (s, 6H); $^{13}$C NMR (75 MHz, CDCl$_3$) δ 171.85, 171.41, 156.55, 151.10, 149.51, 147.83, 146.37, 140.03, 134.25, 132.58, 131.46, 127.98, 125.12, 118.08, 117.18, 116.43, 110.26, 106.24, 101.02, 95.76, 95.58, 73.85, 68.39, 66.52, 64.51, 60.87, 59.96, 58.95, 57.64, 56.53, 56.11, 56.05, 53.62, 52.01, 28.71, 26.03, 25.92, 18.52, 15.80, 13.95, 8.89, -5.49, -5.99; HRMS (ESI$^+$) m/z: Calc. for C$_{41}$H$_{60}$N$_2$O$_{12}$NaSi (M+Na)$^+$ 823.3813, found 823.3839.

Aminonitrile 39

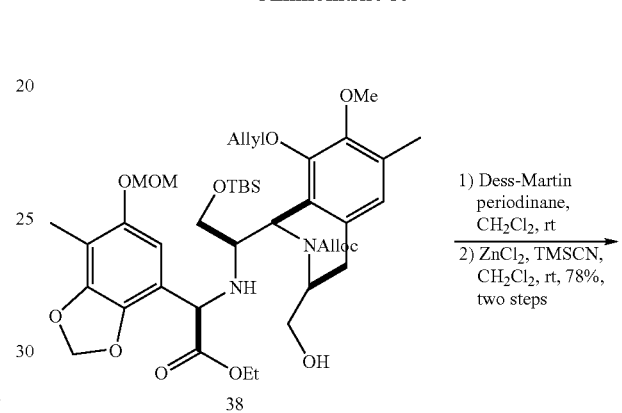

To a solution of alcohol 38 (1.6 g, 2.0 mmol) in anhydrous dichloromethane (10 ml), Dess-Martin periodinane (15 wt. % solution in CH$_2$Cl$_2$, 5.0 ml, 2.4 mmol) was added dropwise, and the resulting mixture was stirred at 23° C. for 20 min. The reaction mixture was diluted with diethyl ether, filtered through a short ped of celite and concentrated. The residue was dissolved in ethyl acetate (500 ml) and washed with saturated aqueous sodium hydrogen carbonate solution, brine, dried over sodium sulfate and evaporated to dryness. To the solution of crude aldehyde in anhydrous dichloromethane (10 ml), TMSCN (0.4 ml, 1.5 equiv) and Zinc chloride (0.5 N in THF, 4.8 ml) were added sequentially. After being stirred at 23° C. for another 10 min, the reaction mixture was diluted with water (50 ml) and extracted with dichloromethane. The combined organic phase was washed with saturated aqueous sodium hydrogen carbonate and dried over sodium sulfate, and concentrated under reduced pressure. The residue was purified by flash column chromatography (16% EtOAc in heptane) to afford aminonitrile 39 (1.26 g, 78%) as colorless oil. $[\alpha]_D^{2\ 3.8}$+36.1° (c=0.93, CHCl$_3$); IR (neat film) v 2930, 1706, 1430, 1313, 1250, 1154, 1113, 1063, 1027, 990, 934, 838 cm$^{-1}$; $^1$H NMR (500 MHz, CDCl$_3$) δ6.45 (bs, 1H), 6.01-6.21 (m, 1H), 6.08 (s, 1H), 5.79-5.93 (m, 1H), 5.76 (s, 1H), 5.57 (s, 1H), 5.47 (t, J=17.0 Hz, 1H), 5.23-5.31 (m, 3H), 5.14 (d, J=10.0 Hz, 1H), 4.99 (s, 1H), 5.02 (d, J=6.0 Hz, 1H), 4.96 (d, J=6.0 Hz, 1H), 4.06-4.67 (m, 8H), 3.88 & 3.91 (bs, 2H), 3.80 & 3.82 (s, 3H), 3.44 (s, 3H), 3.25-3.35 (m, 1H), 2.76-2.90 (m, 1H), 2.19 (s, 3H), 2.11 (s, 3H), 1.85 (dd, J=17.0, 4.4 Hz, 1H), 1.24 (t, J=7.1 Hz, 3H), 0.86 (s, 9H), 0.04 (s, 3H), 0.02 (s, 3H); $^{13}$C NMR (75 MHz, CDCl$_3$) δ 170.76, 170.66, 154.36, 154.27, 150.68, 148.79, 148.59, 147.65, 147.28, 146.59, 140.50, 134.21, 134.15, 132.57, 132.50, 131.32, 130.94, 130.57, 130.46, 126.12, 125.79, 125.17, 124.96, 118.16, 117.77, 117.70, 117.42, 117.35, 114.78, 114.63, 110.97, 107.56, 100.98, 95.60, 95.55, 74.24, 73.97, 66.63, 66.24, 63.37, 60.99, 60.89, 60.81, 60.33, 60.17, 60.09, 59.46, 56.09, 52.84, 50.88, 50.04, 48.83, 48.03, 29.85, 29.66, 29.19, 26.01, 18.52, 15.67, 14.18, 14.12, 8.99, −5.31, −5.44; HRMS (ESI$^+$) m/z: Calc. for C$_{42}$H$_{57}$N$_3$O$_{11}$NaSi (M+Na)$^+$ 830.3660, found 830.3681.

Compound 40

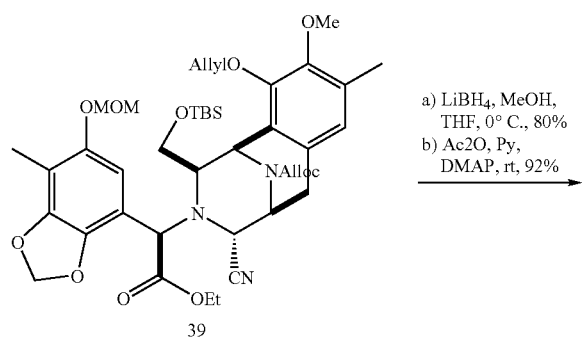

To a solution of LiBH$_4$ (66 mg, 3.0 mmol) and aminonitrile 39 (807 mg, 1.0 mmol) in anhydrous tetrahydrofuran (10 ml), methanol (121 μl, 3.0 mmol) was added dropwise. After being stirred at 0° C. for another 10 hours. The resulting reaction mixture was diluted with ethyl acetate (500 ml), washed with 0.1 N aqueous chlorohydride, saturated aqueous sodium hydrogen carbonate solution, brine, and dried over sodium sulfate. After removal of the volatile under reduced pressure, the residue was purified by flash column chromatography (25% EtOAc in heptane) to afford the primary alcohol (610 mg, 80%) as colorless oil. [α]$_D^{23.3}$+41.7° (c=1.1, CHCl$_3$). IR (neat film) ν 3412, 2928, 2856, 1704, 1427, 1310, 1258, 1113, 1063, 988, 936, 838 cm$^{-1}$; $^1$H NMR (500 MHz, CDCl$_3$) δ6.48 & 6.46 (s, 1H), 6.13 (s, 1H), 5.99-6.26 (m, 1H), 5.78-5.95 (m, 1H), 5.76 (s, 1H), 5.68 (s, 1H), 5.01-5.49 (m, 6H), 4.95 (dd, J=6.4, 13.5 Hz, 2H), 3.92-4.71 (m, 9H), 3.80 & 3.81 (bs, 3H), 3.75-3.88 (m, 1H), 3.44 (s, 3H), 3.38-3.54 (m, 1H), 3.06-3.24 (m, 1H), 2.77-2.94 (m, 1H), 2.20 (s, 3H), 2.10 (s, 3H), 1.86 (d, J=17.0 Hz, 1H), 0.89 (s, 9H), 0.09 & 0.10 (s, 6H); $^{13}$C NMR (75 MHz, CDCl$_3$) δ 154.26, 150.62, 148.90, 148.72, 147.63, 147.26, 146.50, 140.45, 134.28, 134.14, 134.09, 132.51, 132.43, 131.61, 131.21, 130.56, 130.43, 125.92, 125.59, 125.12, 124.87, 118.30, 118.16, 117.87, 117.67, 117.53, 116.72, 116.65, 110.51, 106.70, 100.67, 95.85, 95.80, 74.45, 74.20, 66.72, 66.34, 63.93, 62.15, 62.02, 60.48, 60.16, 60.10, 57.35, 57.24, 56.15, 51.76, 50.10, 49.32, 49.23, 48.57, 30.15, 29.69, 29.48, 26.16, 25.91, 22.68, 18.39, 15.62, 8.97, −5.47, −5.81; HRMS (ESI$^+$) m/z: Calc. for C$_{39}$H$_{55}$N$_2$O$_{10}$Si (M−CN)$^+$ 739.3626, C$_{39}$H$_{54}$N$_2$O$_{10}$NaSi (M−HCN+Na)$^+$ 761.3445, found 739.3666, 761.3486. To a solution of alcohol (1.0 g, 1.3 mmol) in dichloromethane (10 ml), acetic anhydride (1.0 ml), pyridine (2.0 ml) and DMAP (8 mg, 0.05 equiv) were added. After being stirred at 23° C. for half an hour, the volatile was removed under reduced pressure and the residue was purified by flash column chromatography (20% EtOAc in heptane) to afford compound 40 (965 mg, 92%) as colorless oil. [α]$_D^{23.5}$+51.1° (c=1.0, CHCl$_3$). IR (neat film) ν2926, 1741, 1707, 1427, 1309, 1248, 1112, 1065, 989, 935, 837 cm$^{-1}$; $^1$H NMR (300 MHz, CDCl$_3$) δ 6.48 & 6.47 (s, 1H), 6.26 (s, 1H), 6.01-6.21 (m, 1H), 5.79-5.93 (m, 1H), 5.68 (s, 1H), 5.43 (s, 1H), 5.12-5.48 (m, 5H), 4.83-5.05 (m, 3H), 4.18-4.70 (m, 8H), 3.82 & 3.80 (bs, 3H), 3.68-3.89 (m, 2H), 3.45 (s, 3H), 3.36-3.48 (m, 1H), 2.76-2.93 (m, 1H), 2.20 (s, 3H), 2.11 (s, 3H), 1.95 (s, 3H), 1.84-1.93 (m, 1H), 0.86 (s, 9H), 0.03 & 0.05 (s, 6H); $^{13}$C NMR (75 MHz, CDCl$_3$) δ 170.31, 154.21, 150.49, 148.90, 148.70, 147.68, 147.31, 146.54, 140.63, 140.38, 134.18, 132.49, 132.42, 131.30, 130.99, 130.54, 130.42, 126.02, 125.69, 125.04, 124.81, 118.29, 118.23, 117.53, 117.39, 116.73, 116.64, 110.48, 107.03, 100.70, 95.95, 95.90, 74.33, 74.07, 66.72, 66.33, 63.45, 61.43, 61.34, 60.19, 60.12, 56.17, 54.98, 54.92, 52.55, 49.96, 49.13, 49.01, 48.23, 30.02, 29.38, 25.88, 20.87, 18.31, 15.62, 8.98, −5.49, −5.78; HRMS (ESI$^+$) m/z: Calc. for C$_{42}$H$_{57}$N$_3$O$_{11}$NaSi (M+Na)$^+$ 830.3660, found 830.3708.

Compound 9

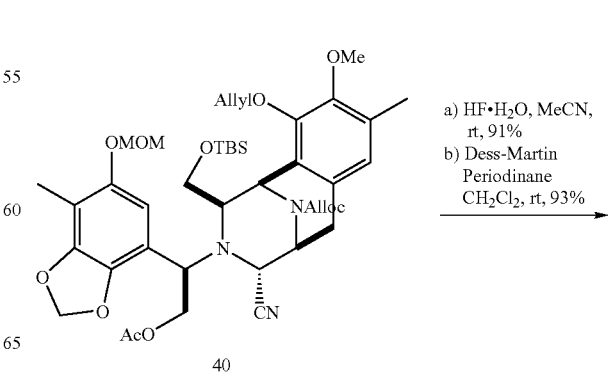

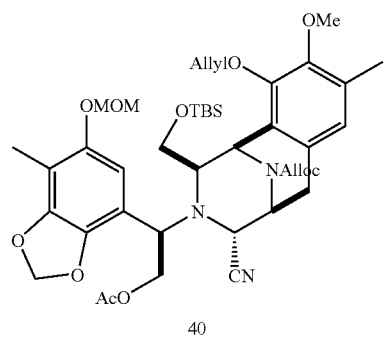

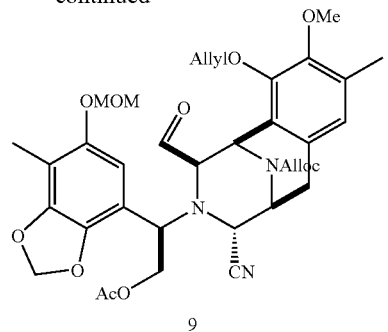

9

To a solution of acetate 40 (1.61 g, 2.0 mmol) in acetonitrile (15 ml), HF (48 wt. % solution in water, 142 μl, 2.0 equiv) was added dropwise at 23° C. Two hours later, the mixture was diluted with dichloromethane (500 ml) and washed with saturated aqueous sodium hydrogen carbonate solution, brine, and dried over sodium sulfate. After evaporation of volatile under reduced pressure, the residue was purified by flash column chromatography (25% EtOAc in heptane) to afford alcohol (1.26 g, 91%) as colorless oil. $[\alpha]_D^{22.9}$ +72.3° (c=1.0, CHCl$_3$). IR (neat film) v3497, 2942, 2356, 1742, 1703, 1486, 1427, 1311, 1235, 1153, 1112, 1060, 985, 935 cm$^{-1}$; $^1$H NMR (300 MHz, CDCl$_3$) δ6.56 & 6.57 (s, 1H), 6.05-6.27 (m, 1H), 5.93 & 5.94 (s, 1H), 5.79-5.96 (m, 1H), 5.77 (s, 1H), 5.59 (bs, 1H), 5.14-5.55 (m, 5H), 4.88 (dd, J=13.1, 6.1 Hz, 2H), 4.25-4.78 (m, 8H), 4.02-4.17 (m, 2H), 3.84 & 3.82 (s, 3H), 3.73-3.89 (m, 2H), 3.41 (s, 3H), 3.20-3.38 (m, 1H), 2.93 (ddd, J=26.0, 17.4, 8.3 Hz, 1H), 2.22 (s, 3H), 2.09 (s, 6H), 1.98 (dd, J=17.2, 6.8 Hz, 1H); $^{13}$C NMR (75 MHz, CDCl$_3$) δ170.47, 154.31, 150.61, 148.43, 148.22, 147.95, 147.55, 146.53, 140.03, 133.07, 132.86, 132.76, 132.43, 132.36, 131.67, 131.23, 131.13, 130.99, 125.91, 125.67, 125.26, 124.81, 120.18, 118.52, 117.77, 117.66, 117.57, 115.51, 110.85, 106.73, 100.92, 95.48, 75.44, 75.21, 66.83, 66.37, 61.75, 61.08, 61.02, 60.52, 60.45, 60.37, 60.26, 56.20, 54.67, 54.56, 52.58, 49.93, 49.06, 48.51, 47.82, 30.24, 29.65, 29.49, 22.65, 20.91, 15.66, 8.96; HRMS (ESI$^+$) m/z: Calc. for C$_{36}$H$_{43}$N$_3$O$_{11}$Na (M+Na)$^+$ 716.2795, found 716.2823. To a solution of alcohol (693 mg, 1 mmol) in anhydrous dichloromethane (10 ml), Dess-Martin reagent (15 wt. % solution in CH$_2$Cl$_2$, 2.5 ml, 1.2 mmol) was added dropwise at room temperature, and the resulting mixture was stirred for another 20 min. The reaction mixture was diluted with diethyl ether, filtered through a short ped of celite and concentrated. The residue was dissolved in ethyl acetate (500 ml) and washed with saturated aqueous sodium hydrogen carbonate solution, brine, and dried over sodium sulfate and evaporated to dryness under reduced pressure. The residue was purified by flash column chromatography (25% EtOAc in heptane) to afford aldehyde 9 (643 mg, 93%) as colorless oil. $[\alpha]_D^2$ 5.2+35.2° (c=1.0, CHCl$_3$). IR (neat film) v 2929, 2355, 1742, 1708, 1487, 1428, 1363, 1316, 1230, 1152, 1112, 1063, 984, 933 cm$^{-1}$; $^1$H NMR (300 MHz, CDCl$_3$) δ9.16 & 9.02 #d=3.2 Hz, 1H), 6.65 & 6.62 (s, 1H), 6.05 (s, 1H), 5.84-6.10 (m, 2H), 5.81 (s, 1H), 5.67 & 5.51 (s, 2H), 5.17-5.38 (m, 4H), 4.87 (t, J=6.7 Hz, 2H), 4.10-4.76 (m, 9H), 3.83 & 3.90 (d, J=1.8 Hz, 1H), 3.74 & 3.73 (s, 3H), 3.40 & 3.47 (s, 3H), 3.09 (ddd, J=26.7, 17.5, 8.4 Hz, 1H), 2.31 (dd, J=17.4, 7.8 Hz, 1H), 2.22 (s, 3H), 2.09 (s, 3H), 2.07 (s, 3H); $^{13}$C NMR (75 MHz, CDCl$_3$) δ 197.46, 196.96, 170.29, 153.84, 150.81, 149.07, 148.89, 146.86, 146.62, 140.52, 133.67, 133.63, 132.27, 132.11, 131.77, 131.61, 130.97, 130.54, 125.11, 124.83, 124.44, 124.27, 118.49, 117.91, 117.62, 117.50, 117.13, 116.89, 114.22, 114.17, 111.33, 111.26, 106.79, 106.57, 101.05, 95.32, 74.01, 73.78, 68.93, 68.83, 66.99, 66.69, 62.44, 60.23, 60.18, 57.87, 57.51, 56.15, 52.59, 52.31, 49.75, 48.86, 47.70, 46.84, 30.07, 29.42, 22.65, 20.81, 15.73, 8.97; HRMS (ESI$^+$) m/z: Calc. For C$_{36}$H$_{41}$N$_3$O$_{11}$Na (M+Na)$^+$ 714.2639, found 714.2672.

Compound 41

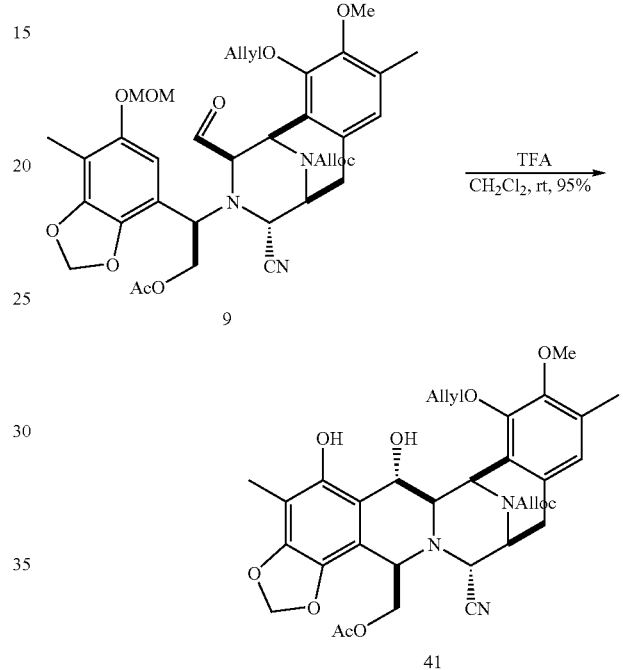

A solution of aldehyde 9 (691 mg, 1.0 mmol)) in trifluoroacetic acid and dichloromethane (1:200, v/v, 50 ml) was stirred at 23° C. for half an hour. The reaction mixture was diluted with dichloromethane (500 ml), washed with saturated aqueous sodium hydrogen carbonate solution and brine, dried with sodium sulfate and evaporated to dryness under reduced pressure. The residue was purified by flash column chromatography (25% EtOAc in heptane) to afford compound 41 (615 mg, 95%) as colorless oil. $[\alpha]_D^2$ $^{7.9}$+46.3° (c=1.0, CHCl$_3$). IR (neat film) v3282, 2924, 1740, 1707, 1432, 1415, 1262, 1226, 1105, 1012 cm$^{-1}$; $^1$H NMR (300 MHz, CDCl$_3$) δ 9.71 & 9.65 (s, 1H), 6.74 (s, 1H), 6.08-6.30 (m, 1H), 6.10 (dd, J=13.0, 4.2 Hz, 1H), 5.90 (d, J=1.0 Hz, 1H), 5.80-5.97 (m, 1H), 5.82 (d, J=0.9 Hz, 1H), 5.10-5.69 (m, 5H), 4.89-4.29 (m, 7H), 4.14-4.03 (m, 2H), 3.82 & 3.81 (s, 3H), 3.60-3.69 (m, 1H), 3.28-3.12 (m, 2H), 2.77 (dd, J=17.7, 8.1 Hz, 1H), 2.22 (s, 3H), 2.08 (s, 3H), 1.51 & 1.54 (s, 3H); $^{13}$C NMR (75 MHz, CDCl$_3$) δ 170.11, 154.29, 154.15, 149.41, 149.35, 148.48, 148.43, 148.22, 147.39, 146.96, 145.84, 135.37, 135.29, 134.60, 133.77, 132.67, 132.48, 132.25, 132.18, 132.07, 132.01, 131.59, 131.15, 127.05, 126.88, 124.29, 123.87, 121.46, 118.75, 117.93, 116.12, 116.01, 115.95, 110.14, 110.03, 107.96, 100.96, 76.22, 75.94, 69.03, 67.01, 66.66, 64.35, 64.05, 63.29, 61.57, 61.44, 60.87, 60.60, 59.03, 58.89, 57.93, 56.40, 49.32, 48.40, 47.10, 46.37, 30.22, 29.68, 22.66, 20.21, 15.62, 8.53; HRMS (ESI+) m/z: Calc. for C$_{34}$H$_{37}$N$_3$O$_{10}$Na (M+Na)+ 670.2377, found 670.2406.

Compound 42

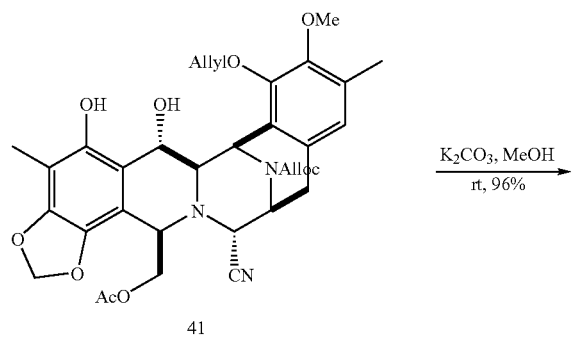

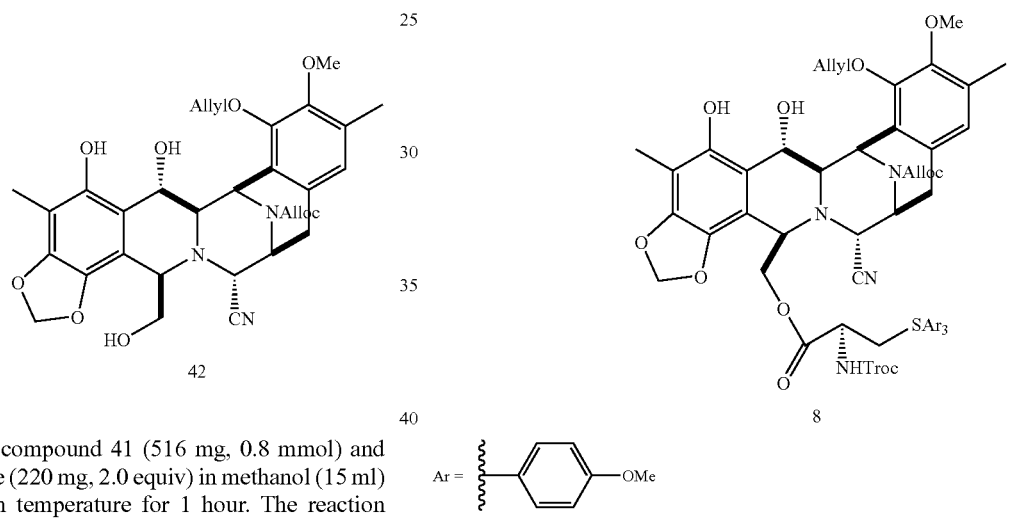

A suspension of compound 41 (516 mg, 0.8 mmol) and potassium carbonate (220 mg, 2.0 equiv) in methanol (15 ml) was stirred at room temperature for 1 hour. The reaction mixture was diluted with dichloromethane (500 ml), washed with 10% citric acid, saturated aqueous sodium hydrogen carbonate solution, brine, and dried with sodium sulfate and evaporated to dryness under reduced pressure. The residue was purified by flash column chromatography (50% EtOAc in heptane) to afford diols 42 (465 mg, 96%) as colorless oil. [α]$_D^{28.2}$ +52.2° (c=0.9, CHCl$_3$). IR (neat film) ν3290, 2925, 2358, 1703, 1433, 1415, 1335, 1314, 1266, 1228, 1107, 1057, 1011, 965, 937 cm$^{-1}$; $^1$H NMR (300 MHz, CDCl$_3$) δ9.60 & 9.54 (s, 1H), 6.77 (s, 1H), 6.09-6.31 (m, 1H), 5.87 (d, J=1.2 Hz, 1H), 5.84-5.97 (m, 2H), 5.80 (d, J=1.0 Hz, 1H), 5.74 & 5.67 (bs, 1H), 5.52 (dd, J=22.0, 17.4 Hz, 1H), 5.41 (dd, J=10.1, 4.3 Hz, 1H), 5.27 (dd, J=15.7, 14.1 Hz, 1H), 5.21 (d, J=10.1 Hz, 1H), 4.75-4.91 (m, 2H), 4.50-4.71 (m, 3H), 4.30-4.41 (m, 2H), 4.23 (bs, 1H), 3.97 (t, J=4.0 Hz, 1H), 3.83 & 3.82 (s, 3H), 3.59 (d, J=10.2 Hz, 1H), 3.19-3.32 (m, 3H), 2.77 (dd, J=17.7, 7.3 Hz, 1H), 2.22 (s, 3H), 2.05 (s, 3H); $^{13}$C NMR (75 MHz, CDCl$_3$) δ 154.29, 154.18, 149.47, 149.38, 148.80, 148.64, 147.12, 145.88, 135.37, 132.70, 132.51, 132.23, 132.10, 132.03, 130.75, 130.30, 126.71, 126.52, 124.23, 123.80, 121.52, 118.82, 118.00, 115.96, 115.87, 110.44, 109.73, 109.60, 107.82, 100.87, 76.15, 75.89, 68.94, 67.08, 66.71, 65.37, 65.32, 61.58, 60.64, 59.34, 58.31, 49.40, 48.48, 47.26, 46.53, 30.64, 30.07, 22.63, 15.77, 8.49; HRMS (ESI+) m/z: Calc. for C$_{32}$H$_{35}$N$_3$O$_9$Na (M+Na)+ 628.2271, found 628.2319.

Compound 8

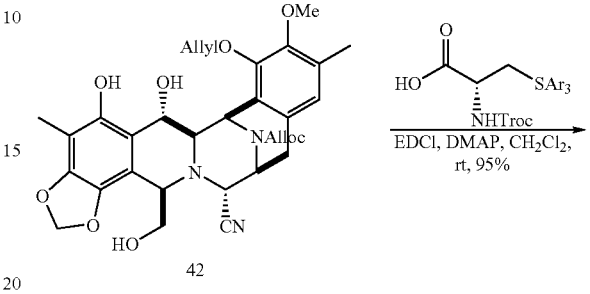

A solution of diols 42 (650 mg, 1.07 mmol), (S)—N-Troc-S-tris(4-methoxyphenyl)methane cysteine (2.02 g, 3.21 mmol), DMAP (261 mg, 2.14 mmol), and EDCl (1.02 g, 5.35 mmol) in anhydrous dichloromethane (8 ml) was stirred at room temperature for 1 hour. The reaction mixture was diluted with dichloromethane (500 ml), washed with saturated aqueous sodium hydrogen carbonate solution and brine, dried over sodium sulfate and evaporated to dryness under reduced pressure. The residue was purified by flash column chromatography (25% EtOAc in heptane) to afford ester 8 (1.23 g, 95%) as a white film. [α]$_D^{29.2}$ +28.4° (c=1.0, CHCl$_3$). IR (neat film) ν3293, 2921, 1741, 1604, 1503, 1440, 1250, 1224, 1177, 1101, 1032, 771 cm$^{-1}$; $^1$H NMR (500 MHz, CDCl$_3$) δ9.62 & 9.57 (s, 1H), 7.21 (d, J=8.0 Hz, 6H), 6.80 (d, J=8.1 Hz, 6H), 6.68 (s, 1H), 6.10-6.28 (m, 1H), 6.06 (dd, J=20.1, 3.8 Hz, 1H), 5.91 (s, 1H), 5.83-5.94 (m, 1H), 5.77 (s, 1H), 5.66 & 5.58 (s, 1H), 5.56 & 5.48 (d, J=17.4 Hz, 1H), 5.40 (t, J=10.1 Hz, 1H), 5.18-5.31 (m, 2H), 5.12 (d, J=8.5 Hz, 1H), 4.46-4.84 (m, 7H), 4.32-4.40 (m, 2H), 4.04-4.22 (m, 2H), 3.83 & 3.80 (s, 3H), 3.78 (s, 9H), 3.71-3.87 (m, 1H), 3.06-3.24 (m, 2H), 2.77 (t, J=16.5 Hz, 1H), 2.42-2.60 (m, 2H), 2.19

(t, J=13.2 Hz, 1H), 2.15 (s, 3H), 2.05 (s, 3H); HRMS (MALDI⁺) m/z: Calc. for $C_{60}H_{61}Cl_3N_4O_{15}NaS$ (M+Na)⁺ 1237.2835, found 1237.2817.

Compound 43

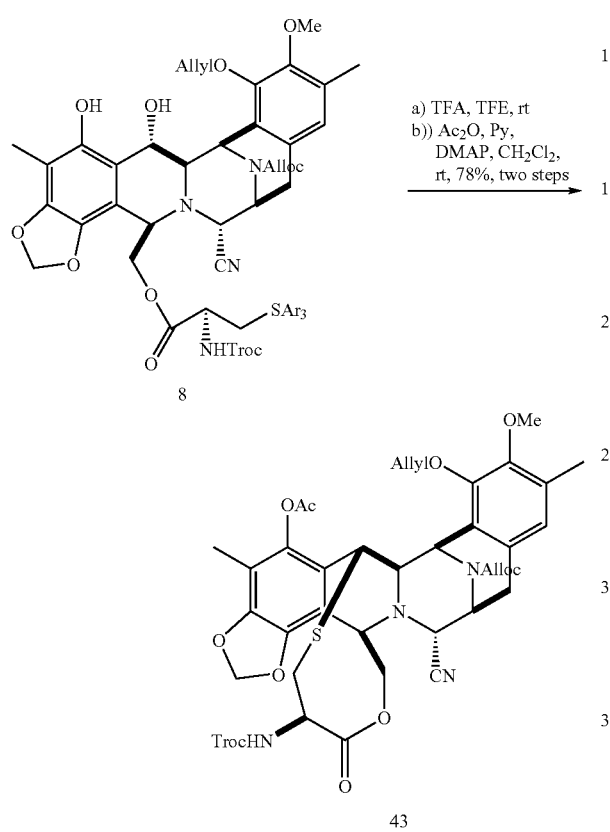

A solution of ester 8 (243 mg, 0.2 mmol)) in trifluoroacetic acid and 2,2,2-trifluoroethanol (1:200, v/v, 20 ml) was stirred at room temperature for three hours. The reaction mixture was diluted with dichloromethane (500 ml), washed with saturated aqueous sodium hydrogen carbonate solution, dried with sodium sulfate. Concentrated under reduced pressure, the residue, free phenol compound, was unstable and directly used for next step. The crude phenol was dissolved in dichloromethane (8 ml), to the solution, acetic anhydride (1.0 ml), pyridine (2.0 ml) and DMAP (1 mg, 0.04 equiv) were added in sequentially. After being stirred at 23° C. for half an hour, the reaction mixture was concentrated under reduced pressure and the residue was purified by flash column chromatography (20% EtOAc in heptane) to afford sulfide 43 (143 mg, 79%) as white film. $[\alpha]_D^{23.5}$ −27.2° (c=1.25, CHCl₃). IR (neat film) ν 3406, 2929, 2359, 1758, 1743, 1710, 1505, 1433, 1333, 1309, 1191, 1101, 1086, 1045, 1002, 914 cm⁻¹; ¹H NMR (300 MHz, CDCl₃) δ 6.82 (s, 1H), 6.04-6.24 (m, 1H), 6.09 (s, 1H), 5.99 (s, 1H), 5.75-5.94 (m, 1H), 5.46-5.56 (m, 2H), 5.27 (d, J=12.0 Hz, 1H), 5.22 (d, J=15.8 Hz, 1H), 5.16 (t, J=10.5 Hz, 1H), 4.93-5.07 (m, 3H), 4.70-4.84 (m, 2H), 4.45-4.68 (m, 4H), 4.16-4.39 (m, 4H), 3.82 & 3.79 (s, 3H), 3.76 (m, 1H), 3.41 (m, 1H), 3.11-3.17 (m, 2H), 2.30-2.37 (m, 1H), 2.29 (s, 3H), 2.27 (s, 3H), 2.15 (d, J=15.8 Hz, 1H), 2.03 (s, 3H); ¹³C NMR (75 MHz, CDCl₃) δ 166.99, 169.84, 168.64, 154.08, 153.96, 149.29, 149.09, 148.89, 148.83, 146.03, 141.07, 140.46, 134.77, 134.66, 134.54, 132.55, 132.43, 132.32, 32.17, 130.46, 130.08, 127.50, 127.09, 125.18, 124.98, 119.64, 118.50, 117.75, 116.17, 113.83, 113.75, 112.87, 112.79, 102.14, 95.41, 74.69, 7451, 73.45, 73.19, 66.92, 66.58, 61.43, 60.42, 59.51, 59.42, 59.32, 58.35, 58.25, 57.61, 57.55, 54.43, 48.43, 47.56, 47.56, 47.09, 41.48, 32.49, 27.80, 27.27, 20.40, 15.90, 9.62; HRMS (MALDI⁺) m/z: Calc. for $C_{40}H_{41}Cl_3N_4O_{12}NaS$ (M+Na)⁺ 929.1445, found 929.1404.

Compound 6

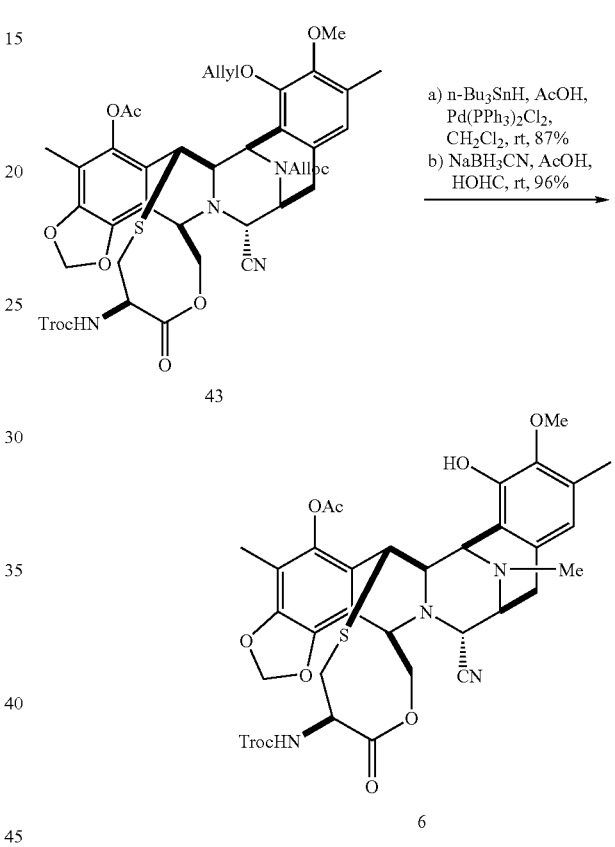

A suspension of compound 43 (133 mg, 0.147 mmol), acetic acid (0.193 ml, 3.38 mmol), tri-n-butyltin hydride (0.395 ml, 1.47 mmol) and Pd (PPh₃)₂Cl₂ (43 mg, 0.06 mmol) in anhydrous dichloromethane (5 ml) was stirred at room temperature for 20 min. The reaction mixture was diluted with diethyl ether and filtered through a short ped of celite. The filtrate was concentrated under reduced pressure and the residue was purified by flash column chromatography (33% EtOAc in heptane) to afford amine (100 mg, 87%) as a colorless oil. $[\alpha]_D^{24.1}$ −23.0°(c=1.25, CHCl₃). IR (neat film) ν3370, 2924, 1758, 1503, 1455, 1431, 1372, 1332, 1192, 1100, 1085, 1042, 913 cm⁻¹; ¹H NMR (500 MHz, CDCl₃) δ6.64 (s, 1H), 6.08 (d═1.2 Hz, 1H), 5.98 (d, J=1.3 Hz, 1H), 5.80 (bs, 1H), 5.04 (d, J=2.1 Hz, 1H), 5.01 (s, 1H), 4.81 (d, J=12.1 Hz, 1H), 4.60 (d, J=12.1 Hz, 1H), 4.50-4.54 (m, 1H), 4.47 (d, J=4.9 Hz, 1H), 4.31-4.36 (m, 1H), 4.24 & 4.27 (bs, 1H), 4.19 (bs, 1H), 4.15 (d, J=1.7 Hz, 1H), 3.82 (bd, J=9.2 Hz, 1H), 3.74 & 3.76 (s, 3H), 3.42 (d, J=4.2 Hz, 1H), 2.90-3.05 (m, 2H), 2.35 (d, J=12.0 Hz, 1H), 2.33 (s, 3H), 2.28 (s, 3H), 2.13-2.20 (m, 1H), 2.02 (s, 3H); ¹³C NMR (75 MHz, CDCl₃) δ 169.87, 168.82, 154.13, 145.93, 145.83, 142.81, 141.07, 140.43, 131.18, 130.86, 130.02, 123.89, 121.29, 120.03, 117.98, 113.53, 113.30, 102.07, 95.46, 74.70, 74.52, 61.49, 61.28, 60.39, 60.27, 58.93, 58.66, 58.28, 54.40, 48.56, 47.31, 42.04, 41.68, 32.18, 27.71, 20.57, 15.82, 15.62, 9.63; HRMS (MALDI$^+$) m/z: Calc. for $C_{33}H_{34}Cl_3N_4O_{10}S$ (M+H)$^+$ 783.1081, found 783.1061. To a solution of amine (160 mg, 0.205 mmol) and formalin solution (600 μl) in acetonitrile and methanol (1:1, v/v, 6 ml) was added solid sodium cyanoborohydride (64 mg, 1.02 mmol), and the mixture was stirred at 23° C. for half an hour. Acetic acid (0.24 ml, 4.1 mmol) was added dropwise and the resulting mixture was stirred at room temperature for another 1.5 hours. The reaction mixture was partitioned between dichloromethane (200 ml) and saturated aqueous sodium hydrogen carbonate solution (50 ml), and the aqueous layer was further extracted with ethyl acetate (3×100 ml). The combined organic layer was dried over sodium sulfate, concentrated, and the residue was purified by flash column chromatography (33% EtOAc in heptane) to afford 6 (158 mg, 97%) as a colorless oil. $[\alpha]_D^{24.2}$ –32.2° (c=1.2, CHCl$_3$). IR (neat film) ν3397, 2931, 2356, 2340, 1757, 1740, 1503, 1454, 1433, 1371, 1333, 1236, 1192, 1146, 1088, 1046, 1002, 914 cm$^{-1}$; $^1$H NMR (500 MHz, CDCl$_3$) δ6.63 (s, 1H), 6.08 (s, 1H), 5.98 (s, 1H), 5.76 (s, 1H), 5.04 (d, J=10.0 Hz, 1H), 5.02 (d, J=12.0 Hz, 1H), 4.81 (d, J=12.1 Hz, 1H), 4.61 (d, J=12.1 Hz, 1H), 4.52 (m, 1H), 4.15-4.34 (m, 5H), 3.74 & 3.77 (s, 3H), 3.41 (m, 2H), 2.89 (d, J=4.8 Hz, 1H), 2.35-2.38 (m, 1H), 2.34 (s, 3H), 2.28 (s, 3H), 2.19 (s, 3H), 2.13-2.22 (m, 1H), 2.01 (s, 3H); $^{13}$C NMR (75 MHz, CDCl$_3$) δ 169.87, 169.67, 168.66, 154.19, 148.17, 147.89, 145.87, 143.08, 141.01, 140.43, 140.35, 130.67, 130.37, 130.33, 129.87, 120.73, 120.09, 118.05, 117.91, 113.48, 113.42, 102.05, 95.46, 74.71, 74.52, 61.38, 61.15, 60.49, 60.29, 60.17, 59.26, 58.99, 54.52, 54.45, 54.39, 48.82, 41.99, 41.65, 41.47, 32.96, 32.35, 23.82, 23.58, 20.57, 15.87, 15.65, 9.63; HRMS (ESI$^+$) m/z: Calc. for $C_{34}H_{35}Cl_3N_4O_{10}NaS$ (M+Na)$^+$ 819.1037 and 821.1008, found 819.1045 and 821.1028.

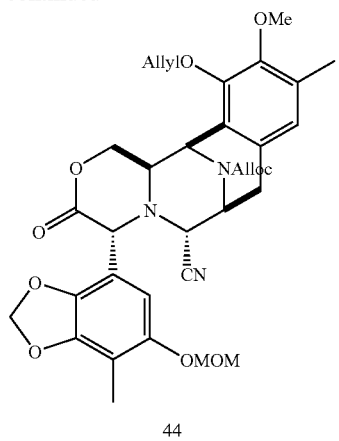

44

To a solution of 39 (16 mg, 0.02 mmol) in acetonitrile (1 ml), HF (48 wt. % solution in water, 1.4 μl, 2.0 equiv) was added dropwise at 23° C. Two hours later, the mixture was diluted with dichloromethane (100 ml), washed with saturated aqueous sodium hydrogen carbonate solution, brine, dried over sodium sulfate and evaporated to dryness under reduced pressure. The residue was purified by preparative TLC (30% EtOAc in heptane) to afford lactone 44 (11 mg, 86%) as colorless oil. $^1$H NMR (300 MHz, CDCl$_3$) δ6.67 (s, 1H), 6.37 (s, 1H), 6.03-6.19 (m, 1H), 5.97 (d, J=3.8 Hz, 2H), 5.80-5.90 (m, 1H), 5.14-5.52 (m, 7H), 5.09 (dd, J=17.4, 6.5 Hz, 2H), 4.30-4.76 (m, 8H), 4.17-4.22 (m, 1H), 3.76-3.88 (m, 6H), 3.46 (s, 3H), 3.16-3.29 (m, 1H), 2.69 (dd, J=24.7, 17.7 Hz, 1H), 2.22 (s, 3H), 2.09 (s, 3H); MS (ESI$^+$) m/z: (M+Na)$^+$ 670.2

Compound 45

Compound 44

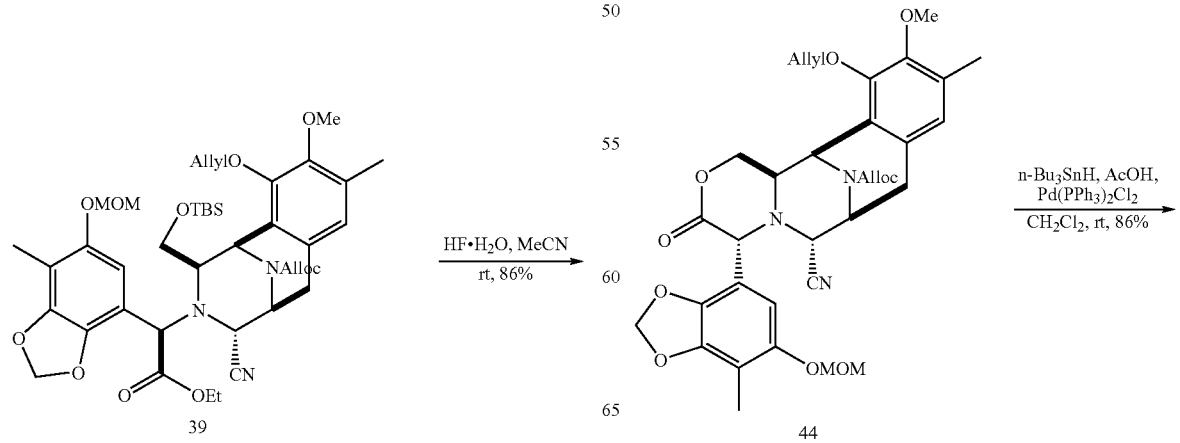

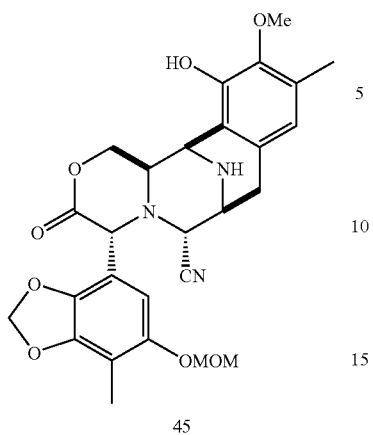

45

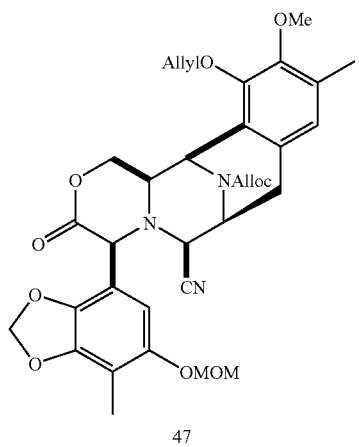

47

To a solution of lactone 44 (10 mg, 0.0155 mmol) in anhydrous dichloromethane (1 ml) were added acetic acid (20 μl, 0.355 mmol, 23 equiv), tri-n-butyltin hydride (39 μl, 0.156 mmol, 10 equiv) and Pd (PPh$_3$)$_2$Cl$_2$ (4 mg, 0.4 equiv). After being stirred at room temperature for 20 min, the reaction mixture was diluted with diethyl ether and filtrated through a short ped of celite. The filtrate was evaporated to dryness under reduced pressure and the residue was purified by preparative TLC (50% EtOAc in heptane) to afford amine alcohol 45 (7 mg, 87%) as a white film. 1H NMR (300 MHz, CDCl$_3$) δ 6.50 (s, 1H), 6.41 (s, 1H), 5.98 (d=2.2 Hz, 2H), 5.78 (bs, 1H), 5.11 (dd, J=9.5, 6.6 Hz, 2H), 4.69 (dd, J=12.0, 4.4 Hz, 1H), 4.66 (s, 1H), 4.33 (d, J=2.8 Hz, 1H), 4.07 (dd, J=12.0, 8.3 Hz, 1H), 3.91 (m, 1H), 3.77 (s, 3H), 3.69 (m, 1H), 3.55 (d, J=8.4 Hz, 1H), 3.47 (s, 3H), 3.11 (dd, J=17.7, 8.2 Hz, 1H), 2.68 (d, J=17.8 Hz, 1H), 2.26 (s, 3H), 2.11 (s, 3H); HRMS (ESI$^+$) m/z: Calc. for C$_{27}$H$_{29}$N$_3$O$_8$Na (M+Na)$^+$ 546.1852, found 546.1868.

To a solution of 46 (16 mg, 0.02 mmol) in THF (1 ml), TBAF (1.0 M solution in THF, 22 μl, 1.1 equiv) was added dropwise and the mixture was stirred at 23° C. for 20 min. The reaction mixture was diluted with ethyl acetate (100 ml), washed with water, brine, and dried over sodium sulfate. Concentrated under reduced pressure, the residue was purified by preparative TLC (25% EtOAc in heptane) to afford lactone 47 (11.3 mg, 87%) as colorless oil. $^1$H NMR (300 MHz, CDCl$_3$) 6.21 (s, 1H), 6.02-6.17 (m, 1H), 5.81-5.93 (m, 1H), 5.84 (s, 1H), 5.80 (s, 1H), 5.19-5.55 (m, 5H), 5.00 (d, J=6.5 Hz, 1H), 4.91 (d, J=6.5 Hz, 1H), 4.78 & 4.85 (d, J=8.5 Hz, 1H), 4.32 & 4.44 (dd, J=12.0, 5.7 Hz, 1H), 3.81-3.82 (s, 3H), 3.67-3.83 (m, 2H), 3.56 (m, 1H), 3.41 (s, 3H), 3.14 (m, 1H), 2.53 (dd, J=17.1, 14.0 Hz, 1H), 2.22 (s, 3H), 2.07 (s, 3H); HRMS (ESI$^+$) m/z: Calc. for C$_{34}$H$_{37}$N$_3$O$_{10}$Na (M+Na)$^+$ 670.2377, found 670.2360.

Compound 47

Compound 48

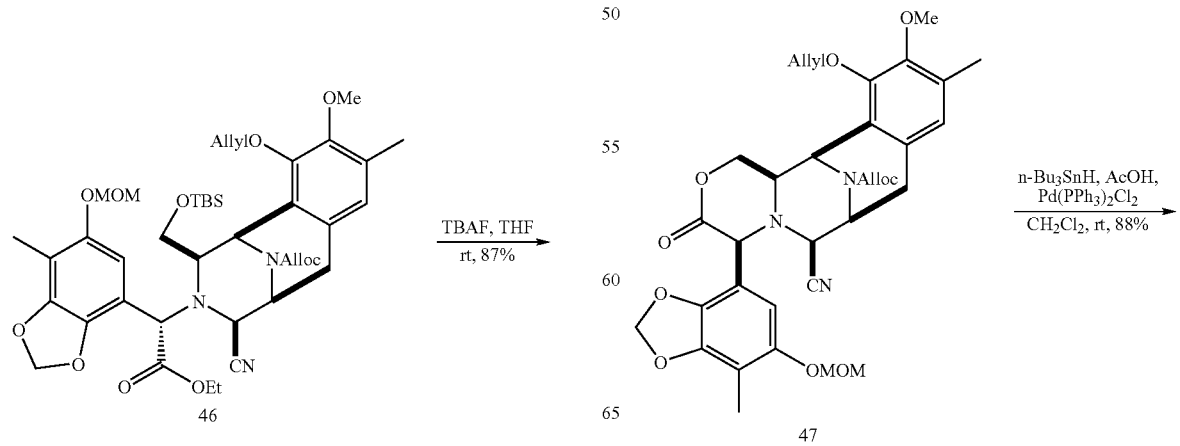

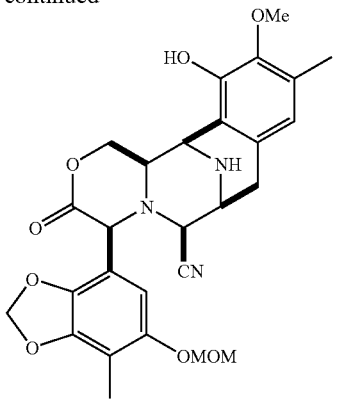

48

Following the same procedure detailed for the preparation of 45, Compound 48 was isolated by preparative TLC (50% EtOAc in heptane) in 88% yield as a white film. $^1$H NMR (500 MHz, CDCl$_3$) 6.47 (s, 1H), 6.24 (s, 1H), 5.84 (d, J=1.0 Hz, 1H), 5.81 (d, J=1.0 Hz, 1H), 5.76 (bs, 1H), 4.95 (dd, J=23.0, 6.4 Hz, 2H), 4.63 (dd, J=11.5, 2.9 Hz, 1H), 4.55 (s, 1H), 4.41 (d, J=2.9 Hz, 1H), 3.83 (d, J=11.3 Hz, 1H), 3.78 (s, 3H), 3.65 (bd, J=7.8 Hz, 1H), 3.64 (s, 1H), 3.57 (dt, J=10.8, 3.0 Hz, 1H), 3.42 (s, 3H), 3.01 (dd, J=17.6, 8.6 Hz, 1H), 2.51 (d, J=17.7 Hz, 1H), 2.27 (s, 3H), 2.07 (s, 3H); MS (ESI$^+$) m/z: (M+Na)$^+$ 546.1

Morpholinone 50

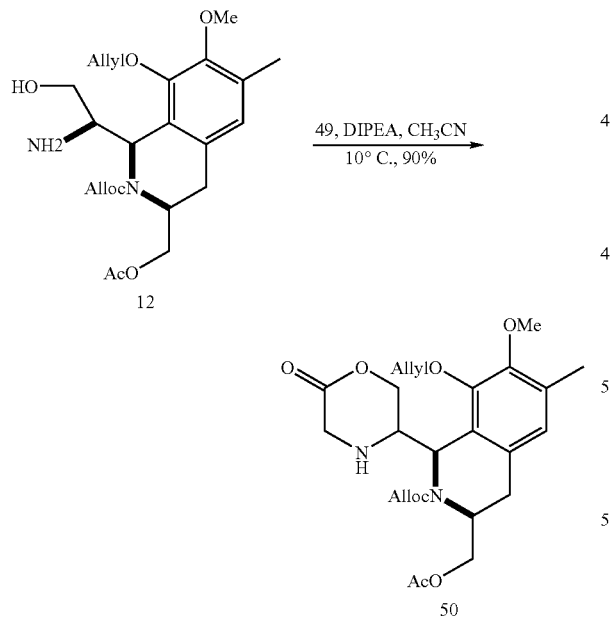

To a mixture of amino alcohol 12 (204 mg, 0.46 mmol) and DIPEA (147 mg, 200 μL, 1.14 mmol) in anhydrous acetonitrile (2.5 ml) was added a solution of BrCH$_2$CO$_2$Ph (49) (110 mg, 0.50 ml) in anhydrous acetonitrile (0.5 ml) dropwise at 10° C. After being stirred at this temperature for 4 h, the resulting mixture was concentrated in vacuum below 30° C. The residue was purified by flash column chromatography (40% EtOAc in heptane) to afford morpholinone 50 (199 mg, 0.41 mmol, 90%) as a pale yellow oil. [α]$_D^{23}$ −47 (c=1.0, CHCl$_3$); IR (neat) ν 3323, 2938, 1737, 1693, 1394, 1305, 1226, 1068, 993 cm$^{-1}$; $^1$H NMR (500 MHz, CDCl$_3$) δ 6.81 (s, 1H), 6.10 (m, 1H), 5.95 (m, 1H), 5.61 (m, 1H), 5-3.4 (m, 2H), 4.6-4.75 (m, 4H), 4.4-4.6 (m, 3H), 4.30 (dd, J=11.4, 2.1 Hz, 1H), 4.13 (t, J=7.1 Hz, 1H), 3.84 (s, 3H), 3.80 (d, J=18.4 Hz, 1H), 3.53 (d, J=18.3 Hz, 1H), 3.44 (dt, J=9.8, 3.4 Hz, 1H), 3.06 (br.t, J=15.2 Hz, 1H), 2.83 (dd, J=15.5, 6.6 Hz, 1H), 2.28 (s, 3H), 2.12 (s, 3H); $^{13}$C NMR (75 MHz, CDCl$_3$) δ 170.6, 168.4, 155.6, 149.7, 148.2, 133.9, 132.5, 132.2, 129.4, 126.2, 125.4, 118.6, 118.1, 74.0, 72.6, 66.9, 64.9, 60.1, 54.3, 52.5, 51.4, 47.2, 29.5, 20.9, 15.8; HRMS (ESI$^+$) m/z: Calc. for C$_{25}$H$_{32}$N$_2$O$_8$ Na (M+Na)$^+$ 511.2056, found 511.2041.

Compound 51

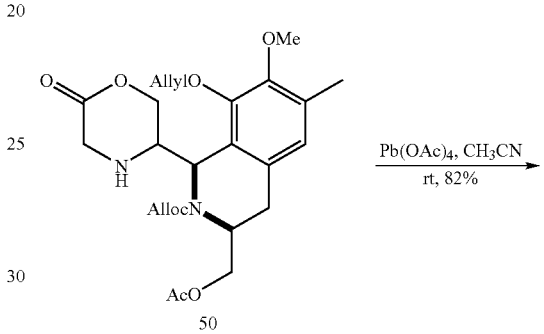

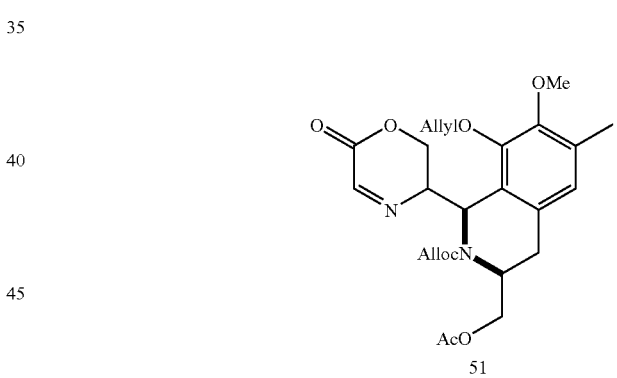

51

To a solution of morpholinone 50 (188 mg, 0.39 mmol) in anhydrous acetonitrile (4.0 ml) was added Pb(OAc)$_4$ (188 mg, 0.42 ml). After being stirred at room temperature for 30 min, the reaction was quenched with pinacol (11 mg, 0.09 mmol) and filtered through a short pad of Celite. The filtrate was evaporated to dryness and the residue was purified by flash column chromatography (25% EtOAc in heptane) to afford imino lactone 51 (158 mg, 0.32 mmol, 82%) as a colorless oil. [α]$_D^{23}$ −71 (c=1.0, CHCl$_3$); IR (neat) ν 2938, 1741, 1699, 1394, 1309, 1232, 1074, 994 cm$^-$; $^1$H NMR (500 MHz, CDCl$_3$) δ 7.76 (d=2.6 Hz, 1H), 6.78 (s, 1H), 5.8-6.2 (m, 2H), 5.73 (br.s, 1H), 5.1-5.4 (m, 4H), 4.4-4.7 (m, 7H), 4.30 (dd, J=11.4, 2.3 Hz, 1H), 4.1-4.2 (m, 2H), 3.78 (s, 3H), 3.13 (dd, J=15.4, 13.1 Hz, 1H), 2.85 (dd, J=15.6, 6.6 Hz, 1H), 2.24 (s, 3H), 2.09 (s, 3H); $^{13}$C NMR (75 MHz, CDCl$_3$) δ 170.6, 155.5, 154.4, 152.9, 149.7, 148.1, 134.1, 132.4, 132.2, 129.3, 126.2, 124.9, 118.4, 117.3, 73.4, 68.3, 66.9, 65.0, 60.2, 59.3, Compound 53

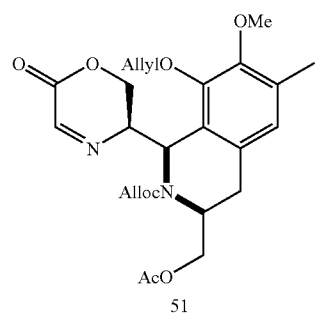

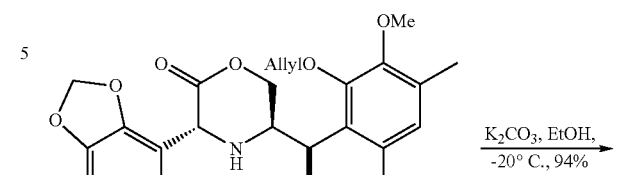

Amino Ester 37

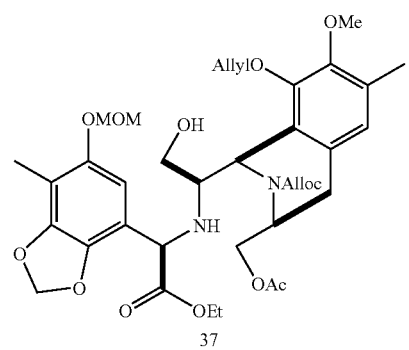

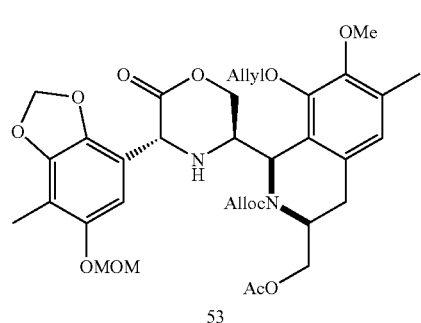

To a mixture of imino lactone 51 (107 mg, 0.22 mmol) and arylboronic acid 52 (66 mg, 0.27 mmol) in anhydrous dichloromethane (1.0 ml), a solution of trifluoroacetic acid (70 mg, 45 μl, 0.62 mmol) in anhydrous dichloromethane (0.2 ml) was added dropwise at room temperature and the resulting mixture was stirred at room temperature for 75 min. The reaction was quenched by addition of saturated sodium hydrogen carbonate and water. And the aqueous phase was extracted with ethyl acetate. The combined organic phases were washed with brine, dried over sodium sulfate, and concentrated under reduced pressure. The residue was purified by flash column chromatography (25%-100% EtOAc in heptane) to afford lactone 53 (83 mg, 0.12 mmol, 55%) as a pale yellow oil. $[\alpha]_D^{23}$ −18 (c=1.0, CHCl$_3$); IR (neat) ν 2929, 1741, 1693, 1455, 1393, 1230, 1108, 1056, 990 cm$^{-1}$; $^1$H NMR (500 MHz, CDCl$_3$) δ6.77 (s, 1H), 6.40 (s, 1H), 6.10 (m, 1H), 5.96 (m, 1H), 5.83 (d, J=1.1 Hz, 1H), 5.76 (m, 1H), 5.68 (d, J=1.1 Hz, 1H), 5.39 (dd, J=17.0, 1.2 Hz, 1H), 5.25 (dd, J=10.3, 1.2 Hz, 1H), 5.0-5.1 (m, 3H), 4.4-4.75 (m, 8H), 4.28 (dd, J=11.5, 1.9 Hz, 1H), 4.07 (br.s, 1H), 3.81 (s, 3H), 3.52 (m, 1H), 3.45 (s, 3H), 2.90 (dd, J=15.4, 12.6 Hz, 1H), 2.76 (dd, J=15.5, 6.7 Hz, 1H), 2.26 (s, 3H), 2.09 (br.s, 6H); $^{13}$C NMR (75 MHz, CDCl$_3$) δ171.1 & 170, 7168.6, 155.6, 151.0, 149.8, 148.4, 146.7, 139.2, 133.9, 132.2, 129.7, 126.4, 125.2, 118.5, 118.3, 118.1, 116.5, 110.7, 106.8, 101.0, 95.7, 74.1, 70.9, 66.9, 64.8, 60.0 & 59.9, 56.1, 55.9, 52.7, 51.8, 51.0, 29.3, 20.8, 15.7, 8.9; HRMS (ESI$^+$) m/z: calc. for C$_{35}$H$_{42}$N$_2$O$_{12}$Na (M+Na)$^+$ 705.2635, found 705.2641.

To a suspension of amino lactone 53 (96 mg, 0.14 mmol) in absolute ethanol (5.0 ml) was added potassium carbonate (19 mg, 0.14 mmol) at −20° C. After stirring at this temperature for 1 hour, the reaction mixture diluted with ethyl acetate and washed with water. The aqueous phase was extracted with ethyl acetate. The combined organic phases were washed with brine, dried over sodium sulfate, and concentrated under reduced pressure. The residue was purified by flash column chromatography (40% EtOAc in heptane) to afford lactone 37 (96 mg, 0.13 mmol, 94%) as a pale yellow oil.

Compound 54

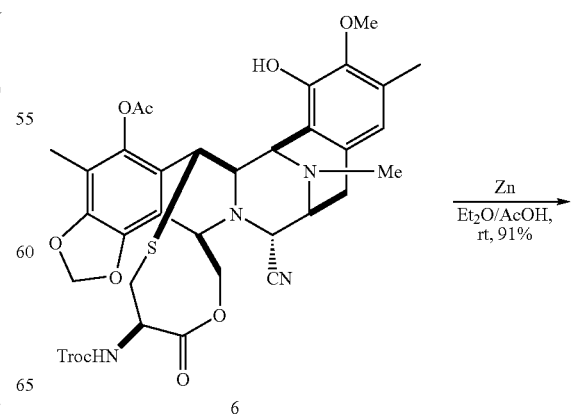

71
-continued

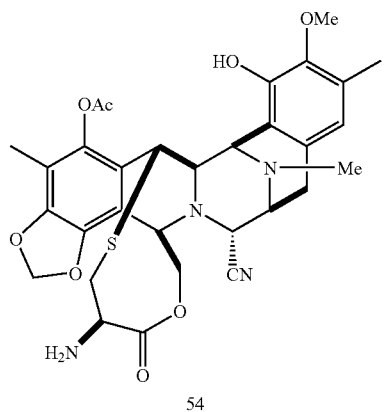

54

72
-continued

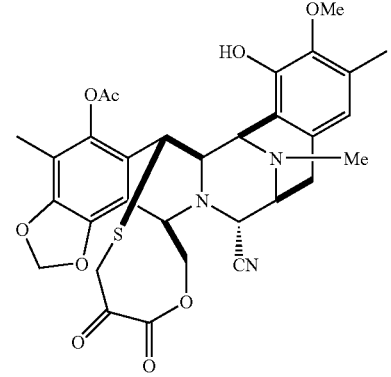

55

To a solution of compound 6 (100 mg, 0.125 mmol) in diethyl ether and acetic acid (2:1, v/v, 6 ml), Zinc powder (648 mg, 9.75 mmol, 78 equiv) was added and the resulting mixture was stirred at 23° C. for another 1 hour. The reaction mixture was diluted with diethyl ether (300 ml) and filtered with celite. The filtrate was concentrated under reduced pressure and the residue was purified by flash column chromatography (80%-100% EtOAc in heptane) to afford amine 54 (72 mg, 92%) as a white film. $[\alpha]_D^{24.5}$ –17.2° (c=1.2, CHCl$_3$). IR (neat film) ν3349, 2932, 1753, 1588, 1453, 1433, 1367, 1236, 1192, 1107, 1087, 1028, 1002, 914 cm$^{-1}$; $^1$H NMR (300 MHz, CDCl$_3$) δ 6.51 (s, 1H), 6.05 (d, J=1.2 Hz, 1H), 5.97 (d, J=1.2 Hz, 1H), 4.99 (d, J=11.6 Hz, 1H), 4.50 (bs, 1H), 4.23 (bs, 2H), 4.17 (d, J=2.5 Hz, 1H), 4.10 (dd, J=11.4, 1.8 Hz, 1H), 3.76 (s, 3H), 3.36-3.42 (m, 2H), 3.25 (s, 1H), 2.89 (s, 1H), 2.88 (d, J=2.0 Hz, 1H), 2.29 (s, 3H), 2.26 (s, 3H), 2.16 (s, 3H), 2.17-2.22 (m, 2H), 2.01 (s, 3H); $^{13}$C NMR (75 MHz, CDCl$_3$) δ 168.65, 147.86, 145.64, 142.92, 140.97, 140.33, 130.53, 129.30, 120.81, 120.49, 118.25, 118.19, 113.74, 113.32, 101.93, 95.46, 61.37, 60.20, 60.02, 59.35, 59.14, 54.68, 54.60, 54.01, 41.71, 41.51, 34.43, 23.82, 20.60, 15.67, 9.64; HRMS (MALDI$^+$) m/z: Calc. for C$_{31}$H$_{35}$N$_4$O$_8$S (M+H)$^+$ 623.2159, found 623.2175.

To a solution of amine 54 (40 mg, 0.064 mmol) in DMF and dichloromethane (1:1, v/v, 4 ml) was added 4-formyl-1-methylpyridinium benzenesulfonate (180 mg, 0.64 mmol, 10 equiv), and the red solution was stirred at 23° C. for another 10 min. To the solution, DBU (86 μl, 0.58 mmol, 9 equiv) was added, and the black suspension was stirred at 23° C. for 15 min before saturated aqueous oxalic acid solution (1.5 ml) was added. The mixture was stirred at 23° C. for 30 min before it was partitioned between diethyl ether (300 ml) and saturated aqueous sodium bicarbonate solution (30 ml). The organic layer was dried over sodium sulfate, concentrated, and the residue was purified by flash column chromatography (33% EtOAc in heptane) to afford ketone 55 (21 mg, 53%) as a white film. $[\alpha]_D^{24.2}$ +109.4° (c=0.6, CHCl$_3$). IR (neat film) ν3471, 2931, 1762, 1728, 1455, 1370, 1269, 1255, 1193, 1107, 1086, 1062, 961 cm$^{-1}$; $^1$H NMR (300 MHz, CDCl$_3$) δ6.48 (s, 1H), 6.10 (d, J=1.0 Hz, 1H), 6.01 (d, J=1.0 Hz, 1H), 5.72 (s, 1H), 5.08 (d, J=11.4 Hz, 1H), 4.65 (bs, 1H), 4.37 (s, 1H), 4.26 (d, J=4.3 Hz, 1H), 4.20 (dd, J=11.4, 1.7 Hz, 1H), 4.10 (d, J=2.5 Hz, 1H), 3.74 (s, 3H), 3.53 (d, J=5.0 Hz, 1H), 3.41 (d, J=8.8 Hz, 1H), 2.89 (dd, J=17.8, 9.3 Hz, 1H), 2.83 (d, J=13.8 Hz, 1H), 2.68 (d, J=17.8 Hz, 1H), 2.55 (d, J=14.0 Hz, 1H), 2.31 (s, 3H), 2.23 (s, 3H), 2.13 (s, 3H), 2.03 (s, 3H); $^{13}$C NMR (75 MHz, CDCl$_3$) δ 186.69, 168.55, 160.51, 147.15, 146.37, 142.95, 141.63, 140.68, 130.43, 129.83, 121.68, 120.02, 117.92, 117.13, 113.48, 113.36, 102.24, 61.74, 61.38, 60.32, 59.78, 58.92, 54.58, 54.54, 43.22, 41.62, 36.85, 24.09, 20.36, 15.80, 9.68; HRMS (MALDI$^+$) m/z: Calc. for C$_{31}$H$_{32}$N$_3$O$_9$S (M+H)$^+$ 622.1843, found 622.1859.

Compound 55

Et 770

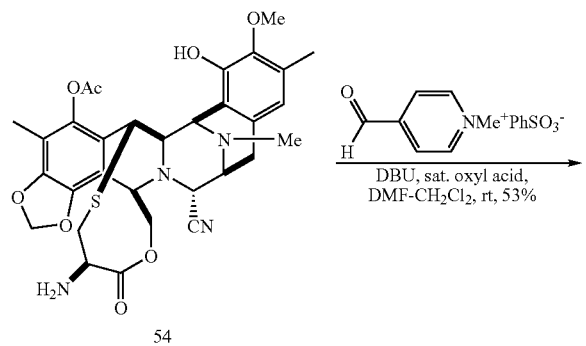

54

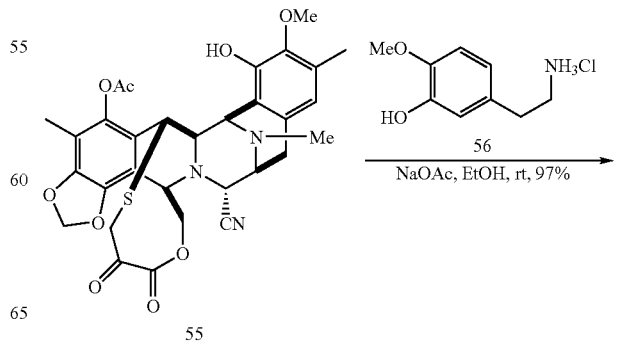

55

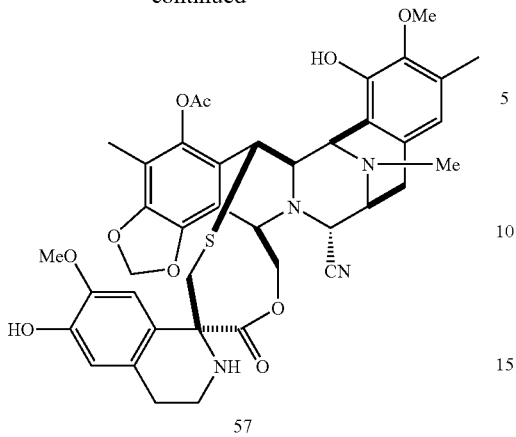

57

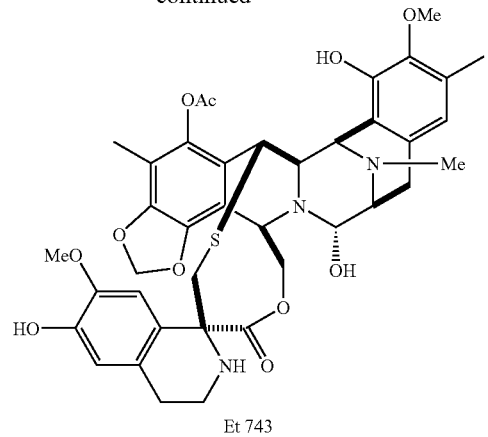

Et 743

A solution of ketone 55 (20 mg, 0.032 mmol), phenethylamine chlorohydride 56 (50 mg, 0.245 mmol, 7.6 equiv) and sodium acetate (26 mg, 0.322 mmol, 10 equiv) in anhydrous ethanol (3 ml) was stirred at 23° C. for 3 hours. The reaction mixture was diluted with ethyl acetate (50 ml) and filtered. The filtrate was concentrated and the residue was purified by flash column chromatography (50% EtOAc in heptane) to afford ecteinascidin 770 (24 mg, 97%) as a white film. $[\alpha]_D^{24.5}$ −50.6° (c=0.7, CHCl$_3$). IR (neat film) ν3434, 2932, 1742, 1588, 1508, 1453, 1369, 1327, 1235, 1106, 1086, 1053, 1028, 959 cm$^{-}$; $^1$H NMR (300 MHz, CDCl$_3$) δ6.59 (s, 1H), 6.46 (s, 1H), 6.43 (s, 1H), 6.03 (s, 1H), 5.96 (s, 1H), 5.75 (s, 1H), 5.46 (s, 1H), 5.00 (d, J=11.5 Hz, 1H), 4.55 (s, 1H), 4.31 (s, 1H), 4.27 (bd, J=4.0 Hz, 1H), 4.17 (d, J=2.5 Hz, 1H), 4.11 (dd, J=11.8, 2.2 Hz, 1H), 3.77 (s, 3H), 3.60 (s, 3H), 3.50 (d, J=4.5 Hz, 1H), 3.44 (m, 1H), 3.09 (ddd, J=11.2, 4.3, 1.0 Hz, 1H), 2.86-2.99 (m, 2H), 2.71-2.81 (m, 1H), 2.52-2.64 (m, 1H), 2.55 (dt, J=15.8, 3.5 Hz, 1H), 2.33 (d, J=12.5 Hz, 1H), 2.31 (s, 3H), 2.25 (s, 3H), 2.18 (s, 3H), 2.12 (d, J=15.0 Hz, 1H), 2.03 (s, 3H); $^{13}$C NMR (75 MHz, CDCl$_3$) δ 172.59, 168.17, 147.83, 145.30, 144.55, 144.32, 143.05, 141.32, 140.12, 130.77, 129.36, 129.13, 125.72, 121.17, 120.72, 118.16, 118.13, 114.11, 114.09, 113.40, 109.81, 101.84, 64.57, 61.12, 60.34, 60.01, 59.66, 59.55, 55.17, 54.71, 54.62, 42.23, 41.84, 41.60, 39.65, 28.79, 24.17, 20.43, 15.81, 9.72; HRMS (MALDI$^+$) m/z: Calc. for C$_{40}$H$_{43}$N$_4$O$_{10}$ (M+H)$^+$ 771.2680, found 771.2699.

Et 743

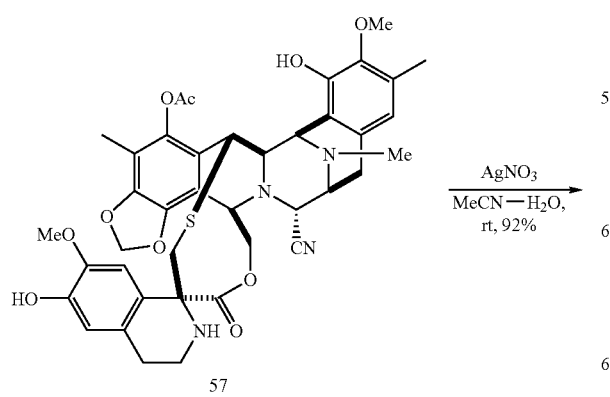

57

To a solution of ecteinascidin 770 (22 mg, 0.0285 mmol) in acetonitrile and water (3:2, v/v, 4 ml) was added silver nitrate (100 mg, 20 equiv). The suspension was stirred at 23° C. for 19 hours at which time a mixture of saturated aqueous sodium chloride solution (1 ml) and saturated aqueous sodium hydrogen carbonate solution (1 ml) was added. The mixture was stirred vigorously at 23° C. for 10 min before it was partitioned between saturated aqueous sodium chloride solution and saturated aqueous sodium hydrogen carbonate solution (20 ml, v/v, 1:1) and extracted with ethyl acetate (3×100 ml). The combined organic layer was dried over sodium sulfate, concentrated, and the residue was purified by flash column chromatography (60% EtOAc in heptane) to afford ecteinascidin 743 (20 mg, 92%) as a pale yellow film. $[\alpha]_D^{24.5}$ −53.8° (c=0.65, CHCl$_3$). IR (neat film) ν3433, 2935, 1762, 1741, 1586, 1511, 1502, 1460, 1452, 1370, 1243, 1087, 1028, 1002, 957 cm$^{-1}$; $^1$H NMR (300 MHz, CDCl$_3$) δ6.59 (s, 1H), 65 (s, 1H), 6.44 (s, 1H), 6.01 (s, 1H), 5.93 (s, 1H), 5.72 (bs, 1H), 5.12 (d, J=11.2 Hz, 1H), 4.80 (s, 1H), 4.47 (d, J=3.0 Hz, 1H), 4.46 (s, 1H), 4.15 (d, J=4.0 Hz, 1H), 4.03 (dd, J=11.2 2.1 Hz, 1H), 3.78 (s, 3H), 3.60 (s, 3H), 3.56 (d, J=4.9 Hz, 1H), 3.17-3.22 (m, 1H), 3.12 (ddd, J=14.1, 10.1, 4.2 Hz, 1H), 2.75-2.93 (m, 3H), 2.59 (ddd, J=15.6, 9.5, 5.3 Hz, 1H), 2.46 (dt, J=15.8, 3.5 Hz, 1H), 2.34 (d, J=17.5 Hz, 1H), 2.31 (s, 3H), 2.25 (s, 3H), 2.16 (s, 3H), 2.08-2.15 (m, 1H), 2.02 (s, 3H); $^{13}$C NMR (125.7 MHz, CDCl$_3$) δ 172.55, 168.34, 147.69, 145.13, 144.44, 144.28, 142.97, 141.29, 140.51, 131.55, 129.19, 129.12, 126.06, 121.87, 120.96, 118.00, 115.96, 114.06, 112.53, 109.84, 101.66, 82.11, 64.68, 61.37, 60.35, 57.80, 57.74, 55.98, 55.15, 54.94, 42.22, 42.16, 41.44, 39.71, 28.85, 24.06, 20.43, 15.80, 9.67; HRMS (MALDI$^+$) m/z: Calc. for C$_{39}$H$_{42}$N$_3$O$_{10}$S (M−OH)$^+$ 744.2605 and C$_{39}$H$_{44}$N$_3$O$_{11}$S (M+H)$^+$ 762.2719, found 744.2590, 762.2696.

Preparation of Et 597 and Et 583:

Taking advantage of the presence of two free hydroxyl groups in ring A of 1h and 1g, a strategy that is different from the synthesis of Et 743 (1) is envisaged and is illustrated in following retro-synthetic Scheme.

1h and 1g ⇒

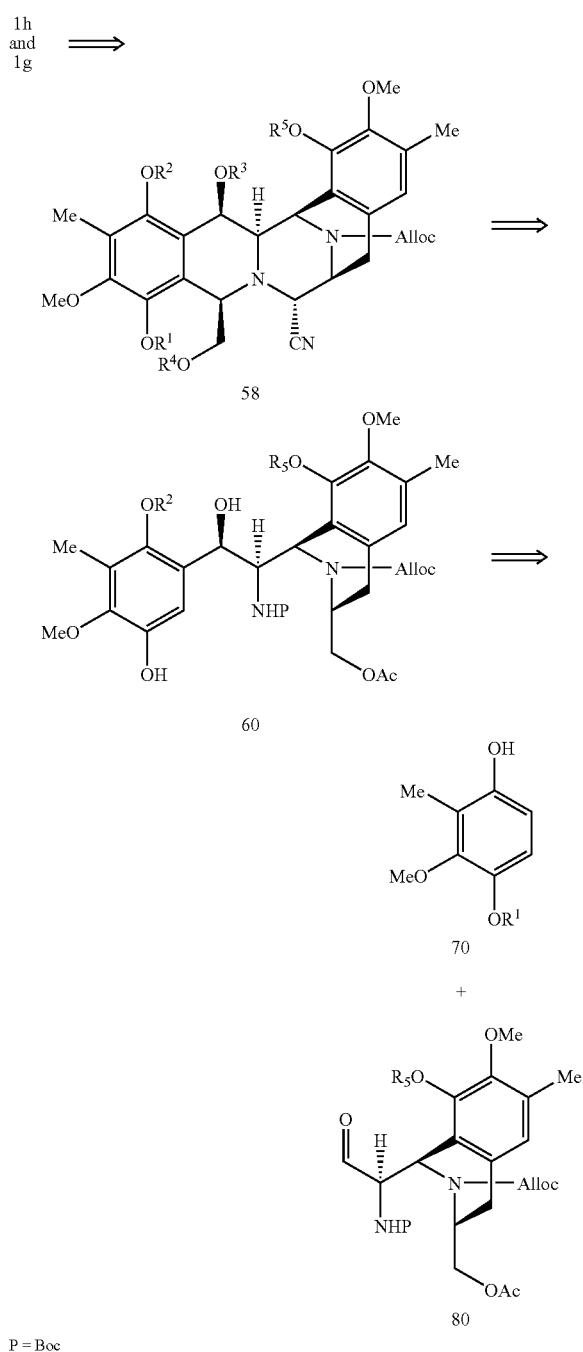

P = Boc

Starting from phenol 70 and tetrahydroisoquinoline 80, a sequence of phenolic aldol condensation followed by a Pictet-Spengler reaction is planned for the construction of highly oxygenated A-B ring system. Intramolecular Strecker reaction would then afford the entire A-B-C-D-E pentacycle which upon closure of 10-membered lactone via formation of the carbon-sulfur bond would lead to the natural products.

Preparation of Compound 70

The synthesis of aromatic segment 70 is summarized in the following Scheme 9. 3-Methoxy-4-hydroxybenzaldehyde (59) was converted to 61 according to the well-established three-step sequence. Interestingly, ortho-lithiation followed by addition of methyl iodide gave a compound wherein both the aromatic ring and the TBS protecting group were methylated. Under optimized conditions (3 equiv of n-BuLi, 4 equiv of MeI), the dual-methylation product 62 was isolated in 92% yield. Removal of MOM group without touching the silyl ether was realized with TMSBr to provide phenol 70 in excellent yield.

Scheme 9

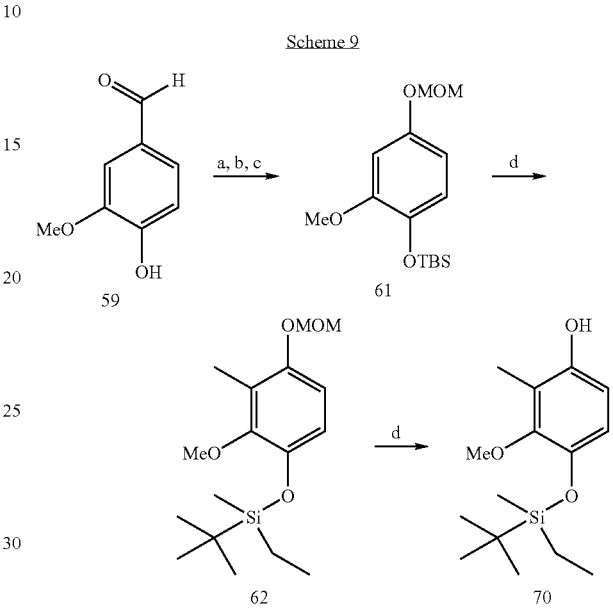

reagents and conditions: Synthesis of A ring unit 70. A) TBSCl, imidazole, DMF, room temperature, 98%; b) mCPBA, CHCl$_3$, 45° C.; then Na$_2$CO$_3$, MeOH, room temperature 85%; c) MOMCl, DIPEA, CH$_2$Cl$_2$, 0° C. to reflux, 96%; d) n-BuLi, THF, -10° C.; then MeI, -78° C. to RT, 92%; e) TMSBr, CH$_2$Cl$_2$, -20° C. to 0° C., 90%. (TBS = tert-butyldimethylsilyl, mCPBA = m-chloroperbenzoic acid, MOM = methoxymethyl, DIPEA = N,N-diisopropylethylamine, DMF = N,N-dimethylformamide).

Preparation of Compound 68

The synthesis of pentacyclic compound 68 is depicted in Scheme 10. The tetrahydroisoquinoline (63) was synthesized featuring a highly diastereoselective Pictet-Spengler condensation between (S)-Garner's aldehyde and (S)-3-hydroxy-4-methoxy-5-methyl phenylalanyl. Selective hydrolysis of the oxazolidine in tetrahydroisoquinoline 63 was more difficult than expected. Eventually, it was realized following conditions that were previously developed for the cleavage of acetonides (CeCl$_3$, oxalic acid, acetonitrile, room temperature) to afford alcohol 64 in 91% yield. Swern oxidation of the primary alcohol furnished the corresponding amino aldehyde 80, which without purification underwent the stereoselective phenolic aldol condensation with magnesium phenolate of 70 to provide the syn amino alcohol 65 in 74% isolated yield as the only isolable diastereomer. The presence of rotamer made the NMR analysis of 65 difficult and it was hard to distinguish if it was a mixture of two diastereomers due to the presence of chiral silicon center. This is nevertheless of no consequence since the silyl protective group will be removed in the next step. Compound 65 was transformed into amino alcohol 66 by a three-step sequence in excellent overall yields: a) protection of phenol and secondary alcohol as the corresponding methoxymethyl ethers; b) simultaneous removal of N-Boc and O-silyl protective groups according to Ohfune's procedure; c) hydrolysis of acetate. The Pictet-Spengler reaction of 66 and 2-O-Troc-acetaldehyde (67, prepared in two steps from ethylene glycol) was the key step of the present synthesis. Pleasantly, the desired transformation was realized efficiently in dichloromethane in the presence of acetic acid and 3 Å molecular sieves to provide 68 as a single diastereomer in 90% yield. Swern oxidation of the amino alcohol 68 followed by zinc chloride-catalyzed intramolecular Strecker reaction provided amino nitrile 69 as one single stereoisomer, thus accomplishing the construction of the pentacyclic ring system with high synthetic efficiency.

Scheme 10

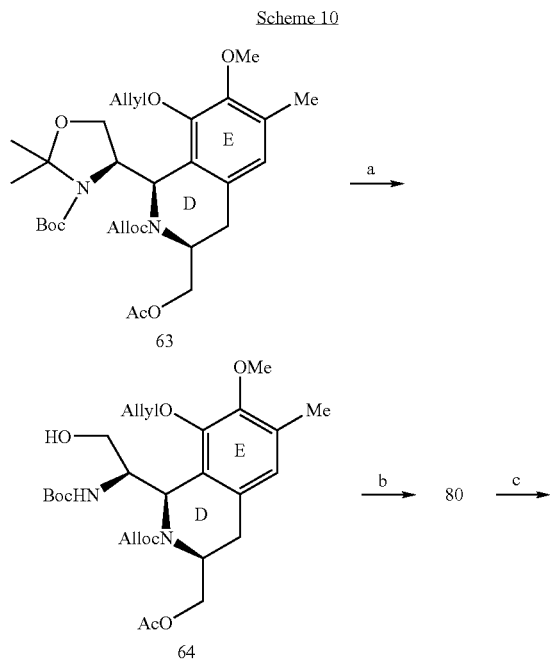

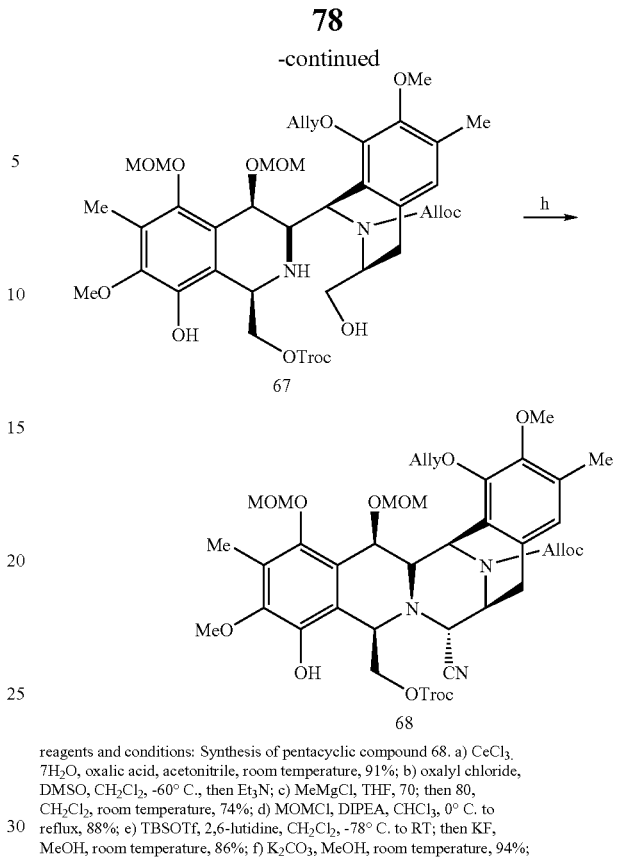

reagents and conditions: Synthesis of pentacyclic compound 68. a) CeCl$_3$·7H$_2$O, oxalic acid, acetonitrile, room temperature, 91%; b) oxalyl chloride, DMSO, CH$_2$Cl$_2$, -60° C., then Et$_3$N; c) MeMgCl, THF, 70; then 80, CH$_2$Cl$_2$, room temperature, 74%; d) MOMCl, DIPEA, CHCl$_3$, 0° C. to reflux, 88%; e) TBSOTf, 2,6-lutidine, CH$_2$Cl$_2$, -78° C. to RT; then KF, MeOH, room temperature, 86%; f) K$_2$CO$_3$, MeOH, room temperature, 94%; g) AcOH, 2-O-Troc-acetaldehyde, 3Å molecular sieves, CH$_2$Cl$_2$, room temperature, 90%; h) oxalyl chloride, DMSO, CH$_2$Cl$_2$, -60° C.; then TMSCN, ZnCl$_2$, CH$_2$Cl$_2$, room temperature, 87%;

Preparation of Compound 1h and 1g

Total synthesis of Et 597 (1g) and Et 583 (1h) is accomplished as shown in Scheme 11. Unmasking the O-Troc group under reductive condition followed by chemoselective allylation of the phenol provided compound 69, which is coupled with (R)—N-Troc-(S-4,4',4"-trimethoxytrityl)Cys to afford the corresponding ester 71 in excellent yield. Removal of S-4,4',4"-trimethoxytrityl group from 71 with Et$_3$SiH/TFA afforded stable thiol 72 in 88% yield after flash column chromatography. Gratifyingly, treatment of the thiol 72 with TMSBr afforded the bridged macrocycle 73 in 60% isolated yield after masking the phenol as the corresponding acetate. In this simple experiment, a complex reaction sequence involving O-MOM deprotection, 1,4-elimination leading to ortho-quinone methide and macrocyclization via an intramolecular Michael addition occurred in a highly ordered manner, to accomplish the key C—S bond-forming process. Simultaneous removal of N-Alloc and O-allyl functions according to Guibé provided amine 74 in 85% yield. A sequence of reductive N-methylation, removal of N-Troc group (zinc/AcOH), and conversion of aminonitrile to aminal (AgNO$_3$ in a mixture of acetonitrile and water) afforded ecteinascidin 597 (1g) in excellent overall yields. Similarly, amine 74 was converted to ecteinascidin 583 (1h) in a two-step sequence. Synthetic Et 597 (1g) and 583 (1h) exhibited physical, spectroscopic, and spectrometric characteristics (1H, $^{13}$C NMR, IR, [α]$_D$, and HRMS) identical to those reported for natural products.

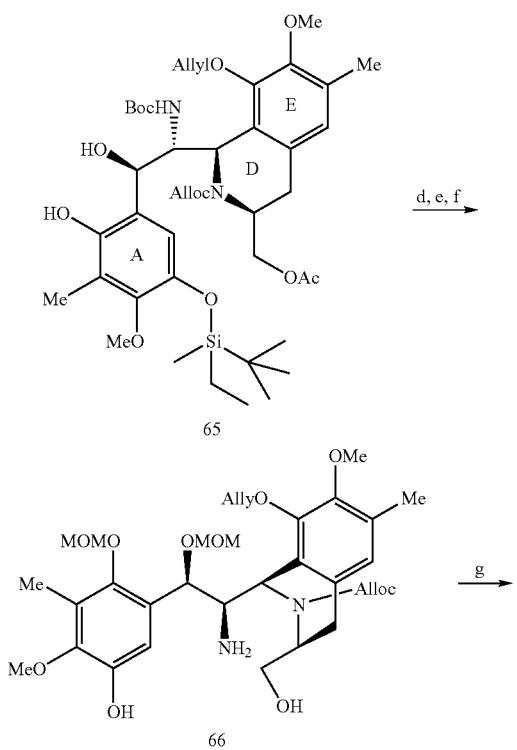

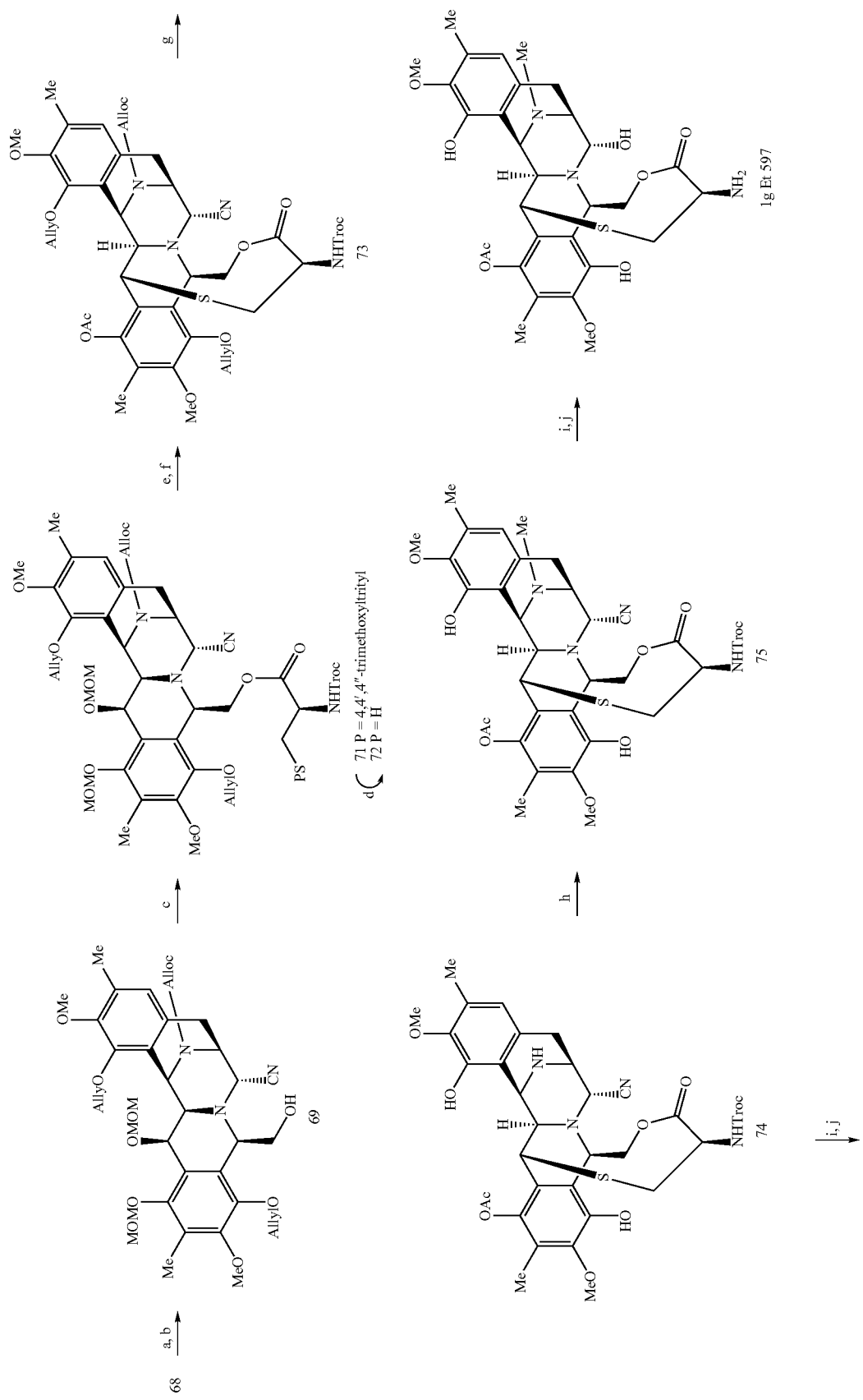

-continued

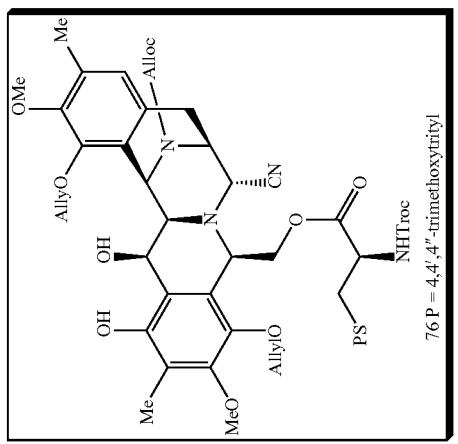

76 P = 4,4′,4″-trimethoxytrityl

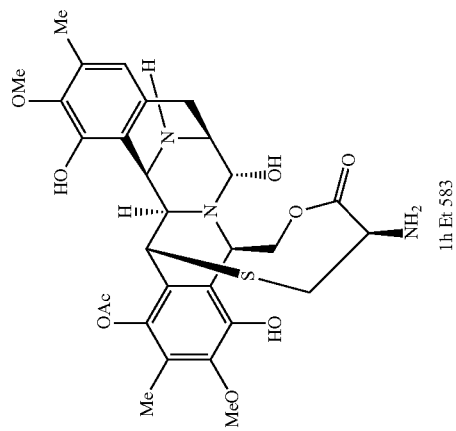

1h Et 583 reagents and conditions: Synthesis of Et 597 (1g) and 583 (1h). a) Zn, AcOH, Et₂O room temperature, 90%; b) allyl bromide, K₂CO₃, acetonitrile, room temperature, 94%; c) EDCI, DMAP, (R)-N-Troc-(S-4,4′,4″-trimethoxytrityl) Cys, CH₂Cl₂, room temperature, 93%; d) Et₃SiH, TFA CH₂Cl₂, room temperature, 87%; e) TMSBr; CH₂Cl₂, −20° C. to 10° C.; f) Ac₂O, Py, DMAP, CH₂Cl₂, room temperature, 60%; g) Pd(Ph₃P)₄, n-Bu₃SnH, AcOH, CH₂Cl₂, room temperature, 85%; h) CH₂O, NaBH₃CN, AcOH, MeCN/MeOH, room temperature, 95%; i) Zn, AcOH, Et₂O, room temperature, 89% for Et 597, 86% for Et 583; j) AgNO₃, MeCN/H₂O, room temperature, 92% for Et 597, 88% for Et 583. (Py = pyridine, TFA = trifluoroacetic acid, EDCI = 1-(3-dimethylaminopropyl)-3-ethylcarbodiimide hydrochloride, DMSO = dimethyl sulfoxyde).

In summary, convergent total syntheses of Et 597 (1g) and 583 (1h) have been achieved for the first time from the readily accessible starting materials. Notable features of our approach include: (a) stereoselective aldol reaction for the coupling of the two segments, A ring (70) and D-E unit (80), (b) a highly stereoselective Pictet-Spengler reaction for the construction of B ring, (c) TMSBr promoted macrocyclization of the thiol 72 leading to the 1,4-bridged-10-membered ring. The synthesis is straightforward without using sophisticated reaction conditions and should potentially be amenable to large-scale production.

The invention claimed is:

1. An intermediate of the following (I)

in which $R_1$ and $R_2$ represent independently of each other a $C_1$-$C_{12}$ alkyl group, a ($C_1$-$C_{12}$ alkoxy)carbonyl group, optionally substituted by one, two or three halogen atom, a ($C_2$-$C_{12}$ alkenyloxy) carbonyl group, an acyl group, an aryl($C_1$-$C_{12}$)alkyl group, an arylalkoxy carbonyl group, a ($C_1$-$C_{12}$ alkyl)sulfonyl group or an arylsulfonyl group, $R_3$ represents an O-protecting group, $R_4$ and $R_5$ represent independently of each other a hydrogen atom or an O-protecting group, $R_6$ represents an O-protecting group and $R_7$ represents a $C_1$-$C_{12}$ alkyl group or —$OR_6$ and —$OR_7$ form together a group —$OCH_2O$—.

2. The intermediate according to claim 1, which has the following formula (I bis)

(I bis)

wherein $R_1$, $R_2$ and $R_3$ have the same meaning as in claim 1.

3. The intermediate according to claim 1, wherein $R_4$, $R_5$ and $R_6$ represent independently of each other an O-protecting group and $R_7$ represents a $C_1$-$C_{12}$ alkyl group.

4. The intermediate according to claim 3, wherein $R_4$ and $R_5$ independently of each other represent a methoxymethyl group, $R_6$ represents an allyl group and $R_7$ represents a methyl group.

5. The intermediate according to any of claims 1 to 4, wherein $R_1$ represents a 2,2,2,trichloroethoxycarbonyl group, $R_2$ represents an allyloxycarbonyl group and $R_3$ represents an allyl group.

6. A process of preparation of an intermediate of formula (I) according to claim 1 which comprises the step (p) of coupling of the intermediate of the following formula (II)

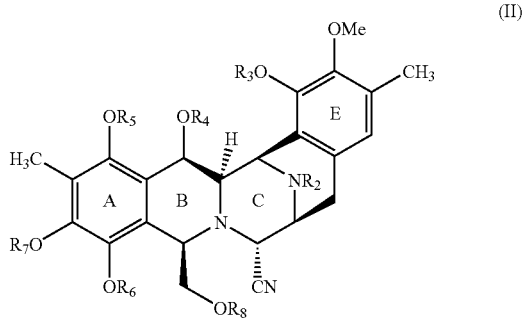

(II)

in which $R_2$, $R_3$, $R_4$, $R_5$, $R_6$ and $R_7$ have the same meaning as in claim 1 and $R_8$ represents H with the compound (R)—N—$R_1$—(S-4,4',4''-trimethoxyltrityl) cysteine in which $R_1$ has the same meaning as in claim 1.

7. The process according to claim 6, which comprises a prior step (p1) of preparation of the intermediate of formula (II) according to claim 6 wherein $R_6$ represents an O-protecting group by the protection of the hydroxy group with an O-protecting group $R_6$ of the intermediate of the following formula (IIbis)

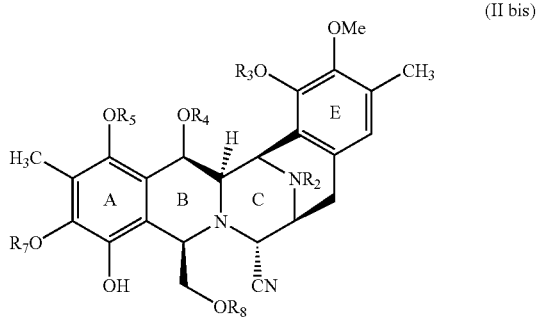

(II bis)

in which $R_2$, $R_3$, $R_4$, $R_5$, $R_7$ and $R_8$ have the same meaning as in claim 6.

* * * * *